United States Patent [19]
Oishi et al.

[11] Patent Number: 5,646,240
[45] Date of Patent: Jul. 8, 1997

[54] DIGUANAMINES AND PREPARATION PROCESS, DERIVATIVES AND USE THEREOF

[75] Inventors: Tetsuya Oishi, Kanagawa-ken; Jin Suzuki, Tokyo; Kouhei Ohkawa, Kanagawa-ken; Hiroshi Ono, Osaka, all of Japan

[73] Assignee: Mitsui Toatsu Chemicals, Inc., Tokyo, Japan

[21] Appl. No.: 619,084

[22] Filed: Mar. 21, 1996

Related U.S. Application Data

[62] Division of Ser. No. 414,011, Mar. 30, 1995, which is a division of Ser. No. 201,391, Feb. 24, 1994, Pat. No. 5,596,039, which is a continuation-in-part of Ser. No. 186,550, Jan. 26, 1994, abandoned, which is a continuation of Ser. No. 983,855, filed as PCT/JP93/00094, Jan. 27, 1993, abandoned.

[30] Foreign Application Priority Data

| Feb. 24, 1993 | [JP] | Japan | 5-035198 |
| Feb. 24, 1993 | [JP] | Japan | 5-035199 |
| Feb. 24, 1993 | [JP] | Japan | 5-035200 |
| Mar. 3, 1993 | [JP] | Japan | 5-043048 |
| Mar. 12, 1993 | [JP] | Japan | 5-051775 |
| Apr. 14, 1993 | [JP] | Japan | 5-087499 |

[51] Int. Cl.$^6$ .................... C08G 59/00; C08G 73/06
[52] U.S. Cl. .................... 528/403; 528/230; 528/248; 528/253; 528/254; 528/258; 528/393; 528/421; 528/422; 528/423; 525/472; 525/509; 525/510; 525/515; 424/604; 424/722; 424/729; 424/755; 424/765; 424/770; 424/777; 424/779; 424/829
[58] Field of Search .................... 528/393, 403, 528/421, 422, 423, 230, 248, 253, 254, 258; 525/472, 509, 510, 515; 524/722, 729, 604, 755, 765, 770, 777, 779, 829

[56] References Cited

U.S. PATENT DOCUMENTS

| 2,532,519 | 12/1950 | Kenson-Simons . |
| 2,901,464 | 8/1959 | Schaefer et al. . |
| 3,408,254 | 10/1968 | Greene et al. . |
| 3,434,983 | 3/1969 | Standish et al. . |

FOREIGN PATENT DOCUMENTS

| 292306 | 11/1988 | European Pat. Off. . |
| 300787 | 1/1989 | European Pat. Off. . |
| 303441 | 2/1989 | European Pat. Off. . |
| 391665 | 10/1990 | European Pat. Off. . |
| 422402 | 4/1991 | European Pat. Off. . |
| 436393 | 7/1991 | European Pat. Off. . |

OTHER PUBLICATIONS

Patent Abstracts of Japan, vol. 17, No. 644(C-1134) Nov. 30, 1994.

Primary Examiner—Samuel A. Acquah
Attorney, Agent, or Firm—Burns, Doane, Swecker & Mathis

[57] ABSTRACT

Provided by the present invention are novel diguanamine derivatives, led by 2,5/2,6-bis(4,6-diamino-1,3,5-triazin-2-yl)-bicyclo[2.2.1]heptanes and 1,3/1,4-bis(4,6-diamino-1,3,5-triazin-2-yl)-cyclohexanes, and derivatives thereof, applications of these compounds in fields such as adhesives and paints, utilization of these compounds in flame-retarding, thermal stabilization and compatibilization methods of resins, thermosetting molding compositions and thermosetting expansion-molding compositions making use of these compounds, as well as polymeric microspheres also using these compounds. These compounds are expected to find wide spread industrial utility as various excellent properties can be obtained by using them.

5 Claims, 4 Drawing Sheets

DIGUANAMINES AND PREPARATION PROCESS, DERIVATIVES AND USE THEREOF

This application is a divisional of application Ser. No. 08/414,011, filed Mar. 30, 1995, which is a divisional of application Ser. No. 08/201,391 filed on Feb. 24, 1994, now U.S. Pat. No. 5,596,037, which is a continuation-in-part application Ser. No. 08/186,550 filed on Jan. 26, 1994, now abandoned, which is a continuation of Ser. No. 07/983,855 filed as PCT/JP93/00094 on Jan. 27, 1993, now abandoned.

BACKGROUND OF THE INVENTION a) Field of the Invention

This invention consists of three invention groups. The first invention group relates to novel diguanamines and diguanamine derivatives as well as their use in paints, adhesives and the like; the second invention group is concerned with flame-retarding, thermal stabilization and compatibilization methods of resins, said methods making use of the diguanamines or novel diguanamine derivatives, and also with similar applications of polymeric microspheres obtained from such diguanamines; and the third invention group pertains to their use as thermosetting molding compositions and thermosetting expansion-molding compositions and also to preparation processes of such diguanamines and diguanamine derivatives.

To facilitate understanding of the present invention which involves these invention groups, this specification is edited in a somewhat unusual order so that the invention is described group by group except for some descriptions.

hardness and gloss, colorless clearness, great chemical resistance and waterproofness and excellent abrasion resistance and electrical properties and, as curing agents, for the superb pot life of the resulting resins.

Further, a variety of research and development work has been conducted on such melamines and guanamines containing an aminotriazine group, resulting in the provision of even polyfunctional guanamines which contain a tetrafunctional group or a still higher functional group and show excellent characteristic properties from the viewpoint of the flexibility, toughness, high hardness, waterproofness, curability and the like of resins.

Such polyfunctional guanamines are absolutely different in structure from the novel diguanamines according to the present invention, so that it is extremely difficult to make a comparison therebetween. For the sake of reference, however, examples which may be given boldly include phthaloguanamine represented by:

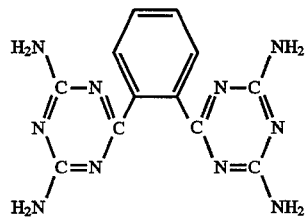

and spiroguanamine represented by:

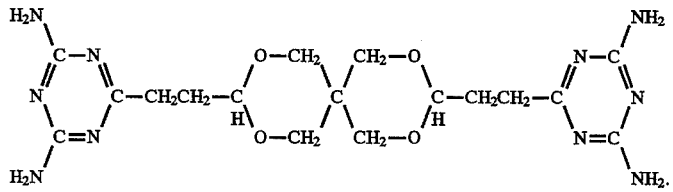

FIRST INVENTION GROUP

TECHNICAL FIELD

This invention relates to novel diguanamines, which are useful as polymerizable monomers, as resin raw materials for paint resins, adhesive resins, paper coating resins, fiber treatment resins, powder coating resins and building materials, as raw materials for guanamine compound derivatives, as curing agents for epoxy resins and urethane resins, and as modifiers for high molecular substances such as rubber materials. The present invention is also concerned with a preparation process of the diguanamines, their derivatives useful as curing agents and intermediates for various resins, and also with use of the diguanamines and the derivatives thereof.

BACKGROUND ART

As resin raw materials for paint resins, adhesive resins, paper coating resins, fiber treatment resins and hide treatments, curing agents for various resins, modifiers for rubber materials, modifiers for organic materials, and the like, guanamines containing an aminotriazine group, such as melamine and benzoguanamine, have heretofore been used widely for their excellent properties including the high The former compound is, however, accompanied by drawbacks such that resins obtained using it as a raw material are very poor in ultraviolet light resistance and weatherability and cannot hence be used at all as resin raw materials for exterior paints, weatherproof paints, automotive paints and building resins or are subjected to a considerable limitation upon such applications and that a substantial limitation is also imposed on its use as a raw material for water-base paint resins because the water reducibility of amino resins formed of phthaloguanamines as its derivatives is still insufficient in practice although it has been improved somewhat over conventional melamine-base amino resins. The latter compound, on the hand, is also accompanied by drawbacks such that resins obtained using it as a raw material have poor inferior heat resistance and poor wheatherability, ultraviolet light resistance and waterproofness and are difficult to retain their expected functions outdoors over a long time as resins for exterior paints, weatherproof paints, automotive paints and building materials. Further, because of the low activity of the amino groups in the latter compound as typified, for example, by the low reaction velocity of the reaction of the latter compound for the formation of a methylol derivative, the latter compound also involves such a problem that a substantial limitation is imposed on the production of various useful guanamine derivatives, resins and resin curing agents available by reactions of the amino groups and also on the production of formaldehyde co-condensation polymers between the latter compound and compounds such as melamine and benzoguanamine. Moreover, a reaction mixture obtained by the formation of a methylol derivative of the latter compound can hardly be obtained as a clear solution, leading to a further drawback such that when employed as a raw material for water-base resins, for example, water-base paint resins, adhesive resins, paper coating resins and fiber treatment resins, sufficient properties can hardly be obtained in the smoothness, curability and physical properties of the resulting coating films and the reaction mixture cannot be used for such applications or is subjected to a considerable limitation in such applications. The latter compound is accompanied by a still further drawback such that production of spironitrile as a starting material for the preparation of the latter compound involves not only technical problems such as the need for many complex steps including a cumbersome purification step but also a substantial impairment in economy. As has been described above, these compounds have been subjected to significant technical and economical limitations upon their use and preparation.

DISCLOSURE OF THE INVENTION

With the foregoing drawbacks in view, the present inventors have proceeded with an extensive investigation. As a result, diguanamines totally different in structure and characteristic properties from the multi-functional diguanamines described above for the sake of reference have been found. These diguanamines contain active amino groups which show excellent reactivity to compounds having various functional groups. Owing to the inclusion of eight active hydrogen atoms, the degree of methylol derivation and the like can be selected from a wide range. They are excellent in weatherability, ultraviolet light resistance and the like, so that they can retain their expected functions outdoors or under similar conditions over a long time. Further, their methylol derivatives are excellent in properties such as water dilution, curability, waterproofness, antifouling property, flexibility, hardness and toughness. An excellent process for the preparation of such diguanamines has also been found. According to the process, each target diguanamine compound can be obtained at a high purity with production of byproducts in extremely small amounts and in a high yield from a corresponding dicarbonitrile available at low cost and requires simple preparation steps such as a simple purification and isolation step. These findings have led to the present invention.

As derivatives available from such useful diguanamines, the present inventors have also prepared N-methylol derivatives by reacting the diguanamines with aldehydes, etherified diguanamines by etherification of the N-methylol derivatives with alcohols, and their initial condensates. The present inventors have also found curing agents for various resins, thermosetting compositions containing these derivatives useful as raw materials for resins such as paint resins, and thermosetting resin compositions containing the diguanamines and epoxy-containing resins and useful as paint resins, powder coating resins and adhesive resins, leading to the present invention.

The diguanamines described above are extremely useful compounds, and can provide polymers, compounds and compositions excellent as rubber modifiers, optical materials, resist materials, electrical insulating materials, automotive paints, paints for home electric and electronic appliances, antifouling paints, weatherproof paints, fluorescent paints, resinous building materials, powder coatings, water-base paints, oil-base paints, paper coating resins, fiber treatment resins, adhesive resins, IC packaging resins, anti-corrosion resins, polymer modifiers, hide treatments, plastic magnets, latex antioxidants, electrophotographic photoconductors, surfactants, agricultural chemicals, medicines, etc.

The present invention therefore provides:

(a) a diguanamine represented by the following formula (1):

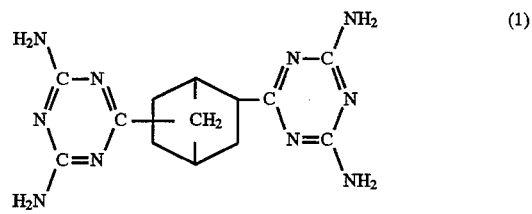

wherein the bonding sites of the 4,6-diamino-1,3,5-triazin-2-yl groups are the 2,5- or 2,6-positions, or by the following formula (2)

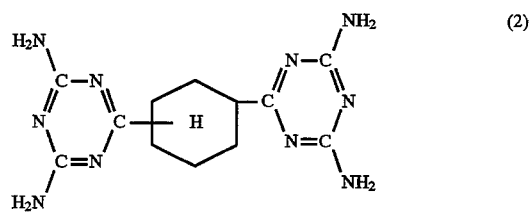

wherein the bonding sites of the 4,6-diamino-1,3,5-triazin-2-yl groups are the 1,2-, 1,3- or 1,4-positions;

(b) a process for the preparation of a diguanamine, which comprises reacting a dicarbonitrile, which is represented by the following formula (3):

wherein the bonding sites of the cyano groups are the 2,5- or 2,6-positions, or by the following formula (4):

wherein the bonding sites of the cyano groups are the 1,2-, 1,3- or 1,4-positions, with dicyandiamide in the presence of a basic catalyst;

(c) a process for the preparation of a diguanamine, as described above under (b), wherein the basic catalyst is at least one compound selected from the group consisting of alkali metals, alkali metal hydroxides, alkaline earth metal hydroxides, alkali metal alcoholates, alkali metal salts of dicyandiamide, alkaline earth metal salts of dicyandiamide, amines and ammonia;

(d) a process for the preparation of a diguanamine, as described above under (b), wherein the reaction is conducted using as a reaction solvent at least one solvent selected from the group consisting of non-aqueous protonic solvents and aprotonic polar solvents;

(e) a process for the preparation of a diguanamine, as described above under (b), wherein the reaction is conducted in a temperature range of from 60° C. to 200° C.;

(f) an N-methylol diguanamine obtained by subjecting the diguanamine described above under (a) and an aldehyde to an addition reaction;

(g) an etherified diguanamine obtained by subjecting the N-methylol diguanamine derivative as described above under (f) and at least one alcohol selected from alcohols having 1–20 carbon atoms to esterification, said etherified diguanamine containing at least one $R_1OCH_2$ group wherein $R_1$ represents a residual group formed by removing a hydroxyl group form the alcohol;

(h) a primary condensate of N-methylol diguanamine obtained by subjecting the diguanamine described above under (a), a condensable compound as an optional reactant, and an aldehyde to addition condensation, having an average addition condensation degree greater than 1 and containing at least one methylol group;

(i) a primary condensate of etherified diguanamine obtained by subjecting the diguanamine described above under (a), a condensable compound as an optional reactant and an aldehyde to an addition reaction or addition condensation reaction and then subjecting the reaction product and at least one alcohol selected from alcohols having 1–20 carbon atoms to etherification and optionally to simultaneous condensation, having an average addition condensation degree greater than 1 and containing at least one $R_1OCH_2$ group wherein $R_1$ has the same meaning as defined above);

(j) a thermosetting composition comprising, as an essential component, at least one compound selected from the group consisting of the N-methylol diguanamines as described above under (f), the etherified diguanamines as described above under (g), the primary condensates of the N-methylol diguanamines described above under (h), and the primary condensates of the etherified diguanamines described above under (i);

(k) a thermosetting composition as described above under (j), further comprising a resin curable through a reaction with the component described above under (j);

(l) a paint resin composition comprising the thermosetting composition described above under (k);

(m) a thermosetting resin composition comprising the diguanamine as described above under (a) and an epoxy-containing resin;

(n) a paint resin composition comprising the thermosetting resin composition described above under (m);

(o) a paint resin composition as described above under (n), said composition being a powder coating resin composition; and (p) an adhesive resin composition comprising the thermosetting resin composition as described above under (m).

BEST MODE FOR CARRYING OUT THE INVENTION

Figure 1:
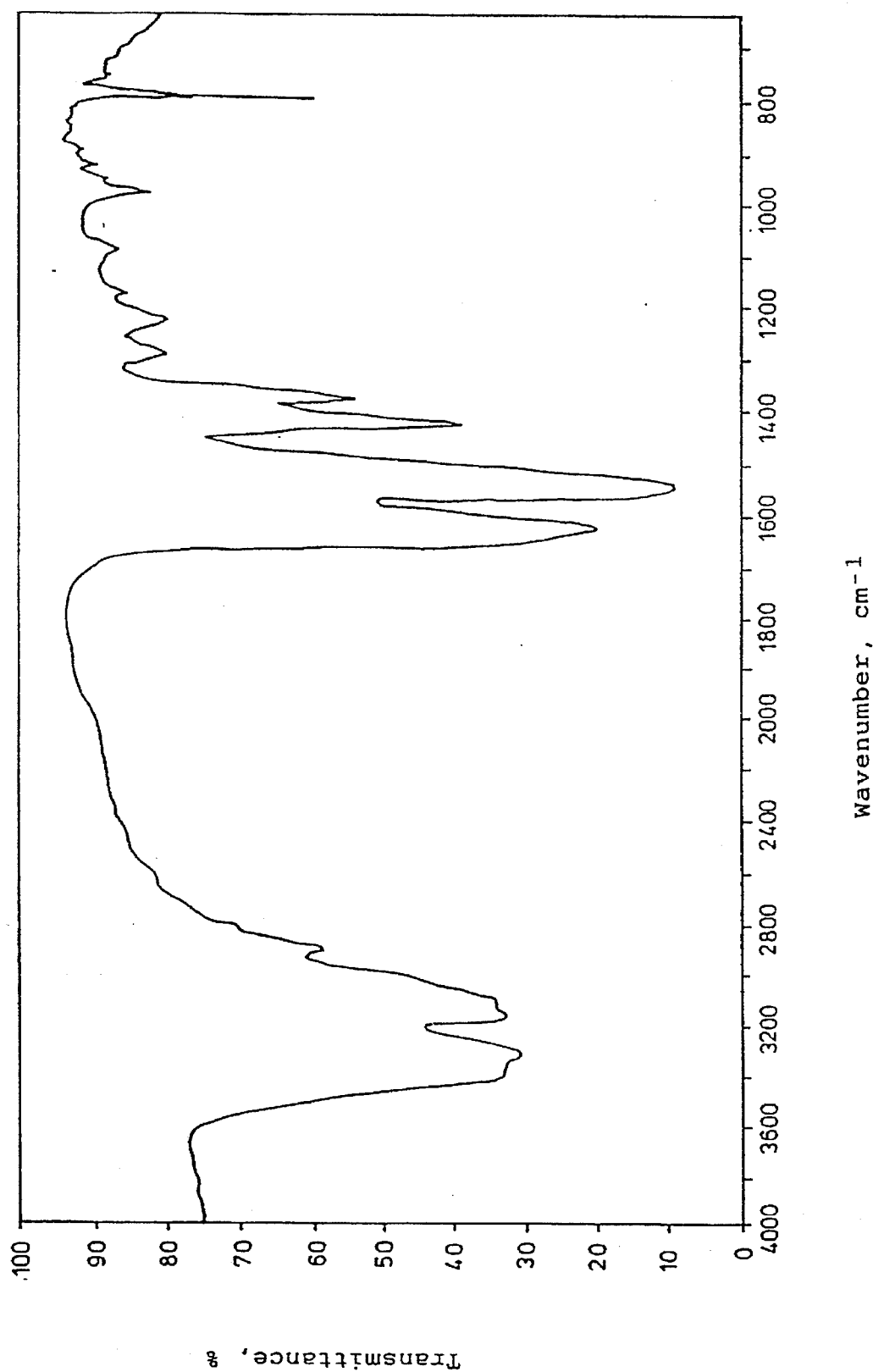
FIG. 1 is an infrared absorption spectrum of a compound obtained in Example 1.

In the diguanamine (1) according to this invention, the bonding sites of the 4,6-diamino-1,3,5-triazin-2-yl groups are the 2,5- or 2,6-positions. The configuration of such groups is an endo-endo form, end-exo form or exo-exo form. These stereoisomers are all useful compounds.

Although the diguanamine (1) is a compound selected from the group consisting of the above-described isomers in bonding sites or configuration, mixtures of different compounds selected from such a group are also extremely useful from the industrial viewpoint like the individual compounds.

Specific examples of the diguanamine (1) include, but are not limited to, 2,5-bis(4,6-diamino-1,3,5-triazin-2-yl)-bicyclo[2.2.1]heptane (end-exo form), 2,5-bis(4,6-diamino-1,3,5-triazin2-yl)-bicyclo[2.2.1]-heptane (exo-exo form), 2,6-bis(4,6-diamino-1,3,5-triazin2-yl)-bicyclo[2.2.1] heptane (endo-endo form), and 2,6-bis(4,6-diamino-1,3,5-triazin2-yl)-bicyclo[2.2.1]heptane (exo-exo form).

In the diguanamine (2) according to this invention, the bonding sites of 4,6-diamino-1,3,5-triazin-2-yl groups are the 1,2-, 1,3- or 1,4-positions. The configuration of such groups are either a trans form or a cis form. These stereoisomers are all useful compounds.

Although the diguanamine (2) is a compound selected from the group consisting of the above-described isomers in bonding sites or configuration, mixtures of different compounds selected from such a group are also extremely useful from the industrial viewpoint like the individual compounds.

Specific examples of the diguanamine (2) include, but are not limited to, 1,2-bis(4,6-diamino-1,3,5-triazin-2-yl)-cyclohexane (cis form), 1,2-bis(4,6-diamino-1,3,5-triazin-2-yl)-cyclohexane (trans form), 1,3-bis(4,6-diamino-1,3,5-triazin-2-yl)-cyclohexane (trans form), 1,3-bis(4,6-diamino-1,3,5-triazin-2-yl)-cyclohexane (cis form), 1,4-bis(4,6-diamino-1,3,5-triazin-2-yl)-cyclohexane (trans form), and 1,4-bis(4,6-diamino-1,3,5-triazin-2-yl)-cyclohexane (cis form).

Each diguanamine according to the present invention can be obtained, for example, by a process in which a dicarbonitrile represented by the following formula (3):

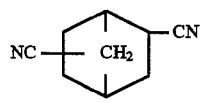

(3)

wherein the bonding sites of the cyano groups are the 2,5- or 2,6-positions, or
by the following formula (4):

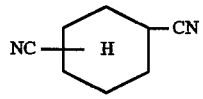

(4)

wherein the bonding sites of the cyano groups are the 1,2-, 1,3- or 1,4-positions is reacted with dicyandiamide in the presence of a basic catalyst or by a process in which an ester of a dicarboxylic acid corresponding to the dicarbonitrile and a biguanide are reacted optionally in the presence of a basic compound. The former process is excellent both technically and economically and is extremely practical, because the raw materials are readily available and are easy to handle, byproducts are minimized and the target compound can be obtained with high purity, preparation including a purification step is simple, the loss of the raw materials is very small, and the target compound can be obtained in a high yield. It is however to be noted that the preparation process of the diguanamine is not necessarily limited to these processes.

In the dicarbonitrile (3) in the preparation process of the diguanamine, said process pertaining to this invention, the bonding sites of the cyano groups are the 2,5- or 2,6-positions. The configuration of these groups is an endo-endo form, endo-exo form or exo-exo form. These stereoisomers are all useful. Although the dicarbonitrile (3) is a compound selected from the group consisting of the above-described isomers in bonding sites or configuration, mixtures of different compounds selected from such a group are also useful like the individual compounds.

The dicarbonitrile (3) can be obtained, for example, by a process in which bicyclo[2.2.1]hepta-5-ene-2-carbonitrile and a hydrogen cyanide are reacted in the presence of a particular catalyst such as $Co_2(CO)_8$, $Fe(CO)_5$ or $Ni[P(OC_6H_5)_3]_4$ as disclosed in U.S. Pat. No. 2,666,748 or the like, by a process in which 5- (and/or 6-)cyano-bicyclo[2.2.1]hepta-2-carbaldehyde and a hydroxylamine are reacted as disclosed in U.S. Pat. No. 3,143,570 or the like, or by a process in which 2,5- (and/or 2,6-)dichloro-bicyclo[2.2.1]heptane and a cyanating agent such as an alkali metal cyanate or alkaline earth metal cyanate are reacted. It is however to be noted that the preparation process is not limited to such processes.

Specific examples of the dicarbonitrile (3) include, but are not limited to, bicyclo[2.2.1]heptane-2,5-dicarbonitrile (endo-exo form), bicyclo[2.2.1]heptane-2,5-dicarbonitrile (endo-endo form), bicyclo[2.2.1]heptane-2,6-dicarbonitrile (endo-exo form), and bicyclo[2.2.1]heptane-2,6-dicarbonitrile (exo-exo form).

In the dicarbonitrile (4) in the preparation process of the diguanamine, said process pertaining to this invention, the bonding sites of the cyano groups are the 1,2-, 1,3- or 1,4-positions. The configuration of these groups is either a trans form or a cis form. These stereoisomers are all useful compounds. Although the dicarbonitrile (4) is a compound selected from the group consisting of the above-described isomers in bonding sites or configuration, mixtures of different compounds selected from such a group are also useful like the individual compounds.

The dicarbonitrile (4) can be obtained, for example, by a process in which 4-cyanocylohexene and hydrogen cyanide are reacted in the presence of a catalyst such as $Ni[P(OC_6H_5)_3]_4$ as disclosed in U.S. Pat. No. 3,496,217 or the like, by a process in which 3- (and/or 4-)cyano-cyclohexanecarbaldehyde and a hydroxylamine are reacted as disclosed, by a process in which a dihalogenated cyclohexane corresponding to the dicarbonitrile (4) and a cyanating agent such as an alkali metal cyanate or alkaline earth metal cyanate are reacted, by a process in which a dicarboxylic acid corresponding to the dicarbonitrile (4) or the diammonium salt, diamide or diester derivative of the dicarboxylic acid and ammonia are reacted using a dehydrating agent such as alumina catalyst or thionyl chloride, or by a process in which 1-cyanocyclohexene and hydrogen cyanide are reacted in the presence of an alkali such as sodium hydroxide. It is however to be noted that the preparation process is not limited to such processes.

Specific examples of the dicarbonitrile (4) include, but are not limited to, 1,2-cyclohexanedicarbonitrile (trans form), 1,3-cyclohexanedicarbonitrile (trans form), 1,3-cyclohexanedicarbonitrile (cis form), 1,4-cyclohexanedicarbonitrile (trans form), and 1,4-cyclohexanedicarbonitrile (cis form).

In the process of the present invention for the preparation of the diguanamine, the molar ratio of the dicarbonitrile to dicyandiamide to be reacted with each other can be chosen suitably as needed. The molar ratio of the dicarbonitrile to dicyandiamide to be reacted with each other is 1:2 stoichiometrically. Use of dicyandiamide at an unduly small molar ratio relative to the dicarbonitrile is not preferred because the yield of the diguanamine according to this invention becomes low and, moreover, the corresponding monoguanamine [1:1 (by molar ratio) reaction product of the dicarbonitrile and dicyandiamide] is formed more and the purification step and the like thus become irksome. Use of dicyandiamide at an unduly large molar ratio makes irksome the removal, separation and the like of unreacted dicyandiamide, etc. Use of dicyandiamide at such an unduly small or large molar ratio is therefore not preferred both technically and economically. With a view toward improving the yield of the diguanamine according to the present invention and also simplifying the process including the purification step, it is generally desired to react 1.5–10.0 moles, preferably 2.0–5.0 moles of dicyandiamide with 1 mole of the dicarbonitrile.

Examples of the basic catalyst in the process of the present invention for the preparation of the diguanamine include alkali metals such as potassium and sodium; alkali metal and alkaline earth metal hydroxides such as lithium hydroxide, potassium hydroxide, sodium hydroxide, calcium hydroxide and barium hydroxide; alkali metal and alkaline earth metal carbonates such as potassium carbonate, sodium carbonate and barium carbonate; alkali metal alcoholates such as potassium ethylate, sodium methylate and sodium ethylate; alkali metal and alkaline earth metal salts of dicyandiamide; amines such as 1,8-diazabicyclo[5.4.0]undecene-7, triethylenediamine, piperidine, ethylenediamine, diethylenetriamine, pyrrolidone and tetrahydroquinoline; and ammonia. Particularly preferred are alkali metals, alkali metal hydroxides, alkaline earth metal hydroxides, alkali metal alcoholates, the alkali metal salts of dicyandiamide, the alkaline earth metal salts of dicyandiamide, amines and ammonia. They can be used either singly or in combination. Although no particular limitation is imposed on the amount of such a catalyst, it can be added in an amount of 500–0.001 mole %, preferably 300–0.1 mole % based on the dicarbonitrile from the viewpoint of preparation conditions and economy. The amount of the catalyst can be chosen suitably as needed.

In the above process for the preparation of the diguanamine, it is extremely practical to conduct the process while using one of various solvent as a reaction solvent in order to perform the reaction more smoothly. It is however not preferred to use any solvent which may induce the formation of a compound other than the target compound or may cause an inhibition on the reaction, for example, a solvent such as a fatty acid, a fatty acid anhydride, trifluoroacetic acid, liquid sulfur dioxide, sulfuryl chloride, a mineral acid or water.

Illustrative of the reaction solvent include alcohols such as methanol, ethanol, n-propanol, isopropanol, n-butanol, iso-butanol, tert-butanol, 2-ethylhexanol, dodecyl alcohol, allyl alcohol, propargyl alcohol, benzyl alcohol, cyclohexanol, ethylene glycol, butanediol, glycerin, 1,2,6-hexanetriol, 2-methoxyethanol, 2-ethoxyethanol, 2-isopropoxyethanol, 2-butoxyethanol, furfuryl alcohol, tetrahydrofurfuryl alcohol, diethylene glycol, diethylene glycol monomethyl ether, diethylene glycol monobutyl ether, 1-methoxy-2-propanol, 1-ethoxy-2-propanol, dipropylene glycol, diacetone alcohol, 2,2,2-trifluoroethanol and 1,3-dichloro-2-propanol; ketones such as acetone, methyl ethyl ketone, methyl isobutyl ketone and acetophenone; esters such as ethyl acetate, butyl acetate and benzyl acetate; ethers such as diethyl ether, ethylene glycol dimethyl ether, diethylene glycol dimethyl ether, tetrahydrofuran, dioxane, crown ethers and anisol; carboxylic acid amides such as N,N-dimethylformamide, N,N-diethylformamide, N,N-dimethylacetamide, N-methylpyrrolidone and 1,3-dimethyl-2-imidazolidinone; sulfolanes such as sulfolane, methylsulfolane and 1,3-propanesultone; sulfoxides such as dimethyl sulfoxide; amines such as methylamine, dimethylamine, trimethylamine, ethylamine, diethylamine, triethylamine, isopropylamine, butylamine, 2-ethylhexylamine, allylamine, aniline, cyclohexylamine, pyridine, piperidine, monoethanolamine, 2-(dimethylamino)ethanol, diethanolamine, triethanolamine, isopropanolamine and triisopropanolamine; and ammonia. Particularly preferred are non-aqueous protonic solvents such as alcohols, amines and ammonia and aprotonic polar solvents such as carboxylic acid amides, sulfolanes and sulfoxides. These solvents can be used either singly or as mixed systems consisting of two or more of them like mixed solvents such as ammonia-alcohol and dimethylsulfoxide-cellosolve. They can be chosen suitably as needed. Such solvents preferably have a water content as low as possible, notably a water content of 1.0 wt. % or less.

Reaction temperatures not higher than 60° C. are not preferred, because the reaction is extremely slow so that a long time is required for the preparation and the yield is very low. When the reaction is conducted generally at a temperature of 60° C. or higher, preferably at a temperature of 80° C. or higher, the reaction proceeds promptly and smoothly so that the target compound can be obtained in a high yield. However, if the reaction temperature exceeds about 200° C., the formation of byproducts suddenly increases to such an extent that these byproducts can no longer be ignored, and the purity of the product is lowered considerably. Reaction temperatures above 200° C. are therefore not preferred. In the process of this invention for the preparation of the diguanamine, it is therefore preferred to conduct the reaction in a temperature range of 60°–200° C., more preferably 80°–180° C. In such a temperature range, byproducts are minimized and the target compound can be obtained with high purity, the preparation including the purification can be performed easily, and the target compound can be obtained in a higher yield.

Although no particular limitation is imposed on the reaction system, the reaction can be carried out either under normal pressure or under naturally-occurring pressure or elevated pressure in a closed vessel. The reaction system can be suitably selected as needed.

To obtain the diguanamine of the present invention, that is, the target compound from the reaction mixture of the above reaction, it is most desirable to cool the reaction mixture and collect the crystallized diguanamine by filtration. As an alternative, the reaction mixture may be poured, as is, into hot water, followed by crystallization and filtration. Unreacted dicyandiamide and/or dicarbonitrile, which accompany with the crude diguanamine, can be easily removed by washing the crude diguanamine with hot water or methanol. When further purification is required depending on the application purpose, the diguanamine can be purified further by subjecting to recrystallization in the above-described reaction solvent, for example, an alcohol, cellosolve, carboxylic acid amide, sulfolane or sulfoxide, a mixed solvent of such a solvent and water, or water; by dissolving it in the above-described reaction solvent and then pouring the resultant solution in hot water, thereby effecting reprecipitation; or by dissolving the crude diguanamine in an HCl-acidified aqueous solution and mixing the resulting solution with an alkali, thereby reprecipitating the diguanamine. Such additional purification is however not required practically in most instances, because the yield is extremely good in the process of this invention for the preparation of the diguanamine and, moreover, the diguanamine can be obtained with high purity sufficient for practical applications when washed simply with one of various solvents such as methanol, water, a mixed solvent thereof or the like.

The diguanamine according to the present invention has excellent polymerizability with various compounds such as aldehydes, epoxy compounds, carboxylic acids and isocyanates and also has various excellent reactivity, so that the diguanamine is extremely useful as a raw material for resins and also as a raw material for derivatives. Moreover, diguanamine derivatives such as reaction products of the diguanamine with aldehydes, reaction products obtained by etherifying the first-mentioned reaction products with alcohols, and reaction products obtained by subjecting the first-mentioned and second-mentioned reaction products to condensation are particularly useful as curing agents and raw materials for various resins.

Such diguanamine derivatives include, for example, the above-described derivatives:

(f) N-methylol diguanamine obtained by subjecting the diguanamine described under (a) and an aldehyde to an addition reaction and represented by the following formula (5) or (6):

Formula (5)

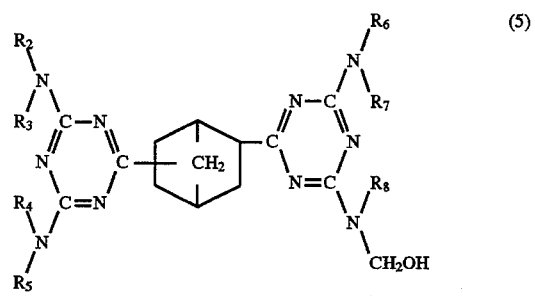

wherein the bonding sites of the N-substituted-4,6-diamino-1,3,5-triazin-2-yl groups are the 2,5- or 2,6-positions, $R_2$, $R_3$, $R_4$, $R_5$, $R_6$, $R_7$ and $R_8$ individually represent one substituent selected from a hydrogen atom and an $HOCH_2$ group, and $R_2$, $R_3$, $R_4$, $R_5$, $R_6$, $R_7$ and $R_8$ may be the same or different, or Formula (6)

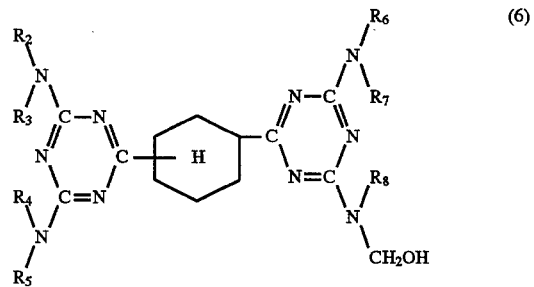

wherein the bonding sites of the N-substituted-4,6-diamino-1,3,5-triazin-2-yl groups are the 1,2-, 1,3- or 1,4-positions, $R_2$, $R_3$, $R_4$, $R_5$, $R_6$, $R_7$ and $R_8$ have the same meaning as defined above, and $R_2$, $R_3$, $R_4$, $R_5$, $R_6$, $R_7$ and $R_8$ may be the same or different;

(g) etherified diguanamines each obtained by etherifying the N-methylol diguanamine described above under (f) with at least one alcohol selected from the group consisting of alcohols having 1–20 carbon atoms, containing at least one $R_1OCH_2$ group, $R_1$ representing a residual group formed by removing a hydroxyl group from the alcohol, and represented by the following formula (7) or (8):

Formula (7)

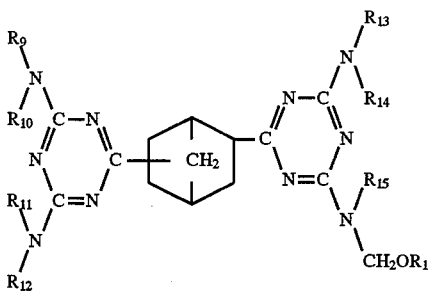

wherein the bonding sites of the N-substituted-4,6-diamino-1,3,5-triazin-2-yl groups are the 2,5- or 2,6-positions, $R_1$ represents a residual group formed by removing a hydroxyl group from the alcohol, $R_9$, $R_{10}$, $R_{11}$, $R_{12}$, $R_{13}$, $R_{14}$ and $R_{15}$ individually represent one substituent selected from a hydrogen atom and $HOCH_2$ and $R_1OCH_2$ groups, and $R_9$, $R_{10}$, $R_{11}$, $R_{12}$, $R_{13}$, $R_{14}$ and $R_{15}$ may be the same or different, or Formula (8)

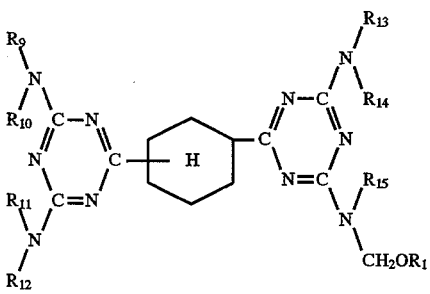

wherein the bonding sites of the N-substituted-4,6-diamino-1,3,5-triazin-2-yl groups are the 1,2-, 1,3- or 1,4-positions, $R_1$ represents a residual group formed by removing a hydroxyl group from the alcohol, $R_9$, $R_{10}$, $R_{11}$, $R_{12}$, $R_{13}$, $R_{14}$ and $R_{15}$ have the same meaning as defined above, and $R_9$, $R_{10}$, $R_{11}$, $R_{12}$, $R_{13}$, $R_{14}$ and $R_{15}$ may be the same or different;

(h) primary condensates of the N-methylol diguanamine each obtained by subjecting the diguanamine described above under (a), a condensable compound as an optional reactant and an aldehyde to an addition condensation reaction, having an average addition condensation degree greater than 1 and containing at least one methylol group; and (i) primary condensates of the etherified diguanamine each obtained by subjecting the diguanamine described above under (a), a condensable compound as an optional reactant and an aldehyde to an addition reaction or an addition condensation reaction and then etherifying the reaction product with at least one alcohol selected from the group consisting of alcohols having 1–20 carbon atoms and optionally to a simultaneous condensation reaction, having an average addition condensation degree greater than 1 and containing at least one $R_1OCH_2$ group, $R_1$ having the same meaning as defined above.

Examples of the aldehydes used for the preparation of these derivatives include, but are not limited to, formaldehyde, paraformaldehyde, hexamethylenetetramine, methylhemiformal, butylhemiformal, formaldehyde-sodium bisulfite addition product, and glyoxal. Preferred are formaldehyde, formalin, paraformaldehyde, hexamethylenetetramine, methylhemiformal and butylhemiformal, Useful as the alcohols employed for the etherification in the preparation of these derivatives are alcohols such as saturated or unsaturated aliphatic alcohols having 1–20 carbon atoms, alicyclic alcohols, alcohols containing one or more ether groups, and alcohols containing one or more aromatic groups. Examples of such alcohols include, but are not limited to, methyl alcohol, ethyl alcohol, n-propyl alcohol, isopropyl alcohol, n-butyl alcohol, isobutyl alcohol, tert-alcohol, n-hexyl alcohol, sec-heptyl alcohol, 2-ethylhexyl alcohol, n-nonyl alcohol, n-hexadecyl alcohol, n-octadecyl alcohol, n-eicosyl alcohol, cyclohexyl alcohol, cyclohexenyl alcohol, 4-methylhexyl alcohol, 4-hexylcyclohexyl alcohol, ethylene glycol monomethyl ether, ethylene glycol monobutyl ether, propylene glycol monoisopropyl ether, diethylene glycol monomethyl ether, and benzyl alcohol.

In the preparation of these derivatives, co-condensable compounds can be used in some instances as described above. Examples of such co-condensable compounds include, but are not limited to, melamine, urea, alkylureas, thiourea, alkylthioureas, aniline, and guanamines such as benzoguanamine and cyclohexylcarboguanamine.

In the case of the N-methylol diguanamine described above, the reaction proceeds promptly and smoothly to provide the derivative with at least one $HOCH_2$ group when the reaction is conducted, for example, in a solvent and, if necessary, in the presence of a basic compound, at pH 8.0–13.0, preferably pH 8.5–11.5 and a reaction temperature of not lower than 30° C., preferably 40°–80° C. To obtain an N-methylol diguanamine with a high degree of methylol derivation, the derivative can be obtained with high purity and in a high yield when the reaction is conducted using water and the alcohol in smaller amounts. Use of water and the alcohol in appropriate amounts, however, leads to a reduction in the stirring effects, unevenness in the reaction temperature, etc., thereby making it difficult to smoothly proceeding with the reaction. It is hence not preferred to reduce the amounts of water and the alcohol. To allow the reaction to proceed smoothly, it is effective to conduct the reaction in the presence of a solvent substantially insoluble in water and free from inhibition to the reaction, for example, an aromatic hydrocarbon such as toluene, xylene, ethylbenzene, cumene or benzene, an aliphatic hydrocarbon such as hexane, heptane, octane or cyclohexane, a halogenated hydrocarbon such as dichloromethane or a aliphatic ether such as diisopropyl ether; or to add an amine as an aid, for example, an aliphatic amine such as hexamethylenetetramine, piperazine or piperidine, an aliphatic amine such as triethylamine, diethylamine, dibutylamine or hexylamine, an aromatic amine such as pyridine or aniline, or ammonia in an amount of 0.01–10 mole % based on the aldehyde. The reaction can be performed by suitably choosing these methods as needed. It is however to be noted that the practice of the reaction is not necessarily limited to the use of such methods.

The etherified diguanamine described above can be obtained, for example, by reacting the above-obtained N-methylol diguanamine for 1–8 hours under acidic conditions of pH 2–4 at a temperature of 40°–80° C. in the presence of the alcohol with which an etherification reaction is to be conducted. It is particularly preferred to conduct the etherification by reducing the amount of water in the reaction system as much as possible and charging the reactants at a ratio of at least 20 moles of the alcohol to each mole of the N-methylol diguanamine.

The primary condensate of N-methylol diguanamine described above can be obtained, for example, by reacting with the aldehyde at a temperature of 40°–100° C. under conditions of pH 8.0 or lower or pH 13.0 or higher.

Further, the primary condensate of etherified diguanamine can be obtained, for example by subjecting the N-methylol diguanamine or the primary condensate of N-methylol diguanamine to etherification or to both etherification and condensation under acidic conditions of pH 1.0–5.0 at a temperature of 50°–100° C. in the presence of the alcohol with which an etherification reaction is to be conducted. It is however to be noted that the preparation process is not limited to that described above.

The N-methylol diguanamine, etherified diguanamine, primary condensate of N-methylol diguanamine and primary condensate of etherified diguanamine have excellent reactivity with compounds and resins having various kinds of functional groups and are extremely useful as curing agents for various resins and also as intermediates for resin raw materials. For example, it is possible to provide a thermosetting composition which comprises at least one derivative selected from the group consisting of the derivatives (f), (g), (h) and (i). Although such compositions are useful as adhesives, crease resistant finishing agents for fibers, for example, synthetic fibers such as polyester fibers and acrylic fibers and natural fibers such as cotton and wool, excellent surface improving agents for antifouling agents, paper coating agents and hide treatments even if these derivatives alone are contained as curing components, these diguanamine derivatives can be reacted further with those containing one or more hydroxyl, carboxyl, isocyanate and/or epoxy groups so that resins having excellent properties can be obtained. In combination with various polymers such as acrylic resins, epoxy resins, polyester resins, urethane resins, aminoalkyd resins, phenol resins, fluorinated resins and vinyl resins, the above derivatives can provide thermosetting compositions extremely useful as chain extenders, crosslinking agents, curing agents, denature agents and/or modifiers. They are accordingly useful for a wide variety of application fields, for example, as adhesive resins, paint resins and building resins. Especially, thermosetting compositions comprising at least one derivative, which is selected from the group consisting of the N-methylol diguanamines, etherified diguanamines, primary condensates of the N-methylol diguanamines and primary condensates of the etherified diguanamines, and a resin curable through a reaction with the derivative are useful as resins for paints such as water-base paints and oil-base paints.

The resin curable through a reaction with such a derivative can be any resin having functional groups capable of reacting with the derivative so that the resin is cured. For example, resins containing at least one type of groups selected from hydroxyl groups, carboxyl groups, epoxy groups, methylolamido groups, alkoxymethylolamido groups and isocyanate groups are useful. Examples of such resins include, but are not limited to, acrylic resins, epoxy resins, polyester resins, phenol resins, phenol-alkyd resins, urethane resins, fluorinated resins, silicone resins, and modified resins thereof.

The diguanamines according to the present invention can provide thermosetting resin compositions which comprise, as essential components, at least one diguanamine selected from the diguanamines described above and an epoxy-containing resin. A conventional composition comprising an epoxy-containing resin and an amine as a curing agent cures at relatively low temperatures but, because the amine used as a curing agent is chemically active, the amine reacts with the epoxy-containing resin when they are stored as a mixture. This has resulted in the drawback that the composition has a shorter pot life and its handling is difficult. A composition containing dicyandiamide as a curing agent has relatively good storage stability, but articles obtained by curing the composition are accompanied by the drawbacks that their properties such as flexibility and light resistance are not good. Considerable limitations are therefore imposed on the use of such compositions. With these drawbacks in view, the present inventors have proceeded with an extensive investigation. As a result, they have found the above-described thermosetting resin compositions which have excellent storage stability and can provide cured resin articles having excellent properties as cured products such as excellent flexibility and light resistance. These thermosetting resin compositions are useful for a wide variety of applications, for example, as IC packaging materials, adhesives, powder coatings, oil-base paints, electric insulating materials and the like.

Any epoxy-containing resin can be used widely in this invention insofar as it contains at least one epoxy group. In general, a polyepoxide containing at least two epoxy groups per molecule is preferred. Although no particular limitations are imposed on the epoxy-containing resins, illustrative exemplary epoxy-containing resins include, but are not limited to, diglycidyl ether type epoxy resins of bisphenol A; butadiene epoxide; 4,4-di(1,2-epoxyethyl)diphenyl ether; 4,4'-di(epoxyethyl)biphenyl, diglycidyl ether of resorsine; diglycidyl ether of fluoroglycine; triglycidyl ether of p-aminophenol; triglycidyl ether of m-aminophenol; tetraglycidyl-bis-(aminophenol)methane; 1,3,5-tri(1,2-epoxyethyl)benzene; 2,2,4,4-tetraglycidoxybenzophenone; tetraglycidoxytetraphenylethane; polyglycidyl ethers of novolak phenol-formaldehyde resins; triglycidyl ether of trimethylolpropane; triglycidyl ether of glycerin; diglycidyl ether type epoxy resins of halogenated bisphenol A; polyglycidyl ethers of halogenated novolak phenol-formaldehyde resins; cycloaliphatic epoxy resins such as vinylcyclohexene dioxide and 3,4-epoxycyclohexylmethyl 3,4-epoxycyclohexanecarboxylate; heterocyclic epoxy resins such as hydantoin epoxy resin and triglycidyl isocyanurate; polymers of epoxy-containing vinyl monomers, such as glycidyl acrylate and glycidyl methacrylate, with copolymerizable vinyl monomers such as acrylate esters, methacrylate esters, fumarate esters, maleate esters, acrylamides, methacrylamides, acrylonitrile, methacrylonitrile, styrenes, butadienes and vinyl esters; and modified polymers thereof.

Where a high-molecular, bisphenol A-diglycidyl ether type epoxy resin cannot be used for its high viscosity in the present invention, the resin can be modified using as a modifier such as a low-molecular bisphenol A-glycidyl ether type epoxy resin, bisphenol A, bisphenol S, brominated bisphenol A or brominated bisphenol S.

The mixing ratio of the diguanamine according to this invention to the epoxy-containing resin can be suitably selected depending on the application. In general, however, the diguanamine is used in an amount of 0.2–3.0 equivalents, preferably 0.4–1.5 equivalents per equivalent of epoxy groups in the epoxy-containing resin.

For each thermosetting resin composition according to the present invention, a curing accelerator such as a novolak type phenol resin, a metal salt of an organic acid or imidazole can be suitably chosen and mixed. Use of such a curing accelerator is preferred especially where a novolak type phenol resin is used, because a thermosetting resin composition excellent in storage stability and curability can be obtained. Examples of the novolak type phenol resin include, but are not limited to, those produced by a process known per se in the art from a phenol such as phenol, cresol, xylenol, ethylphenol, butylphenol, p-phenylphenol, nonylphenol, bisphenol A, resorcinol or chlorophenol and an aldehyde such as formaldehyde or paraformaldehyde. Although the mixing proportion of the novolak type phenol resin is generally 0.1–10 parts by weight per 100 parts by weight of the epoxy-containing resin, it can be suitably chosen as needed.

The thermosetting resin compositions according to the present invention can each be obtained by mechanically mixing a raw material batch, which is composed of the diguanamine, the epoxy-containing resin and, if necessary, other optional components in prescribed mixing proportions, within a Z-blade mixer, extruder, dry ball mill or the like to a sufficient extent. Further, the mixture so obtained can be subjected to melt mixing by hot rolls or the like in some instances. The diguanamine according to the present invention, however, has a high melting point so that the mixture may not flow evenly or the resulting cured article may not be homogeneous. Even when such melt mixing is not preferred, a thermosetting resin composition in a fully compatibilized form can still be obtained, for example, by heating, melting and mixing the diguanamine in advance together with a low-viscosity diluent, a solbilizing agent, a novolak type phenol resin, etc., adding an epoxy-containing resin to the resultant melt and then mixing them under heat, by dissolving and mixing the guanamine and the epoxy-containing resin in a solvent, or by removing the solvent from the mixed solution. These methods can be suitably chosen as needed. It is to be noted that the present invention is not necessarily limited to any of these methods.

Besides the diguanamine and epoxy-containing resin described above, each thermosetting resin composition according to the present invention can be added, as needed, with an inorganic filler, for example, silica powder, alumina, antimony trioxide, talc, calcium carbonate, titanium white, clay, mica, red oxide, glass fibers or carbon fibers; a mold release agent such as a natural wax, a synthetic wax, a metal salt of a fatty acid, an acid amide, an ester or a paraffin; a flame retardant such as chlorinated paraffin, bromotoluene, hexabromobenzene or antimony trioxide; a colorant such as carbon black or red oxide; a silane coupling agent; a flexibilizer; a viscosity-reducing diluent; one or more of various curing accelerators; etc.

Each diguanamine according to the present invention can provide compounds and resins such as polyamic acids, polyimides and polyamides, all having excellent properties, when reacted with carboxylic acids, for example, phthalic acid, adipic acid, maleic acid, trimellitic acid, ethylenetetracarboxylic acid, cyclopentanetetracarboxylic acid, pyrromellitic acid, 3,3',4,4'-benzophenonetetracarboxylic acid, 2,2',3,3'-benzophenonetetracarboxylic acid, 3,3',4,4'-biphenyltetracarboxylic acid, 2,2',3,3'-biphenyltetracarboxylic acid, 2,2-bis(3,4-dicarboxyphenyl)propane, bis(2,3-dicarboxyphenyl)methane, 2,3,6,7-naphthalenetetracarboxylic acid, 1,4,5,8-naphthalenetetracarboxylic acid, 1,2,5,6-naphthalenetetracarboxylic acid, 1,2,3,4-benzenetetracarboxylic acid, 2,3,6,7-anthracenetetracarboxylic acid and 1,2,7,8-phenanthrenetetracarboxylic acid; or with their precursors, i.e., partial cesters, acid anhydrides, halogenoacylates and the like. Further, each diguanamine according to the present invention can provide compounds and resins such as polyurea, all having excellent properties, when reacted with isocyanates, for example, 1,6-hexamethylene diisocyanate, 2,2,4-trimethylhexamethylene diisocyanate, diisocyanates derived from dimeric acids, bis(2-isocyanatoethyl) fumarate, methylcyclohexane-2,4-diisocyanate, isophorone diisocyanate, 4,4'-dicyclohexylmethane diisocyanate, isopropylidene bis(4-cyclohexylisocyanate), xylylene diisocyanate, m-phenylene diisocyanate, tolidine diisocyanate, dianisidine diisocyanate, 3,3'-dimethyl-4,4'-diphenylmethane diisocyanate, 1,5-naphthalene diisocyanate, 2,4-tolylene diisocyanate, 2,6-tolylene diisocyanate and the like, or with polyisocyanates which have been obtained by reacting such isocyanates with polyols, amines, water or the like. In addition, each diguanamine according to the present invention can also provide resins having excellent properties when reacted with compounds containing one or more N-substituted unsaturated imido groups, for example, with monophenylmaleimide, monophenylcitraconimide, monophenylitaconimide, 2-chlorophenylmaleimide, 2,6-dichlorophenylmaleimide, 2-methylphenylmaleimide, 2,6-dimethylphenylmaleimide, 4-hydroxyphenylmaleimide, N,N'-ethylenebismaleimide, N,N'-hexamethylenebismaleimide, N,N'-dodecanemethylenebismaleimide, N,N'-m-phenylenebismaleimide, N,N'-p-phenylenebismaleimide, N,N'-p-phenylenebiscitraconimide, N,N'-p-phenylenebisitaconimide, N,N'-p-phenylene-endomethylenetetrahydrophthalimide, N,N'-4,4'-diphenylmethanebismaleimide, 2,2-bis[4-(4-maleimidophenoxy)phenyl]propane, N,N'-4,4'-dicyclohexylmethanebismaleimide, N,N'-m-xylenebismaleimide, N,N'-diphenylcyclohexanebismaleimide, 4,4'-bismaleimidocinnamanilide, 4,4'-methylene-bis(2-isopropyl-6-methyl-phenylmaleimide) and 2,2-bis[4-(4-maleimidophenoxy)phenyl]hexafluoropropane. Further, each diguanamine according to the present invention can also be used as metallic chain extenders, crosslinking agents, curing agents, high-molecular modifiers and the like, which have excellent properties, for various polymers such as urethane resins and epoxy resins. It is however to be noted that the use of each diguanamine is not limited to them.

As has been described above, the diguanamines according to the present invention have excellent reactivity and polymerizability with various compounds. Such polymerizations, reactions and the like can be conducted by any polymerization or reaction process such as solution polymerization, emulsion polymerization, suspension polymerization, bulk polymerization, interfacial polymerization, solution reaction or water-system reaction. A suitable polymerization or reaction process can be chosen as needed.

The diguanamines according to the present invention have specific inherent properties such that they are excellent in weatherability, ultraviolet light resistance and the like and can retain initial performance outdoors over a long time, their methylol derivatives are extremely good in water reducibility and have excellent properties as raw materials for water-base resins without any substantial limitation, they contain active amino groups having extremely good reactivity with aldehydes, epoxy compounds, carboxylic acids, isocyanates and the like, and owing to the inclusion of eight active hydrogen atoms, permit the selection of a methylol derivation degree from a wide range. Moreover, they can provide various guanamine derivatives and resins having excellent properties such as flexibility, toughness, high hardness, waterproofness and curability and can show superb performance, so that they are extremely useful compounds.

When the specific compounds described above are used and the reaction catalyst, solvent, reaction temperature, the molar ratio of the raw materials and the like are suitably selected, the process of the present invention for the preparation of the diguanamine can obtain the target product with high purity while substantially minimizing byproducts. The preparation process including the purification step is simple, can substantially reduce the loss of the raw materials, can obtain the target product in a high yield from the raw materials available economically, and therefore is excellent in technology and economy and has extremely high practical utility.

Such diguanamines have excellent polymerizability with various compounds such as aldehydes, epoxy compounds, carboxylic acids and isocyanates and also have various superb reactivity. They are hence extremely useful as raw materials for resins and derivatives. They can provide, for example, derivatives extremely useful as curing agents for various resins and also as intermediates for resin raw materials, such as N-methylol diguanamines obtained by reacting the diguanamines with aldehyde, etherified diguanamines obtained by subjecting the N-methylol diguanamine derivatives and alcohols to etherification, and their initial condensates; thermosetting compositions comprising these derivatives; and thermosetting resin compositions comprising the above diguanamines and epoxy-containing resins, said compositions being useful as IC packaging material resins, paint resins and adhesive resins.

The diguanamines according to the present invention are excellent compounds capable of providing guanamine derivatives, resins and compositions, which are industrially useful in an extremely wide range of fields as rubber modifiers, optical materials, resist materials, electrical insulating materials, paints for home electric and electronic appliances, automotive paints, antifouling paints, anticorrosion paints, weatherable paints, fluorescent paints, powder coatings, water-base paints, oil-base paints, building materials, IC packaging materials, paper coating agents, fiber treatments for antifouling treatment of interior items such as curtains, sofas, wall cloths and carpets and also for water vapor barrier treatment, sweat absorption treatment, SP treatment, wrinkle resistance treatment, water- and oil-repellant treatment of fibers, adhesive resins, hide treatments, plastic magnets, latex antioxidants, anticorrosion agents, electrophotographic photoconductors, surfactants, agricultural chemicals, medicines, and the like.

SECOND INVENTION GROUP

TECHNICAL FIELD

This invention relates to modification of resin raw materials, resins and rubbers—such as polymerizable monomers, polyurethane resins, polyester resins, amino resins, paint resins, adhesive resins, paper coating resins, fiber processing resins, foaming resins, molding resins and laminates, and specifically to diguanamines and their derivatives and polymeric microspheres, which are useful as flame retardants, heat stabilizers, compatibility improvers or the like for resins. This invention is also concerned with applications of such flame retardants, heat stabilizers and compatibility improvers.

BACKGROUND ART

In general, resins have excellent properties such as high strength, chemical resistance, abrasion resistance, weatherability, durability and dyeability and, as molded, extruded or—otherwise formed resin products, are employed in a wide range of industrial fields such as construction material industry, electrical material industry, vehicle, e.g., automotive vehicle material industry, fiber material industry and utensil industry.

These resins are however accompanied by the drawback that they are extremely flammable. Keeping step with their extensive use, there is the significantly increasing tendency that they become a predominant cause in fires. A high standard has hence been imposed on the safety of these industrial materials. It is therefore desired to improve these resins' properties such as flame retardancy and heat resistance.

Further, these resins also tend to undergo deterioration under heat, light or the like. It is therefore desired to improve the thermal stability of the resins and also to improve or impart other properties without impairing the inherent good properties of these resins. It is an extremely important assignment to the industry to modify such resins and also to develop new materials.

Flame retardancy:

With a view to improving the flame retardancy of such resins, a variety of methods has been proposed to date. Known methods include, for example, addition of a flame retardant, mixing with a flame-retardant resin, use of a flame-retardancy-imparting material (monomer) upon production of a resin to incorporate the material in the skeleton of the resin, and application of post treatment to a resin to impart flame retardancy. Among these methods, it is generally often practiced to add a flame retardant to a resin. Known examples of such a flame retardant include halogen-containing compounds, phosphorus-containing compounds, inorganic compounds and nitrogen-containing compounds.

Of these known flame retardants, use of a halogen-containing compound generally results in poor heat resistance. Halogen-containing flame retardants are accompanied by such drawbacks that they are prone to sublimation, bleeding and/or the like, can hardly exhibit their effects in many instances unless used in combination with antimony trioxide, and give off an extremely noxious halogen-containing gas in a large volume in a fire. Use of a phosphorus-containing compound involves such defects that its effects are small when used singly, it can hardly exhibit effects for certain types of resins, and it is often used in combination with a halogen-containing compound to develop the above-described drawbacks of the halogen-containing compound. Use of an inorganic compound, on the other hand, is accompanied by the drawbacks that it may be a rare natural resource like antimony trioxide and hence involves problems in availability, price and the like or that it may not show significant effects like aluminum hydroxide and must hence be added in a large amount, thereby developing problems such as an increase in specific gravity, reductions in physical properties and formability and, due to water contained therein, a deterioration in heat resistance. Further, use of a nitrogen-containing compound involves problems such that, as typified by the melamine type, it is susceptible to sublimation, bleeding and the like, its flame-retarding effects are small due to sublimation or the like when heated, and its price is high due to difficulties in production. The flame-retarding method for resins, in which one or more of these known flame retardants are incorporated, is still insufficient for practical use, and substantial limitations are imposed thereon both technically and economically.

With a view to overcoming the above-described drawbacks or problems in such flame-retarding methods for resins, the present inventors have conducted an extensive investigation. As a result, it has been found that the flame retardancy of such resins can be substantially improved by incorporating therein one or more of particular novel diguanamines different in structure and properties from the conventionally known compounds. It has also been found that these diguanamines have better heat resistance than melamines, sublimation, bleeding and/or the like is not observed, formation of char is excellent, and sagging or dripping of oil droplets or melt is substantially minimized, thereby making it possible to provide an excellent method for making resins retardant to flame. Further, it has also been found that combined use of one or more of the above-described diguanamines with phosphoruses, isocyanuric acids, cyanuric acids or amino-containing compounds can provide a flame-retarding method for resins, which can impart still improved flame retardancy to the resins. These findings have led to the present invention.

Heat Stabilization

Further, such resins are prone to embrittlement and/or coloration upon application of heat, light or another external energy thereto and/or in the presence of oxygen or a heavy metal. This problem has therefore imposed limitations on their use in a wide variety of fields despite their excellent properties. With a view to improving the above problems, various proposals have been made to date. These proposals, however, are still insufficient to overcome these problems. In some extreme cases, the inherent excellent properties of resins are lost. Such proposals are therefore by no means suited for practical use.

As a specific example of such conventional thermal stabilization methods, there is disclosed a method for thermally stabilizing a resin by incorporating, for example, a thermal stabilizer such as a benzoate, amine, arylphosphonic diamide or organic phosphite. To impart practically satisfactory stability to heat, light and the like, no method has however been developed yet.

It is also known to thermally stabilize a resin by incorporating therein melamine, acetoguanamine, benzoguanamine or the like. This method is however accompanied by the drawbacks that it shows no specific effect on the improvement of stability to heat, light and the like and is unable to bring about any sufficient effects from the practical viewpoint.

Known thermal stabilization methods for resins also include incorporation of phthaloguanamine, spiroguanamine or the like. This method is however accompanied by problems such that these compounds are inferior in ultraviolet light resistance, weatherability and the like and undergo substantial discoloration or the like and, when molded or otherwise formed at high temperatures, resins are substantially colored or discolored, the resultant resins do not have sufficient thermal stability, and such thermal stabilizers themselves are subjected to thermal decomposition during processing, molding and the like. These thermal stabilization methods for resins are accordingly insufficient for practical use and are accompanied by substantial limitations in both technology and economy.

In view of the above-described drawbacks or problems of such thermal stabilization methods for resins, the present inventors have proceeded with an extensive investigation. As a result, it has been found that incorporation of a specific novel diguanamine different in structure and properties from the above-described compounds in a resin can significantly improve its ultraviolet light resistance, weatherability and thermal stability, can minimize coloration or discoloration when performing processing, molding or the like at high temperatures, and can reduce deterioration even during use for a long time at relatively high temperatures. It has also been found the thermal stabilizer itself is resistant to decomposition even at high temperatures can hence provide a thermal stabilization method for the provision of a resin excellent in handling ease and the maintenance of properties. These findings have led to the present invention.

Compatibilization

In addition, such resins have excellent properties and are used in a wide variety of industrial fields. As methods for improving various properties of such resins or modifying such resins to impart a new property thereto without impairing their inherent good properties, various polymer alloying methods have been proposed.

As such polymer alloying methods for resins, it has conventionally been proposed, for example, to modify the resins themselves or to add a third component such as a compatibilizing agent to them. However, substantial technical and/or economical limitations are imposed on the former method because of the need for a difficult reaction and cumbersome steps for the modification of each resin, reductions in properties such as a molecular weight reduction of the resin upon modification, etc. The latter method, on the other hand, is accompanied by drawbacks such that properties of each resin, such as heat resistance, weatherability and water resistance, are reduced by the inclusion of the third component, preparation of the compatibilizing agent requires a complex process, and high production cost is needed.

With a view to overcoming the above-described drawbacks or problems of such compatibilization methods for resins, the present inventors have conducted with an extensive investigation. As a result, it has been found that incorporation of a particular novel diguanamine, which is different in structure and properties from conventionally known compounds, in a blend of two or more resins can provide a compatibilization method for resins. According to the compatibilization method, excellent compatibilization can be achieved between different kinds of resins, and the resin so obtained has superb melt properties and excellent heat resistance, weatherability and water resistance. Moreover, the compatibilizing agent can be easily produced. The compatibilization method also benefits low production cost. The above finding has led to the present invention.

Diguanamine Derivative

Further, this invention also provides a diguanamine derivative, which is an N-substituted derivative of the above-described diguanamine, its preparation process and its application.

N-substituted melamines available from melamine, benzoguanamine and the like are known. Their preparation processes are also known. Such N-substituted melamines include various hydroxyl-containing melamine derivatives which have been provided for the usefulness. Known examples include N-polyoxyalkyl-substituted melamines obtained by an addition reaction of melamine with epoxides as well as N-hydroxyalkyl-substituted melamines obtained by a reaction of melamine with aminoalkanols.

These N-substituted melamines are however accompanied by drawbacks such that they cannot impart practically sufficient flame retardancy, heat resistance and mechanical properties (e.g., flexibility and toughness) when used as resin raw materials, resin modifiers or the like and, because they do not contain many functional groups, they can hardly exhibit sufficient effects as modifiers, chain extenders, curing agents, crosslinking agents or the like.

Further, in the former process for the preparation of an N-polyoxyalkyl-substituted melamine, the yield is extremely low when the reaction is conducted in the absence of a solvent. Even when a solvent such as dimethyl sulfoxide, which has better melamine dissolving ability than other solvents, is used, it is difficult to allow the reaction to smoothly proceed because its melamine dissolving ability is still insufficient even at high temperatures. It is hence difficult to obtain the target product. Instead, products having high molecular weights only are obtained, thereby making it difficult to obtain a product having a desired molecular weight or having a narrow molecular weight distribution. Substantial limitations are therefore imposed on such a reaction product in use, performance and the like. The latter process for the preparation of an N-hydroxyalkyl-substituted melamine, on the other hand, is also accompanied by problems such that, due to insufficient dissolution of the melamine and also the need for conducting the reaction at a high temperature even when the reaction is carried out in the presence of a solvent, an excess amount of an aminoalkanol and the like, the reaction can hardly proceed uniformly and requires a long time for the preparation, a desired product having a narrow molecular weight distribution can hardly be obtained, the reaction product is substantially colored, byproducts are formed in large amounts, and the purification and isolation become complex.

As has been described above, substantial technical and/or economical limitations are imposed on the known N-substituted melamines upon use and preparation.

With a view to overcoming the above-described drawbacks or problems of such N-substituted melamines, the present inventors have conducted an extensive investigation. As a result, the present inventors have found diguanamine derivatives excellent in properties such as heat resistance, flame retardancy, weatherability, flexibility and toughness and different in structure and properties from the conventional compounds as well as novel hydroxyl-containing or oxalkyl-containing diguanamine derivatives which contain one or more active hydroxyl or imino groups or the like capable of showing excellent reactivity to compounds containing various functional groups and permit selection of the number of functional group(s) from a wide range up to those containing 8 active hydrogen atoms, leading to the present invention.

Further, the present inventors have found an excellent process for the preparation of such diguanamine derivatives. According to the process, upon preparation of a diguanamine derivative, the target reaction product can be easily obtained in a high yield by reaction of a novel diguanamine different in structure and properties from the conventional compounds with an amine HO—$Y_9$—$NH_2Y_9$, $R_9$ being a divalent group containing at least two carbon atoms or by reaction of the above-described diguanamine, a hydroxyl-containing diguanamine derivative and an epoxide.

It has also been found that incorporation of the above-described diguanamine derivative can provide an excellent method for making the resin retardant to flame. The diguanamine derivative has better heat resistance than melamine and the like, so that sublimation, bleeding or the like is not observed. Formation of char is excellent so that sagging or dripping of oil droplets or a melt is significantly minimized. The resulting resin has good melt properties. Further, its combined use with a phosphorus, an isocyanuric acid, cyanuric acid or an amino-containing compound can provide still improved flame retardancy. These findings have led to the present invention.

Moreover, it has also been found that incorporation of the above-described diguanamine derivative and organic polyisocyanate component can provide a polyurethane resin composition which can provide a material excellent in properties such as flame retardancy, heat resistance, water resistance, abrasion resistance and elasticity, leading to the present invention.

Organic Microspheres

There are also known cured organic microspheres obtained by using and curing an amino resin which has been obtained by reacting an amino compound, such as urea, melamine, benzoguanamine or cyclohexanecarboguanamine, with formaldehyde.

Among such cured organic microspheres, those obtained using urea are accompanied by drawbacks such as poor weatherability, especially poor sunlight fastness, unclear color and low impact resistance. Those obtained using melamine, on the other hand, are accompanied by drawbacks such as poor impact resistance. Those obtained using benzoguanamine are excellent in water resistance, but are accompanied by drawbacks such that their weatherability is very poor and they hence undergo substantial discoloration in outdoor use. Further, those obtained using cyclohexanecarboguanamine are excellent in weatherability but are accompanied by drawbacks such that they are still insufficient in heat resistance, impact resistance, abrasion resistance, solvent resistance and the like.

As a method for obtaining cured organic microspheres in a colored form, it is known to color a polymer with a colorant such as a dye or pigment and then to finely grind the polymer so colored. Such a method is accompanied by drawbacks such as difficulties in controlling the sphere size upon fine grinding and high grinding cost. In addition, it is necessary to control the low crosslinking degree and molecular weight of the resin upon production of the resin so that its fine grinding can be facilitated. This however leads to problems such as insufficient impact resistance, solvent resistance and heat resistance.

With a view to overcoming the above-described drawbacks of such cured organic microspheres, the present inventor have carried out an extensive investigation. As a result, it has been found that polymeric microspheres excellent in heat resistance, solvent-resistance, weatherability, impact resistance, abrasion resistance and the like can be furnished by emulsifying an amino resin, which has been obtained by reacting an amino compound with an aldehyde, said amino compound including a novel particular diguanamine different in structure and properties from the above-described compounds, adding a curing agent to the amino resin and then polymerizing the amino resin. It has also been found that polymeric microspheres useful as a resinous colorant excellent in weatherability, color, solvent resistance, impact resistance and the like can be furnished by coloring the amino resins so polymerized. The above findings have led to the present invention.

As has been described above, it is an industrially important assignment to improve the flame retardancy of resins. The present inventors have found that an excellent flame-retarding method can be provided for each resin by incorporating therein novel polymeric microspheres according to the present invention. The novel polymeric microspheres can significantly improve the flame retardancy of the resin. The above-described novel diguanamine is free from sublimation, bleeding or the like. The resin so obtained is excellent in the formation of char so that sagging or dripping of oil droplets or melt can be minimized. Further, production of noxious gas can also be minimized. These findings have led to the present invention.

DISCLOSURE OF THE INVENTION

In one aspect of the present invention, there is thus provided a method for making a resin retardant to flame, which comprises incorporating 3–50 wt. %, based on said resin, of at least one diguanamine selected from diguanamines represented by the formula (1) or by the formula (2).

In another aspect of the present invention, there is also provided a method for thermally stabilizing a resin, which comprises incorporating 0.01–5 wt. %, based on said resin, of at least one diguanamine selected from the diguanamines represented by the formula (1) or (2).

In a further aspect of the present invention, there is also provided a method for making a resin compatible, which comprises incorporating at least one diguanamine, which is selected from the diguanamines represented by the formula (1) or (2), in a blend of at least two resins including at least one resin selected from polyamide resins, polyphenylene ether resin, polyimide resins and polyaramid resins.

In still further aspects of the present invention, there are also provided a diguanamine derivative, a process for the preparation of the diguanamine derivative, and flame-retarding, thermal stabilization and compatibilization methods for a resin, said methods all making use of the diguanamine derivative, as well as polymeric microspheres using the above-described diguanamine and a flame-retarding method for a resin, said method making use of the polymeric microspheres.

BEST MODE FOR CARRYING OUT THE INVENTION

Flame-retarding Method

In the flame-retarding method according to this invention for the resin, the diguanamine can be used in an amount of 3–50 wt. %, preferably 4–40 wt. % based on the resin. Amounts smaller than 3 wt. % can hardly bring about sufficient effects for the improvement of flame retardancy, but amounts greater than 50 wt. % can lead to reductions in physical properties as the resulting compositions can have poor formability or the resin can be deteriorated. Amounts outside the above range are therefore not preferred.

In the above-described flame-retarding method for the resin, use of phosphoruses selected from the group consisting of simple substances of phosphorus and phosphorus-containing compounds in combination with the diguanamine of this invention in the resin is particularly preferred because they can impart the synergistic effect that the flame-retarding effects can be improved further. Such excellent synergistic effects are believed to be produced for their functions not only to facilitate formation of a flame retardant film of relatively low volatility on a burning resin surface but also to further promote formation of char and hence to increase a layer of char so that oxygen can be prevented from spreading to the burning surface, release of flammable gas from the resin portion can be reduced and conduction of heat to the resin portion can be reduced.

Useful examples of such phosphoruses include, but are not limited to, simple substances of phosphorus such as red phosphorus; phosphorus-containing acids such as phosphoric acid, polyphosphoric acids, phosphorous acid, phosphonic acid, phosphate salts, polyphosphate salts, phosphite salts and phosphonate salts; phosphate esters such as phosphoric triesters, polyphosphate esters, acidic phosphate esters, and salts thereof; phosphite esters such as phosphorous triesters and phosphorous diesters; phosphonate esters such as phosphonate esters, acidic phosphonate esters and salts thereof; phosphines such as phosphine, phosphine oxide and phosphonium salts; and sulfur-containing phosphorus compounds such as dialkyl thiophosphates and salts thereof.

Illustrative examples of such phosphorus-containing acids include acids such as phosphoric acid, pyrophosphoric acid, tripolyphosphoric acid, polyphosphoric acid, phosphorous acid and phosphonic acid; and salts available by either partially or fully neutralizing such acids with bases such as ammonia, amines, alkali metals or alkaline earth metals, namely, ammonium phosphate, ethylenediamine phosphate, sodium phosphate, calcium phosphate, melamine pyrophosphate, sodium pyrophosphate, ammonium tripolyphosphate, sodium tripolyphosphate, ammonium polyphosphates, sodium polyphosphates, ammonium phosphite, calcium phosphite and ammonium phosphonate. Of these, ammonium polyphosphates represented by formula $(NH_4)_{n+2}P_nO_{3n+1}$ wherein n stands for an integer greater than 5 are preferred. It is however to be noted that the present invention is not necessarily limited to the use of such illustrative examples.

In the above-described ammonium polyphosphates represented by formula $(NH_4)_{n+2}P_nO_{3n+1}$ wherein n stands for an integer greater than 5, it is preferred to set n at a substantially large value to make water solubility smaller in view of flame retarding effects and the physical properties of the resulting composition. A salt in which n is an integer greater than 50 is particularly preferred. This salt practically corresponds to a metaphosphate, $(NH_4PO_3)_n$.

Examples of such ammonium polyphosphates include "Exolit 263" (trade name; product of Hoechst AG), "Exolit 422" (trade name; product of Hoechst AG) and "Phoscheck P/30" (trade name; product of Monsanto Chemical Company).

Illustrative of such phosphate esters include, but are not to be limited to, phosphoric triesters such as trimethyl phosphate, triethyl phosphate, tri-n-butyl phosphate, trioctyl phosphate, trilauryl phosphate, tricetyl phosphate, tristearyl phosphate trioleyl phosphate, tris(butoxyethyl) phosphate, triphenyl phosphate, tricresyl phosphate, trixylenyl phosphate, cresyl diphenyl phosphate, xylenyl diphenyl phosphate, tris(isopropylphenyl) phosphate, ethyl diphenyl phosphate, isopropyl diphenyl phosphate, n-butyl diphenyl phosphate, 2-ethylhexyl diphenyl phosphate, isodecyl diphenyl phosphate, cetyl diphenyl phosphate, stearyl diphenyl phosphate, oleyl diphenyl phosphate, butyl dicresyl phosphate, octyl dicresyl phosphate, lauryl dicresyl phosphate, diphenyl 2-metacroyloxyethyl phosphate, tris(2-chloroethyl) phosphate, tris(2-chloropropyl) phosphate, tris (2,3-dichloropropyl) phosphate, and tris(2,3-dibromopropyl) phosphate, tris(bromochloropropyl) phosphate, tris(tribromophenyl)phosphate; acidic phosphate esters such as (mono,di)methyl acid phosphate (mixture), (mono,di)ethylacid phosphate mixture, diisopropylacid phosphate, monobutyl acid phosphate, dibutyl acid phosphate, di-2-ethylhexyl phosphate, monoisodecyl acid phosphate, (mono,di) lauryl acid phosphate (mixture), (mono,di)tridecyl acid phosphate (mixture), (mono,di) stearyl acid phosphate (mixture), (mono,di)oleyl acid phosphate (mixture), (mono,di)2-chloroethyl acid phosphate (mixture, (mono,di)butoxyethyl acid phosphate (mixture), ethylene glycol acid phosphate, dibutyl pyrrophosphate, monophenyl acid phosphate, diphenyl acid phosphate, monocresyl acid phosphate, dicresyl acid phosphate, monoxylenyl acid phosphate, and dixylenyl acid phosphate; and ammonia, amine, melamine, alkali metal and alkaline earth metal salts of acidic phosphate esters, such as ammonium dimethyl phosphate, ammonium diethyl phosphate, ammonium ethyl phosphate, ammonium di-n-butyl phosphate, triethanolamine dibutoxyethyl phosphate, morpholine dioctyl phosphate, sodium mono-n-butyl phosphate, ammonium diphenyl phosphate, melamine diphenyl phosphate, piperazine diphenyl phosphate, ammonium phenyl phosphate, ethylenediamine dicresyl phosphate, sodium cresyl phosphate, and melamine dixylenyl phosphate.

Examples of such phosphite esters include, but are not limited to, phosphite triesters such as trimethyl phosphite, triethyl phosphite, tributyl phosphite, tris(2-ethylhexyl) phosphite, tridecyl phosphite, trilauryl phosphite, trioleyl phosphite, tristearyl phosphite, triphenyl phosphite, tris (nonylphenyl) phosphite, tris(2,4-di-t-butylphenyl) phosphide, tris(dinonylphenyl) phosphite, bis(nonylphenyl) dinonylphenyl phosphite, diphenyl mono(2-ethylhexyl) phosphite, diphenyl monodecyl phosphite, diphenyl mono (tridecyl) phosphite, phenyl diisooctyl phosphite, tetraphenyl dipropylene glycol diphosphite, poly(dipropylene glycol) phenyl phosphite, diisodecyl pentaerythritol diphosphite, bis(tridecyl) pentaerythritol diphosphite, distearyl pentaerythritol diphosphite, bis(nonylphenyl) pentaerythritol diphosphite, bis(2,4-di-t-butylphenyl) pentaerythritol diphosphite, phenyl 4,4'-isopropylidenediphenyl pentaerythritol diphosphite, tetraphenyl tetra(tridecyl) pentaerythritol tetraphosphite, tetra(tridecyl)-4,4'-isopropylidenediphenyl phosphite, hydrogenated bisphenol A phosphite polymer, pentaerythritol hydrogenated bisphenol A triphenyl phosphite polycondensate, tetra(tridecyl)-4,4'-n-butylidene bis(2-t-butyl-5-methylphenol) diphosphite, bis(neopentyl glycol) 1,4-cyclohexane dimethylene phosphite, bis(octylphenyl) bis[4,4'-n-butylidene bis(2-t-butyl-5-methylphenol)] 1,6-hexanediol phosphite, and tetra (tridecyl)-1,1,3-tris(2'-methyl-5'-t-butyl-4'-oxyphenyl) butane diphosphite; and phosphite diesters such as dimethyl hydrogenphosphite, dibutyl hydrogenphosphite, di(2-ethylhexyl) hydrogenphosphite, dibutyl hydrogenphosphite, dilauryl hydrogenphosphite, dioleyl hydrogenphosphite, and diphenyl hydrogenphosphite.

Examples of such phosphonic acids include, but are not limited to phosphonate diesters such as dimethyl methylphosphonate, ethyl diethylphosphonoacetate, bis(2-chloroethyl) vinylphosphonate, diethyl N,N-bis(2-hydroxyethyl)aminomethylphosphonate, dibutyl butylphosphonate, di-2-ethylhexyl hydroxymethylphosphonate, di-2-ethylhexyl 2-ethylhexylphosphonate, dimethyl phenylphosphonate, diethyl phenylphosphonate, diallyl phenylphosphonate, dioctyl phenylphosphonate, and dinaphthyl phenylphosphonate; acidic phosphonate esters such as mono-2-ethylhexyl 2-ethylhexylphosphonate and monooctyl phenylphosphonate; and phosphonate ester salts such as ammonium mono-2-ethylhexyl 2-ethylhexylphosphonate, triethanolamine monooctyl phenylphosphonate, melamine mono-2-ethylhexyl 2-ethylhexylphosphonate, and sodium monooctyl phenylphosphonate.

Examples of such phosphines include, but are not limited to, phosphines such as triethylphosphine, tri-n-propylphosphine, tri-n-butylphosphine, tri-n-hexylphosphine, tri-n-octylphosphine, tris(2-cyanoethyl) phosphine, tris(3-hydroxypropyl)phosphine, tricyclohexylphosphine, dicyclohexylphosphine, triphenylphosphine, tri-p-tolylphosphine, tri(2,6-dimethoxyphenyl)phosphine, 9-phosphabicyclo[3.3.1], [4.2.1]nonane (mixture), bis(1,2-diphenylphosphino)ethane, bis(1,4-diphenylphosphino)butane, diphenyl-p-styrylphosphine, diphenylphosphinous chloride, and bis (diphenylphosphino)ferrocene; phosphine oxides such as triethylphosphine oxide, tri-n-propylphosphine oxide, tri-n-butylphosphine oxide, tri-n-hexylphosphine oxide, tri-n-octylphosphine oxide, tris(2-cyanoethyl)phosphine oxide, tris(3-carboxyethyl)phosphine oxide, tris(3-hydroxypropyl) phosphine oxide, and triphenylphosphine oxide; and phosphonium salts such as tetra-n-butylphosphonium bromide, tri-n-butylallylphosphonium bromide, ethylenebistris(2-cyanoethyl)phosphonium bromide, ethyltriphenylphosphonium bromide, tetraphenylphosphonium bromide, tri-n-octylethylphosphonium bromide, tetra-n-butylphosphonium O,O-diethylphosphorodithioate, tetrakis(hydroxymethyl) phosphonium sulfate, tetra-n-butylphosphonium iodide, ethyltriphenylphosphonium iodide, triethylbenzylphosphonium chloride, tetra-n-butylphosphonium chloride, tri-n-butyltetradecylphosphonium chloride, tri-n-butylhexadecylphosphonium chloride, tris(2-cyanoethyl) allylphosphonium chloride, benzyltriphenylphosphonium chloride, and bis(triphenylphosphin)iminium chloride.

Examples of such sulfur-containing phosphorus compounds include, but are not limited to, dimethyl phosphorodithioate, diethyl phosphorodithioate, di-n-propyl phosphorodithioate, ammonium diethyl phosphorodithioate, melamine di-n-propyl phosphorodithioate, sodium dimethyl phosphorodithioate, trilauryl trithiophosphite, tris(lauryl-2-thioethyl) phosphite, diphenyl bis[4,4'-n-butylidene bis(2-t-butyl-5-methylphenyl)] thiodiethanol diphosphite, triphenylphosphine sulfide, tris(2-cyanoethyl)phosphine sulfide, and tri-n-butylphosphine sulfide.

In the present invention, such phosphoruses can be used in an amount of 5–40 wt. %, preferably 10–30 wt. % based on such resins. Amounts smaller than 5 wt. % cannot bring about sufficient synergistic effects for improving the flame retardancy. Amounts greater than 40%, on the other hand, cause deteriorations in physical properties. Because of these disadvantages, amounts outside the above range are not preferred practically.

In such resins, the phosphoruses may be present separately from components such as the diguanamine or a part or the entire part of the phosphoruses may form a salt with the diguanamine according to the present invention. Inclusion of a salt, for example, in the form of a salt of phosphoric acid, a polyphosphoric acid, phosphorous acid, phosphonic acid, acidic ammonium polyphosphate, an acidic phosphate ester or an acidic phosphonate ester with the diguanamine is preferred because of still better synergistic effects for the improvement of flame retardancy.

The diguanamine according to the present invention can improve the flame retardancy of such a resin further when incorporated together with a particular isocyanuric acids and/or cyanuric acids in the resin as a method for making the resin retardant to flame. This combined use is therefore preferred.

Illustrative of such particular isocyanuric acids and cyanuric acids include isocyanuric acids represented by the following formula (9):

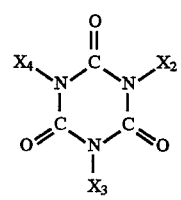

(9)

wherein $X_2$, $X_3$ and $X_4$ may be the same or different and individually represent a hydrogen atom or a $C_{1-3}$ alkyl, $C_{1-3}$ alkyloxy, phenyl or glycidyl group, and cyanuric acids represented by the following formula (10):

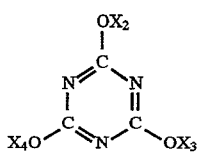 (10)

wherein $X_2$, $X_3$ and $X_4$ have the same meanings as defined in formula (9).

The isocyanuric acids useful in the practice of the present invention are compounds represented by the formula (9) in which $X_2$, $X_3$ and $X_4$ are the same or different and individually represent a substituent selected from the group consisting of a hydrogen atom, $C_{1-3}$ alkyl groups, $C_{1-3}$ oxyalkyl group, a phenyl group and a glycidyl group. Specific examples of such isocyanuric acids include, but are not limited to, isocyanuric acid, methyl isocyanurate, trimethyl isocyanurate, triethyl isocyanurate, tris(2-hydroxyethyl) isocyanurate, phenyl isocyanurate, diphenyl isocyanurate, triphenyl isocyanurate, dimethyl phenyl isocyanurate and triglycidyl isocyanurate.

The cyanuric acids useful in the practice of the present invention are compounds represented by the formula (10) in which $X_2$, $X_3$ and $X_4$ have the same meanings as defined in formula (9). Specific examples of such cyanuric acids include, but are not limited to, cyanuric acid, methyl cyanurate, trimethyl cyanurate, triethyl cyanurate, tris(2-hydroxyethyl) cyanurate, phenyl cyanurate, diphenyl cyanurate, triphenyl cyanurate, dimethyl phenyl cyanurate, and triglycidyl cyanurate.

In the present invention, the molar ratio of the sum of the isocyanuric acids and the cyanuric acids to the diguanamine can range from 0.02 to 10, preferably from 0.1 to 5. Molar ratios smaller than 0.02 are too small to sufficiently bring about effects of their combined use, whereas molar ratios greater than 10 lead to reductions in physical properties. Molar ratios outside the above range are therefore not preferred from the practical viewpoint.

In the resin, such isocyanuric acids and cyanuric acids may present separately from components such as the diguanamine, or a part or the entire part of these acids may form salts and/or react with the diguanamine according to the present invention and may hence be contained partially or entirely in the form of salts. Inclusion of a salt and/or product, for example, a salt of an isocyanuric acid with the diguanamine and a reaction product of triglycidyl cyanurate with the diguanamine can bring about still better flame-retarding effects, heat resistance and the like and is hence preferred.

Useful examples of such a salt include, but are not limited to, a salt obtained by dissolving or dispersing the isocyanuric acid and the diguanamine in a solvent and heating the resulting solution to react them, a salt obtained by reacting the isocyanuric acid with the diguanamine at a molar ratio of from 1 to several, and mixtures of salts formed through these reactions.

Further, the diguanamine according to the present invention can improve the flame retardancy of a resin further when employed in accordance with a flame-retarding method for the resin in which the diguanamine is incorporated together with an amino-containing compound in the resin. This combined use of the diguanamine with the amino-containing compound is therefore preferred.

The amino-containing compound contains at least one aliphatic group, alicyclic group, aromatic group or heterocyclic group having at least two carbons. Preferred are those containing at least one aliphatic group, alicyclic group or heterocyclic group having at least two carbons. More preferred are compounds which contain at least one 1,2-ethanediamino group (>N—$CH_2CH_2$—N<), cyclohexylamino group

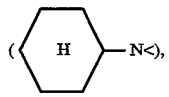

piperidino group;

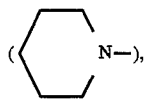

piperadinyl group)

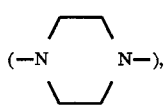

morpholino group

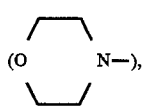

amido bond

or urea bond

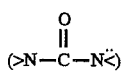

as well as dicyandiamide, guanidine, and reaction products between such compounds and aldehydes such as formaldehyde or epoxy compounds.

Specific examples of such amino-containing compounds include, but are not limited to, 1,2-ethylenediamine, 1,3-diaminopropane, 1,2-diaminopropane, 1,4-butylenediamine, 1,6-hexamethylenediamine, polyalkylenepolyamine such as diethylenetriamine, triethylenetetramine, tetraethylenepentamine and pentaethylenehexamine, cyclohexylamine, cyclohexyldiamine, 1,3-bis(aminomethyl)cyclohexane, aniline, benzylamine, furfurylamine, N-(3-aminopropyl) morpholine, N-(2-aminoethyl)morpholine, N-(2-aminoethyl)piperazine, N-(3-aminopropyl)piperazine, N-(2-aminoethyl)piperidine, N,N'-bis(2-aminoethyl)piperazine, dicyandiamide, guanidine, urea, and polyamide resins; and reaction products between these compounds and aldehydes such as formaldehyde, for example, ethylenediamineformaldehyde (1/1) reaction product, piperazineformaldehyde (1/1) reaction product, pentamethylenehexamine, and salts thereof.

In the present invention, the amino-containing compound can be used in an amount of 0.01–10 wt. %, preferably 0.05–5 wt. % based on the resin. Amounts smaller than 0.01 wt. % cannot exhibit synergistic effects to sufficient extent for the improvement of flame retardancy, whereas amounts greater than 10 wt. % lead to reductions in physical properties. Amounts outside the above range are therefore not preferred from the practical viewpoint.

Illustrative examples of resins to which the present invention can be applied include synthetic resins and oils, for example, thermoplastic resins, thermosetting resins and rubbers as well as modified resins such as blends, block copolymers, graft copolymers and rubber-modified polymers of such resins and/or rubbers.

Specific examples of such resins include, but are not limited to, thermoplastic resins, for example, styrene resins such as polystyrene, co- and ter-polymers between styrene and other monomers [e.g., maleic anhydride, α-methylstyrene, butadiene, acrylonitrile, and (meth) acrylate esters], rubber-modified polystyrenes, rubber-modified styrene-acrylonitrile copolymers and rubber-modified styrene-maleic anhydride copolymers, polyolefin resins such as polyethylene, polypropylene, polybutylene, poly-3-methylbutene, ethylene-vinyl acetate copolymers, ethylene-propylene copolymers and EPDMs (ethylene-propylene-diene terpolymers), (meth)acrylic resins such as polymethyl acrylate and polymethyl methacrylate, polyamide resins such as nylon 4, nylon 6, nylon 11, nylon 12, nylon 46, nylon 66, nylon 610, nylon 612 and copolymerized nylons, saturated polyester resins such as polyethylene terephthalate and polybutylene terephthalate, polyphenylene ether resins such as poly(2,6-dimethyl-1,4-phenylene) ether, poly(2-methyl-6-ethyl-1,4-phenylene) ether, poly(2,6-diethyl-1,4-phenylene) ether, poly(2,6-di-n-propyl-1,4-phenylene) ether, poly(2-methyl-6-n-butyl-1,4-phenylene) ether, poly(2-methyl-6-chloro-1,4-phenylene) ether, poly(2-methyl-6-hydroxyethyl-1,4-phenylene) ether, poly(2-methyl-6-chloroethylene-1,4-phenylene) ether and 2,6-dimethylphenol-2,3,6-trimethylphenol copolymers, end-capped polyphenylene ethers thereof and resins obtained by modifying such polyphenylene ether resins with such as styrene resin and polyamide resin, polyacetal resins such as polyoxymethylene and polymers containing oxymethylene units and other units (for example, succinic anhydride, n-dodecenylsuccinic anhydride, methylsuccinic anhydride, tetrapropylsuccinic anhydride, maleic anhydride, phthalic anhydride, hexahydrophthalic anhydride, itaconic anhydride, β-hydroxypropylene group, oxyalkylene groups); halogenated resins such as polyvinyl chloride, polyvinylidene chloride, chlorinated polyethylene, chlorinated polypropylene, chlorinated rubber, co- and ter-polymers between vinyl chloride and other monomers [e.g., vinyl acetate, ethylene, propylene, styrene, isobutylene, vinylidene chloride, maleic anhydride, acrylonitrile, butadiene, isoprene, chlorinated propylene, and (meth) acrylate esters], polyvinyl bromide, brominated polyethylene, polyvinyl fluoride, polyvinylidene fluoride and fluorinated resins, vinyl acetate resin, polyamide-imides, polyimide resins, polyether-imides, polyphenylene-sulfide resins, polyether-sulfones, polysulfone resins, polyamine-sulfones, polycarbonate resins, liquid crystal (polyester) polymers, cyclic polyolefins, polyetheretherketones, polyarylates, phenoxy resins, silicone resins, blends, block copolymers, graft copolymers and rubber-modified polymers of these resins; thermosetting resins, for example, unsaturated polyester resins such as diallyl phthalate resins (e.g. polydiallyl phthalate, polydiallyl terephthalate and polydiallyl 2,6-naphthalenedicarboxylate) and maleic-acid-(fumaric acid)-containing polyester-styrene resins, urethane resins, epoxy resins, silicone resins, phenol resins, furan resins, amino resins, blends thereof and resins obtained by modifying these resins with rubber or the like; rubbers such as synthetic rubbers and vulcanized rubbers; and blends and modified resins of these resins and oils such as lubricating oils, silicone oils, metal working oils and polypropylene wax.

These resins can each be used in an amount of 50–98 wt. %, preferably 65–96 wt. % based on a corresponding resin composition obtained in accordance with the flame-retarding method of the present invention. If the amount of the resin exceeds 98 wt. %, flame-retarding effects become smaller. An amount smaller than 50 wt. %, on the other hand, results in a composition having poor formability or reduced physical properties due to deterioration or the like of the resin. Amounts outside the above range are therefore not preferred.

In the flame-retarding method of the present invention for resins, the thermal stability and the like of such resins can be improved by additionally incorporating additives such as phenolic antioxidants, amine-base antioxidants, sulfur-containing antioxidants and light stabilizers. These additives can be chosen as needed depending on the application purpose.

Illustrative of such phenolic antioxidants include 3-methyl-4-isopropylphenol, 2,6-di-t-butylphenol, 2,4-dimethyl-6-t-butylphenol, 2,6-di-t-butyl-4-methylphenol, 2,4-dimethyl-6-(2-methylcyclohexyl)phenol, 2,5-di-t-butylhydroquinone, 3-t-butyl-4-hydroxyanisole, styrenated phenol, hydroquinone monobenzyl ether, 2,5-diamylhydroquinone, 2,6-di-t-butyl-4-methoxyphenol, 4-hydroxymethyl-2,6-di-t-butyl phenol, 2,6-di-t-butyl-α-dimethylamino-p-cresol, 4-(N-stearoylamino)phenol, 4,4'-dihydroxydiphenyl, 4,4'-bis(2,6-di-t-butylphenol), 2,2'-methylene-bis-(4-methyl-6-t-butylphenol), 2,2'-methylene-bis-(4-ethyl-6-t-butylphenol), 4,4'-methylene-bis-(2-methyl-6-t-butylphenol), 4,4'-methylene-bis-(2,6-di-t-butylphenol), 2,2'-dihydroxy-3,3'-bis-(2-methylcyclohexyl)-5,5'-dimethyl-diphenylmethane, 1,1-bis-(4-hydroxyphenyl)-cyclohexane, 4,4'-cyclohexilidene-bis-(2-cyclohexylphenol), 4,4'-butylidene-bis-(3-methyl-6-t-butylphenol), octadecyl 3-(3,5-di-t-butyl-4-hydroxyphenyl) propionate, triethylene glycol bis-[3-(3-t-butyl-5-methyl-4-hydroxyphenyl)propionate], 1,6-hexanediol bis-[3-(3,5-di-t-butyl-4-hydroxyphenyl)propionate], pentaerystyryl tetrakis-[3-(3,5-di-t-butyl-4-hydroxyphenyl)propionate], ethyl 3-(3,5-di-t-butyl-4-hydroxyphenyl)propionate, 2,6-bis(2-hydroxy-3-t-butyl-5-methylbenzyl)-4-methylphenol, 1,1,3-tris-(2-methyl-4-hydroxy-5-t-butylphenyl)-butane, 1,3,5-tris-(3,5-di-t-butyl-4-hydroxybenzyl)-2,4,6-trimethylbenzene, dioctadecyl 2-(3-methyl-4-hydroxy-5-t-butylbenzyl)malonate, didodecyl 4,4-thiobis-(2-methyl-6-t-butylphenyl)malonate, bis-(2-hydroxy-3,5-di-t-butylphenyl) sulfide, 4,4'-thio-bis-(3-methyl-6-t-butylphenol), 1,1-bis-(2-methyl-4-hydroxy-5-t-butylphenyl)-3-dodecylmercapto-butane, octadecyl S-(3,5-dimethyl-4-hydroxyphenyl)-thioglycolate, 2,2'-thio-bis-(4-methyl-6-t-butylphenol), dimethyl 4-hydroxy-3,5-di-t-butylbenzylphosphonate, diethyl 4-hydroxy-3,5-t-butylbenzylphosphonate, dioctadecyl 4-hydroxy-3,5-di-t-butylbenzylphosphonate, tris-(3,5-di-t-butyl-4-hydroxyphenyl) phosphate, 4-hydroxymethyl-1-phospha-2,6,7-trioxabicyclo[2.2.2]-octane-3-(3,5-di-t-butyl-4-hydroxyphenyl) propionate, 2,4-bis-(octylthio)-6-(4-hydroxy-3,5-di-t-butylanilino)-s-triazine, 2,4-bis-(3,5-di-t-butyl-4-hydroxyphenoxy)-6-octyl-s-triazine, 1,3,5-tris-(3,5-di-t-butyl-4-hydroxyhydrocinnamoyl)-hexahydro-s-triazine, tris(3,5-di-t-butyl-4-hydroxybenzyl) isocyanurate, tris[3-(3,5-di-t-butyl-4-hydroxyphenyl)propionyloxyethyl] isocyanurate, N,N'-hexamethylenebis-(3,5-di-t-butyl-4-hydroxy-hydrocinnamide), 2-t-butyl-6-(3'-t-butyl-5'-methyl-2'-hydroxybenzyl)-4-methylphenyl acrylate, 2,2'-oxamido-bis[ethyl 3-(3,5-di-t-butyl-4-hydroxyphenyl) propionate], 3,9-bis{1,1-dimethyl-2-[3-(3-t-butyl-4-hydroxy-5-methylphenyl)propionyloxy]ethyl}-2,4,8,10- tetraoxapyro[5.5]undecane. They can each be used in an amount of 0.001–2.0 wt. %, preferably 0.05–1.0 wt. % based on the resin.

Exemplary amine-base antioxidants include phenyl-1-naphthylamine, phenyl-2-naphthylamine, N,N'-diphenyl-p-phenylenediamine, N,N'-di-2-naphthyl-p-phenylenediamine, N,N'-di-sec-butyl-p-phenylenediamine, 6-ethoxy-2,2,4-trimethyl-1,2-dihydroxyquinoline, 6-dodecyl-2,2,4-trimethyl-1,2-dihydroxyquinoline, dioctyliminodibenzyl, diethanolamine, diisopropanolamine, dibutanolamine, triethanolamine, triisopropanolamine, tributanolamine, dodecylethanolamine, octadecyldiethanolamine, N,N'-diphenylethylenediamine, triethyltetramine, 7 mole ethylene oxide adduct of dodecylamine, 4 mole ethylene oxide adduct of tridecylamine, 10 mole ethylene oxide adduct of octadecylamine, and 20 mole ethylene oxide adduct of hexadecylamine. They can each be used in an amount of 0.02–5.0 wt. % based on the resin.

Examples of such sulfur-containing antioxidants include diethyl 3,3'-thio-di-propionate, dilauryl 3,3'-thio-di-propionate, ditridecyl 3,3'-thio-di-propionate, dimyristyl 3,3'-thio-di-propionate, distearyl 3,3'-thio-di-propionate, 2-methylmercaptobenzoimidazole, stearyl (3,5-dimethyl-4-oxybenzyl)thioglycolate, diphenyl thiourea, thiodipropionic acid, phenothiazine and pentaerythritol tetrakis-(β-lauryl thiopropionate). They can be used in an amount of 0.01–4.0 wt. %, preferably 0.05–2.0 wt. % based on the resin.

Illustrative of such light stabilizers include, but are not limited to, benzophenone compounds such as benzophenone, 2-hydroxy-4-methoxybenzophenone, 2,2'-dihydroxy-4,4'-dimethoxybenzophenone, 2,2'-dihydroxy-4-methoxybenzophenone, 2-hydroxy-4-n-octyloxybenzophenone, 2-hydroxy-4-n-dodecyloxybenzophenone, 2-hydroxy-4-octadecyloxybenzophenone, 2,4-dihydroxybenzophenone, 2-hydroxy-4-benzoyloxybenzophenone, 2,6-dihydroxy-5-benzoylbenzophenone, bis(5-benzoyl-4-hydroxy-2-methoxyphenyl)methane, 2,2',4,4'-tetrahydroxybenzophenone, 2-hydroxy-4-methoxy-2'-carboxybenzophenone, 2-hydroxy-4-methoxy-4'-chlorobenzophenone, 2-hydroxy-5-chlorobenzophenone, and 2-hydroxy-4-methoxybenzophenone-5-sulfonic acid; acetophenone compounds such as 2-hydroxy-5-methoxyacetophenone; benzotriazole compounds such as 2-(2'-hydroxy-5'-methylphenyl)benzotriazole, 2-(2'-hydroxy-3',5'-diisoamylphenyl)benzotriazole, 2-[2'-hydroxy-3',5'-bis(α,α-dimethylbenzyl)phenyl] benzotriazole, 2-(2'-hydroxy-3',5'-di-t-butylphenyl) benzotriazole, 2-(2'-hydroxy-5'-t-octylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, and 2,2'-methylene-bis[4-(1,1,3,3-tetramethylbutyl)-6-(2-N-benzotriazole-2-yl)phenol]; benzoate compounds such as phenyl salicylate, 4-t-butylphenyl salicylate, 4-t-octylphenyl salicylate, dibenzoylresorcinol, tribenzoylresorcinol, bis(4-t-butylbenzoyl)resorcin, ethylene glycol monosalicylate, and 2,4-di-t-butylphenyl 3,5'-di-t-butyl-4'-hydroxybenzoate; oxalic anilide compounds such as 2-ethoxy-2'-ethyloxalic acid bisanilide and 2-ethoxy-5-t-butyl-2'-ethyloxalic acid bisanilide; cyanoacrylate compounds such as 2-ethylhexyl 2-cyano-3,3-diphenylacrylate, ethyl 2-cyano-3,3-diphenylacrylate and n-butyl 2-cyano-3-methyl-3-(p-methoxyphenyl)acrylate; organic nickel compounds such as nickel bis(octylphenyl)sulfide, n-butylamine nickel [2,2'-thiobis(4-t-octyl phenolate)], 2-ethylhexylamine nickel [2,2'-thiobis(4-t-octyl phenolate)], nickel dibutyldithiocarbamate and triethanolamine nickel [2,2'-thiobis(4-t-octylphenolate)]; and hindered piperazine compounds such as tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl) sebacate, bis(1,2,2,6,6-pentamethyl-4-piperidyl) sebacate, bis(N-methyl-2,2,6,6-tetramethyl-4-piperidyl) sebacate, bis(1,2,2,6,6-pentamethyl-4-piperidyl) 2-(3,5-di-t-butyl-4-hydroxybenzyl)-2-n-butylmalonate, condensation product of dimethyl succinate and 2-(4-hydroxy-2,2,6,6-tetramethyl-1-piperidyl)ethanol, phenyl 4-piperidylcarboxylate, and 1,1'-(1,2-ethanediyl) bis(3,3,5,5-tetramethylpiperazinone).

It is also possible to choose and use, as needed, one or more of the following additives: nucleating agents, for example, 4-t-butyl benzoate, adipic acid and diphenyl acetate; metal inactivating agents, for example, oxanilide, dicarboxylic dihydrazides, dicarboxylic bisphenylhydrazides, salicylic hydrazide, N-salicyloyl-N'-salicylidenehydrazine, bis-salicyloyldicarboxylic dihydrazides, bis-diacylated dicarboxylic dihydrazides, salicyloyl-hydrazinotriazine, bis-salicyloyl hydrazine and oxalic bis(benzilidenehydrazide); free radical promoters, for example, 2,3-dimethyl-2,3-diphenylbutane ("INTALOX CC DFB", trade name; product of Peroxyd Chemie GmbH), 3,4-dimethyl-3,4-diphenylhexane ["INTALOX CC DFH", trade name; product of Peroxyd Chemie GmbH), 2,3-dimethyl-2,3-diphenylhexane, cyclohexenecarboguanamine and norbornanecarboquanamine.

In the flame-retarding method of the present invention, no particular limitation is imposed on the manner of production of the resin composition. It is possible to apply any production method which is generally employed upon mixing powdery additives in such a resin. In the case of a thermoplastic resin or the like, for example, the resin in the form of pellets or a powder is mixed in advance with additives at room temperature and the resulting mass is melted, mixed and then formed by an extruder, a heating roll, a kneader or the like. As an alternative, a resin containing the additives at high concentrations is produced beforehand and is then melted and kneaded together with the ordinary resin, and the resulting mass is thereafter formed. In the case of a thermosetting resin or the like, on the other hand, one or more components essential to the present invention are added, before curing, to a monomer or prepolymer or to a dope or compound which has been formed by adding one or more reinforcing materials to the monomer or prepolymer. The resulting mixture is then kneaded, formed and cured. It is however to be noted that the practice of the present invention shall not be limited to such production methods.

In the flame-retarding method of the present invention, one or more other additives can also be incorporated as needed to extent not impairing the advantageous effects of the present invention. Illustrative examples of such additives include plasticizers, dyes and pigments, dispersants, organic chelating agents, stabilizers, foaming agents, antihazing agents, delustering agents, surface treatments, fluorescent agents, mildewproofing agents, bacteriocides, antioxidants, ultraviolet light absorbers, conventional flame retardants or flame-retarding aids such as antimony trioxide, barium metaborate, zirconium dioxide, lead oxide and zinc borate, lubricants such as higher fatty acids, higher fatty acid esters, higher fatty acid metal salts and bisamides, antistatic agents such as sulfonic acids, quaternary ammonium salts, polyhydric alcohol esters, alkylamides, alkylamines and electrically conductive carbon black, reinforcing materials such as glass fibers and carbon fibers; fillers such as talc, clay, calcined clay, mica, calcium silicate, calcium sulfate, calcium carbonate, glass beads, molybdenum disulfide and graphite, processing aids, parting agents, and other polymers.

In the flame-retarding method of the present invention, it is preferred to additionally incorporate at least one flame-retarding aid selected from phosphoruses consisting of simple substances of phosphorus and phosphorus-containing compounds.

Preferred phosphoruses are, for example, red phosphorus, phosphoric acid, polyphosphoric acids, phosphorous acid, phosphonic acid, phosphate salts, polyphosphate salts, phosphite salts, phosphonate salts, phosphate esters, phosphite esters, phosphonate esters, phosphines and sulfur-containing phosphorus compounds. Particularly preferred polyphosphate salts are ammonium polyphosphates represented by the following formula:

$(NH_4)_{n+2}P_nO_{3n+1}$ wherein n stands for an integer greater than 5.

As an alternative, it is also preferred to additionally incorporate at least one flame-retarding aid selected from the isocyanuric acids and cyanuric acids represented by formula (9) and formula (10), respectively.

As a further alternative, it is also preferred to additionally incorporate at least one flame-retarding aid selected from amino-containing compounds. Preferred are, for example, compounds containing at least one group selected from

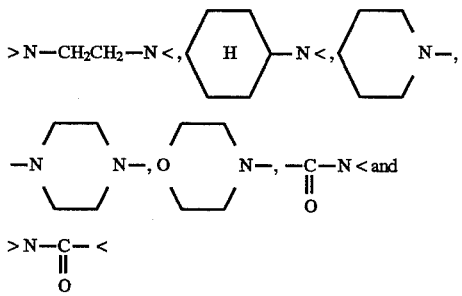

dicyandiamide and guanidine, and their reaction products with aldehydes or epoxy compounds.

It is particularly preferred to incorporate the above-described phosphoruses and amino-containing compounds together as flame-retarding aids.

The resin to which the flame-retarding method of this invention is applied is preferably a thermoplastic resin. The thermoplastic resin can preferably be at least one thermoplastic resin selected from the group consisting of polyolefin resins, polyamide resins, styrene resins, polyphenylene ether resins, saturated polyester resins, polycarbonate resins, polyacetal resins and acrylic resins.

As the resin, a thermosetting resin is also preferred. This thermosetting resin can preferably be at least one thermosetting resin selected from the group consisting of unsaturated polyester resins, diallyl phthalate resins, epoxy resins and urethane resins.

Thermal Stabilization Method

Owing to the incorporation of the diguanamine of formula (1) or (2) in the resin, the thermal stabilization method according to the present invention can substantially improve the thermal stability, ultraviolet light resistance and the like of the resin and moreover can minimize coloration or discoloration of the resin during its processing and formation at high temperatures. The diguanamine is excellent in high-temperature stability, non-volatility and handling and, moreover, can significantly protect the resin from decomposition or deterioration by heavy metal ions such as copper ions.

In the thermal stabilization method of the present invention, the diguanamine is used in an amount of 0.01–5 wt. %, preferably 0.02–1 wt. % based on the resin. Amounts smaller than 0.01 wt. % can hardly exhibit sufficient effects for the improvement of stability to heat, light and the like, whereas amounts greater than 5 wt. % cannot bring about any substantial extra advantage for the improvement of the stability and are not preferred economically.

Resins to which the thermal stabilization method of this invention can be applied are substantially the same as those described above as resins to which the flame-retarding method of this invention is applicable. The thermal stabilization method of this invention can enhance its stability-improving effects still further when additives such as the above-described phenolic antioxidants, amine-base antioxidants, sulfur-containing antioxidants, light stabilizers, nucleating agents and other additives are additionally used in amounts similar to those specified above or the below-described phosphite antioxidants are used additionally. These additives can be chosen as needed depending on the application purpose.

Incidentally, illustrative examples of phosphite antioxidants include triphenyl phosphite, tris(nonylphenyl) phosphite, tris(dinonylphenyl) phosphite, tris(2,4-di-t-butylphenyl) phosphite, tris(2,5-di-t-butylphenyl) phosphite, tris(2,6-di-t-butylphenyl) phosphite, tris(mono/di-mixed nonylphenyl) phosphite, diphenyl decyl phosphite, 2-ethylhexyl diphenyl phosphite, phenyl diisodecyl phosphite, diphenyl acid phosphite, trilauryl phosphite, tridecyl phosphite, tris(2-ethylhexyl) phosphite, tributyl phosphite, dibutyl acid phosphite, dilauryl acid phosphite, ditridecyl pentaerythritoldiphosphite, distearyl pentaerythritoldiphosphite, bis(2,4-di-t-butylphenyl) pentaerythritoldiphosphite, bis(2,6-di-t-butyl-4-methylphenyl)pentaerythritoldiphosphite, bis(nonylphenyl) pentaerythritoldiphosphite, diisodecyl pentaerythritoldiphosphite, phenyl 4,4'-isopropylidenediphenol pentaerythritoldiphosphite, trilauryl trithiophosphite, tris(lauryl-2-thioethyl)phosphite, diphenyl bis[4,4'-n-butylidenebis(2-t-butyl-5-methylphenol)] thiodiethanoldiphosphite, bis(neopentylglycol) 1,4-cyclohexanedimethylenephosphite, hydrogenated 4,4'-isopropylidenediphenol polyphosphite, bis(octylphenyl) bis [4,4'-n-butylidenebis(2-t-butyl-5-methylphenol)]1,6-hexanediol diphosphite, tetratridecyl-4,4'-n-butylidenebis (2-t-butyl-5-methylphenol) diphosphite, tetratridecyl-1,1,3-tris(2'-methyl-5'-t-butyl-4'-oxyphenyl)butane diphosphite, and tetra($C_{12-15}$ mixed alkyl) 4,4'-isopropylidenediphenyl diphosphite. Preferably these phosphite antioxidants can each be used in an amount of 0.01–1.0 wt. % based on the resin.

In the thermal stabilization method according to the present invention, production of each resin composition and use of other additives can be conducted in a similar manner to the above-described flame-retarding method but are not limited to the corresponding procedures in the flame-retarding method.

The resin to which the thermal stabilization method of this invention is applied is preferably a thermoplastic resin. The thermoplastic resin can preferably be at least one thermoplastic resin selected from the group consisting of polyphenylene ether resins, polyacetal resins, polyamide resins and polyolefin resins. More preferably, the polyolefine resin can be at least one resin selected from the group consisting of polyethylene resin, polypropylene resin and ethylene-propylene copolymers.

Compatibilizing Method

According to the compatibilizing method of this invention, the diguanamine represented by formula (1) or (2) is incorporated in a blend of at least two different kinds of resins which includes at least one resin selected from polyamide resins, polyphenylene ether resins, polyimide resins and polyalamide resins. As a result, the compatibility of the two or more resins of different kinds is substantially improved and, moreover, coloration or discoloration of the resin is minimized during its processing and forming at high temperatures. The diguanamine is superb because it has excellent high-temperature stability and non-volatility, undergoes minimized sublimation, bleeding or the like, facilitates the production of the resin composition, has good melt dispersibility in the polyamide resins, polyphenylene ether resins and the like, and can improve the thermal stability of the resin. The diguanamine can therefore provide an excellent modification method for resins.

In the compatibilizing method of this invention, the diguanamine can be used generally in an amount of 0.5–20 wt. %, based on the total amount of the resins. The amount of diguanamine can be suitably chosen within the above range as needed. Amounts smaller than 0.5 wt. % can hardly bring about sufficient effects for the improvement of the compatibility, whereas amounts greater than 20 wt. % cannot bring about any substantial extra improving effects but causes reductions in resin properties and are not preferred either from the economical standpoint.

Resins to which the compatibilizing method of this invention can be applied are substantially the same as those described above in connection with the flame-retarding method. Specific examples of at least two resins of different kinds include, but are not limited to, combinations of one type of resins selected from polyamide resins, polyphenylene ether resins, polyimide resins and polyaramid resins and resins other than the one type of resins, for example, polyamide resins and ABS resins, polyamide resins and polyphenylene ether resins, polyimide resins and polyphenylene ether resins, as two resins of different kinds as well as polyamide resins, polyphenylene ether resins and other resins as three or more different kinds.

In the compatibilizing method of the present invention, additives such as the above-described phenolic antioxidants, amine-base antioxidants, sulfur-containing antioxidants, phosphite antioxidants, light stabilizers, nucleating agents and other additives can be used additionally in amounts similar to those described above. These additives can be chosen as needed depending on the application purpose.

Further, production of a resin composition in accordance with the compatibilizing method of this invention can be conducted in a similar manner to the production according to the above-described flame-retarding method, although the former production is not limited to the latter one.

Diguanamine Derivatives

In addition of the use of the diguanamines represented by formula (1) or (2), the present invention also provides derivatives of these diguanamines, their preparation process and their use.

Examples of such diguanamine derivatives include diguanamine derivatives represented by the following formula (11):

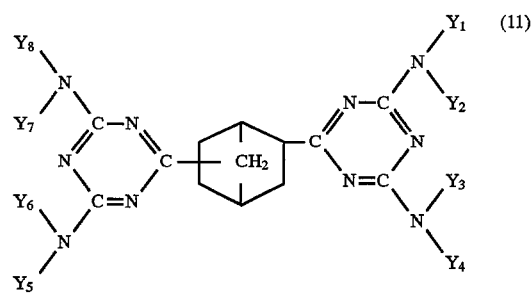

wherein the bonding sites of the 1,3,5-triazin-2-yl groups are the 2,5- or 2,6-positions, and $Y_1$, $Y_2$, $Y_3$, $Y_4$, $Y_5$, $Y_6$, $Y_7$ and $Y_8$ are the same or different and individually represent a substituent selected from the group consisting of a hydrogen atom and groups containing at least two carbon atoms, with the proviso that at least one of $Y_1$, $Y_2$, $Y_3$, $Y_4$, $Y_5$, $Y_6$, $Y_7$ and $Y_8$ is a group containing at least two carbon atoms, and those represented by the following formula (12):

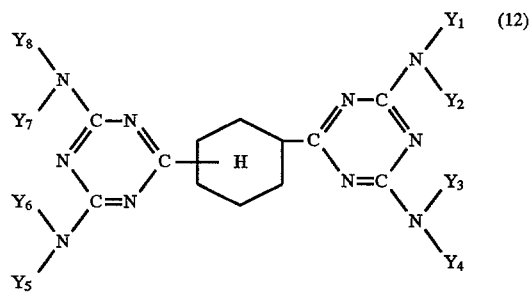

wherein the bonding sites of the 1,3,5-triazin-2-yl groups are the 1,2-, 1,3- or 1,4-positions and $Y_1$, $Y_2$, $Y_3$, $Y_4$, $Y_5$, $Y_6$, $Y_7$ and $Y_8$ have the same meanings as defined in formula (11).

In the diguanamine derivatives [formula (11)] according to this invention, the bonding sites of the 1,3,5-triazin-2-yl groups are the 2,5- or 2,6-positions. The configuration of such groups is an endo-endo form, endo-exo form or exo-exo form. These stereoisomers are all useful derivatives. In the diguanamine derivatives [formula (12)], the bonding sites of the 1,3,5-triazin-2-yl groups are the 1,2-, 1,3- or 1,4 positions. The configuration of such groups is a trans or cis form. These stereoisomers are all useful derivatives. Although such diguanamine derivatives are derivatives selected from the group consisting of the above-described isomers in bonding sites or configuration, mixtures of different derivatives and/or isomers selected from such a group are also extremely useful from the industrial viewpoint like the individual derivatives.

In formulas (11) and (12), at least one of $Y_1$, $Y_2$, $Y_3$, $Y_4$, $Y_5$, $Y_6$, $Y_7$ and $Y_8$ is a group containing at least two carbon atoms. No particular limitation is imposed in number, position, configuration and the like on the group containing at least two carbon atoms. Diguanamine derivatives in which each of $Y_2$, $Y_4$, $Y_6$ and $Y_8$ is a hydrogen atom, and $Y_1$, $Y_3$, $Y_5$ and $Y_7$ are individually a hydrogen atom or a group containing at least two carbon atoms, for example, N-mono-substituted diguanamine derivatives, N,N'-di-substituted diguanamine derivatives, N,N',N''-tri-substituted diguanamine derivatives, N,N',N'',N'''-tetra-substituted diguanamine derivatives and the like are preferred from the viewpoints of preparation and applications, that is, for the availability of raw materials, the readiness of reactions, the simpleness and convenience of steps such as purification and isolation, and the possibility of easy preparation from amines containing one amino group. Particularly preferred are N,N',N"-tri-substituted diguanamine derivatives and N,N',N",N'''-tetra-substituted diguanamine derivatives.

$Y_1$, $Y_2$, $Y_3$, $Y_4$, $Y_5$, $Y_6$, $Y_7$ and $Y_8$ in formulas (11) and (12) individually represent a substituent selected from the group consisting of a hydrogen atom and groups containing two or more carbon atoms. Useful examples of the groups containing two or more carbon atoms include aliphatic, alicyclic, aromatic and heterocyclic groups, which may optionally contain one or more branch chains, functional groups such as hydroxy, ester, ether, carboxyl, carbonyl, amido, imido, nitro, sulfonic, sulfonamido, amino, imino and/or unsaturated groups and the like. Illustrative of such groups include, but are not limited to, aliphatic groups, alicyclic groups, aromatic groups, heterocyclic groups containing 2–30 carbon atoms, groups represented by HO—$Y_9$— in which $Y_9$ is a divalent group containining at least 2 carbon atoms, groups represented by the following formula (13):

 (13)

wherein $Y_{10}$ is a group selected from the group consisting of ethylene, trimethylene and tetramethylene which may optionally contain one or more substituent groups containing 2–22 carbon atoms, m is an integer selected from 1 to 100, and $Y_9$ has same meaning as defined above, and groups represented by the following formula (14):

 (14)

wherein $Y_{10}$ and m have the same meanings as defined in formula (13).

Specific examples of such aliphatic groups alicyclic groups and heterocyclic groups containing 2–30 carbon atoms include, but are not limited to, ethyl, isopropyl, isobutyl, n-butyl, 1,2-dimethylpropyl, n-hexyl, n-octyl, 2-ethylhexyl, decyl, dodecyl, tetradecyl, hexadecyl, octadecyl, allyl, oleyl, 4-aminobutyl, 3-ethoxypropyl, butoxypropyl, myristyloxypropyl, methoxyethyl, ethoxyethyl, cyclohexyl, 4-methylcyclohexyl, phenyl, o-tolyl, α-naphthyl, benzyl, β-phenethyl, o-methoxycarbonylphenyl, p-ethoxycarbonylphenyl, 4-methoxyphenyl, tetrahydrofurfuryl, 2-(1-piperazinyl) ethyl, 2-piperidinoethyl, 2-morpholinoethyl, 3-morpholinopropyl, 2-(1-pyrrolidinyl)ethyl, and 2-pyridinyl.

In the groups represented by HO—$Y_9$—, $Y_9$ is a divalent group containing at least two carbon atoms, for example, a aliphatic, alicyclic, aromatic or heterocyclic group. Although no other particular limitation is imposed on $Y_9$, those containing 2–20 carbon atoms are preferred from the standpoint of production such as the availability of raw materials, the readiness of a reaction, and the simpleness and convenience of purification, isolation and like steps and also from the standpoint of application. As such groups contain a hydroxyl group, the corresponding diguanamine derivatives are extremely useful for a wide variety of applications such as resin raw materials, modifiers and crosslinking agents.

Specific examples of the group represented by HO—$Y_9$— include, but are not limited to, 2-hydroxyethyl, 2-hydroxypropyl, 4-hydroxybutyl, 1-hydroxymethylpropyl, 3-hydroxypropyl, 2-hydroxy-2-methylpropyl, 5-hydroxypentyl, 1-(2-hydroxyethyl)propyl, 3-hydroxypentyl, 3-hydroxy-2,2-dimethylpropyl, 1-hydroxyhexyl, 1-ethyl-3-hydroxybutyl, 8-hydroxyoctyl, 10-hydroxydecyl, 12-hydroxydodecyl, 1-(2-hydroxyethyl)-2-propenyl, 1-(3-hydroxypropyl)-1-propenyl, 1-(2-hydroxypropyl)-2-propenyl, 1-(1-hydroxypropyl)-3-pentenyl, 5-hydroxy-3-oxapentyl, 1-hydroxymethyl-3-oxabutyl, 1-(2-hydroxyethyl)-4-oxahexyl, 1-(2-hydroxypropyl)-5-oxahexyl, 4-hydroxycyclohexyl, 4-hydroxyphenyl, 2-methyl-4-hydroxyphenyl, 7-hydroxynaphthyl, 4-(hydroxymethyl)phenyl, 2-(4-hydroxyphenyl)ethyl, 4-(2-hydroxyethyl)phenyl, 3-hydroxypyridin-2-yl, and 8-hydroxyquinolin-4-yl.

In the group represented by formula (13), $Y_9$ represents is a divalent group containing at least two carbon atoms, for example, a divalent aliphatic, alicyclic, aromatic or heterocyclic group having at least two carbon atoms. Although no other particular limitation is imposed thereon, those containing 2–20 carbon atoms are preferred. Specific examples of $Y_9$ include, but are not limited to, residual groups which are formed by removing the hydroxyl group from the groups mentioned above as specific examples of the group represented by HO—$Y_9$—.

$Y_{10}$ in the groups represented by formulas (13) and (14), respectively, represents a group selected from the group consisting of ethylene, trimethylene and tetramethylene, which may optionally contain one or more substituent groups containing 2–22 carbon atoms. Useful examples of the groups include, but are not particularly limited to, aliphatic, alicyclic, aromatic and heterocyclic groups which may optionally contain one or more of various functional groups and/or branch chains. No other particular limitation is imposed on $Y_{10}$. Specific examples of $Y_{10}$ include, but are not limited to, ethylene, propylene, ethylethylene, n-butylethylene, n-dodecylethylene, phenylethylene, butoxyethylene, phenoxyethylene, 3-acryloxylpropylene, 1,2-cyclohexylene, tricyclo[4.3.1.0]-deca-7-ene-2,3-diyl, trimethylene and tetramethylene, with ethylene and propylene being preferred. In the groups represented by formula (13) and (14), respectively, in which n is other than 1, plural $Y_{10}$s may be the same or different. Where such plural $Y_{10}$s are different, they can be arranged at random or in block(s). The kind and arrangement of such plural $Y_{10}$s can be chosen freely as needed.

Further, m is an integer selected from 1–100 and cam be chosen freely as needed. However, it is generally an integer in a range of 1–50, preferably an integer in a range of 1–30.

The above-described oxaalkyl-containing diguanamine derivative is a derivative containing 1–8 groups selected from the groups represented by formula (13) or formula (14). One or more kinds of such groups may be contained in the same derivative. For the readiness of reactions, the availability of raw materials and the like, particularly useful oxaalkyl-containing diguanamine derivatives represented by formula (13) include, but are not limited to, N-mono-substituted oxaalkylated diguanamine derivatives, N,N'-di-substituted oxaalkylated diguanamine derivatives, N,N',N"-tri-substituted oxaalkylated diguanamine derivatives and N,N',N",N'''-tetra-substituted oxaalkylated diguanamine derivatives, in which the substituents are such groups as described above. For the availability of raw materials, particularly useful examples of the oxaalkyl-containing diguanamine derivative represented by formula (14) include, but are not limited to, oxaalkyl-containing diguanamine derivatives containing 3–8 groups selected from those described above.

Specific examples of the diguanamine derivative according to the present invention include, but are not limited to, 2-(4,6-diamino-1,3,5-triazin-2-yl)-5-(4-amino-6-n-octylamino-1,3,5-triazin-2-yl)-bicyclo[2.2.1.]heptane, 2-(4, 6-diamino-1,3,5-triazin-2-yl)-6-(4-amino-6-anilino-1,3,5- triazin-2-yl)-bicyclo[2.2.1]heptane, 2-(4,6-diamino-1,3,5-triazin-2-yl)-5-[4-amino-6-(2-morpholinoethylamino)-1,3,5-triazin-2-yl]-bicyclo[2.2.1]heptane, 1-(4,6-diamino-1,3,5-triazin-2-yl)-2-(4-amino-6-cyclohexylamino-1,3,5-triazin-2-yl)-cyclohexane, 1-(4,6-diamino-1,3,5-triazin-2-yl)-4-[4-amino-6-(2-morpholinoethylamino)-1,3,5-triazin-2-yl]cyclohexane, 2-(4,6-diamino-1,3,5-triazin-2-yl)-5-[4-amino-6-(2-hydroxyethylamino)-1,3,5-triazin-2-yl]-bicyclo[2.2.1]heptane, 2-(4,6-diamino-1,3,5-triazin-2-yl)-6-[4-amino-6-(2-hydroxypropylamino)-1,3,5-triazin-2-yl]-bicyclo[2.2.1]heptane, 2-(4,6-diamino-1,3,5-triazin-2-yl)-6-[4-amino-6-(5-hydroxy-3-oxapentylamino)-1,3,5-triazin-2-yl]-bicyclo[2.2.1]heptane, 2-(4,6-diamino-1,3,5-triazin-2-yl)-5-[4-amino-6-(4-hydroxyphenylamino)-1,3,5-triazin-2-yl]-bicyclo[2.2.1]heptane, 1-(4,6-diamino-1,3,5-triazin-2-yl)-3-[4-amino-6-(2- hydroxyethylamino)-1,3,5-triazin-2-yl]-cyclohexane, 1-(4,6-diamino-1,3,5-triazin-2-yl)-4-[4-amino-6-(3-hydroxypropylamino)-1,3,5-triazin-2-yl]-cyclohexane, 1-(4,6-diamino-1,3,5-triazin-2-yl)-3-[4-amino-6-(5-hydroxy-3-oxapentylamino)-1,3,5-triazin-2-yl]-cyclohexane, 1-(4,6-diamino-1,3,5-triazin-2-yl)-4-[4-amino-6-(4-hydroxyphenylamino)-1,3,5-triazin-2-yl]-cyclohexane, 2,5-bis(4-amino-6-cyclohexylamino-1,3,5-triazin-2-yl)-bicyclo[2.2.1]heptane, 2,6-bis(4-amino-6-benzylamino-1,3,5-triazin-2-yl)-bicyclo[2.2.1]heptane, 2,5-bis(4-amino-6-(2-morpholinoethylamino)-1,3,5-triazin-2-yl)-bicyclo[2.2.1]heptane, 2-(4,6-diamino-1,3,5-triazin-2-yl)-6-[4,6-bis(4-methoxycarbonylphenylamino)-1,3,5-triazin-2-yl]-bicyclo[2.2.1]heptane, 1,4-bis(4-amino-6-n-decylamino-1,3,5-triazin-2-yl)-cyclohexane, 1,3-bis[4-amino-6-(2-morpholinoethylamino)-1,3,5-triazin-2-yl)-cyclohexane, 1-(4,6-diamino-1,3,5-triazin-2-yl)-2-(4,6-dianilino-1,3,5-triazin-2-yl)-cyclohexane, 2,5-bis[4-amino-6-(2-hydroxyethylamino)-1,3,5-triazin-2-yl]-bicyclo[2.2.1]heptane, 2,6-bis[4-amino-6-(2-hydroxypropylamino)-1,3,5-triazin-2-yl]-bicyclo[2.2.1]heptane, 2,5-bis[4-amino-6-(5-hydroxy-3-oxapentylamino)-1,3,5-triazin-2-yl]-bicyclo[2.2.1]heptane, 2,5-bis[4-amino-6-(4-hydroxyphenylamino)-1,3,5-triazin-2-yl]-bicyclo[2.2.1]heptane, 2-(4,6-diamino-1,3,5-triazin-2-yl)-6-[4,6-bis(2-hydroxyethylamino)-1,3,5-triazin-2-yl]-bicyclo[2.2.1]heptane, 1,4-bis[4-amino-6-(2-hydroxyethylamino)-1,3,5-triazin-2-yl)-cyclohexane, 1,3-bis[4-amino-6-(3-hydroxypropylamino)-1,3,5-triazin-2-yl]-cyclohexane, 1-(4,6-diamino-1,3,5-triazin-2-yl)-4-[4,6-bis(5-hydroxy-3-oxapentylamino)-1,3,5-triazin-2-yl]-cyclohexane, 2-(4-amino-6-cyclohexylamino-1,3,5-triazin-2-yl)-5-[4,6-bis(cyclohexylamino)-1,3,5-triazin-2-yl]-bicyclo[2.2.1]heptane, 2-[4-amino-6-(2-morpholinoethylamino)-1,3,5-triazin-2-yl]-6-[4,6-bis(2-morpholinoethylamino)-1,3,5-triazin-2-yl]-bicyclo[2.2.1]heptane, 1-[4-amino-6-(4-ethoxycarbonylphenylamino)-1,3,5-triazin-2-yl]-4-[4,6-bis(4-ethoxycarbonylphenylamino)-1,3,5-triazin-2-yl]-cyclohexane, 2-[4-amino-6-(2-hydroxyethylamino)-1,3,5-triazin-2-yl]-6-[4,6-bis(2-hydroxyethylamino)-1,3,5-triazin-2-yl]-bicyclo[2.2.1]heptane, 2-[4-amino-6-(2-hydroxypropylamino)-1,3,5-triazin-2-yl]-5-[4,6-bis(2-hydroxypropylamino)-1,3,5-triazin-2-yl]-bicyclo[2.2.1]-heptane, 2-[4-amino-6-(2-hydroxyethylamino)-1,3,5-triazin-2-yl]-5-[4,6-bis(5-hydroxy-3-oxapentyl)-1,3,5-triazin-2-yl]-bicyclo[2.2.1]heptane, 2-[4-amino-6-(5-hydroxy-3-oxapentylamino)-1,3,5-triazin-2-yl]-6-[4,6-bis(5-hydroxy-3-oxapentylamino)-1,3,5-triazin-2-yl]bicyclo[2.2.1]heptane, 2-[4-amino-6-(4-hydroxyphenylamino)-1,3,5-triazin-2-yl]-5-[4,6-bis(4-hydroxyphenylamino)-1,3,5-triazin-2-yl]-bicyclo[2.2.1]heptane, 2-[4-amino-6-anilino-1,3,5-triazin-2-yl]-6-[4,6-bis(3-hydroxypropylamino)-1,3,5-triazin-2-yl]-bicyclo[2.2.1]heptane, 1-[4-amino-6-(2-hydroxyethylamino)-1,3,5-triazin-2-yl]-4-[4,6-bis(2-hydroxyethylamino)-1,3,5-triazin-2-yl]-cyclohexane, 1-[4-amino-6-(1-hydroxymethylpropylamino)-1,3,5-triazin-2-yl]-3-[4,6-bis(1-hydroxymethylpropylamino)-1,3,5-triazin-2-yl]cyclohexane, 1-[4-amino-6-(5-hydroxy-3-oxapentylamino)-1,3,5-triazin-2-yl]-4-[4,6-bis(5-hydroxy-3-oxapentylamino)-1,3,5-triazin-2-yl]-cyclohexane, 1-[4-amino-6-(4-amino-6-(4-hydroxyphenylamino)-1,3,5-triazin-2-yl]-2-[4,6-bis(4-hydroxyphenylamino)-1,3,5-triazin-2-yl]cyclohexane, 2,5-bis[4,6-bis(n-octylamino)-1,3,5-triazin-2-yl]-bicyclo[2.2.1]heptane, 2,6-bis[4,6-bis-(cyclohexylamino)-1,3,5-triazin-2-yl]-bicyclo[2.2.1]-heptane, 2,5-bis[4,6-dianilino-1,3,5-triazin-2-yl]-bicyclo[2.2.1]heptane, 2,5-bis[4,6-bis(2-morpholinoethylamino)-1,3,5-triazin-2-yl]-bicyclo[2.2.1]heptane, 2,6-bis[4,6-bis(3-oxapentylamino)-1,3,5-triazin-2-yl]-bicyclo[2.2.1]heptane, 2,5-bis[4,6-bis(4-methoxycarbonylphenylamino)-1,3,5-triazin-2-yl]-bicyclo[2.2.1]heptane, 1,3-bis[4,6-bis(cyclohexylamino)-1,3,5-triazin-2-yl]-cyclohexane, 1,4-bis[4,6-bis(2-morpholinoethylamino)-1,3,5-triazin-2-yl]-cyclohexane, 1,2-bis[4,6-bis(3-oxapentylamino)-1,3,5-triazin-2-yl]-cyclohexane, 1,4-bis[4,6-bis(4-ethoxycarbonylphenylamino)-1,3,5-triazin-2-yl]-cyclohexane, 2,5-bis[4,6-bis(2-hydroxyethylamino)-1,3,5-triazin-2-yl]-bicyclo[2.2.1]heptane, 2,6-bis[4,6-bis(2-hydroxypropylamino)-1,3,5-triazin-2-yl]-bicyclo[2.2.1]heptane, 2,6-bis[4,6-bis(1-hydroxymethylpropylamino)-1,3,5-triazin-2-yl]bicyclo[2.2.1]heptane, 2,5-bis[4,6-bis(3-hydroxypropylamino)-1,3,5-triazin-2-yl]-bicyclo[2.2.1]heptane, 2,5-bis[4,6-bis(5-hydroxy-3-oxapentylamino)-1,3,5-triazin-2-yl]-bicyclo[2.2.1]heptane, 2,6-bis[4,6-bis(5-hydroxy-3-oxapentylamino)-1,3,5-triazin-2-yl]-bicyclo[2.2.1]heptane, 2,6-bis[4,6-bis(4-hydroxyphenylamino)-1,3,5-triazin-2-yl]-bicyclo[2.2.1]heptane, 2,5-bis[4,6-bis(N,N-di-n-butylamino)-1,3,5-triazin-2-yl]-bicyclo[2.2.1]heptane, 1,3-bis[4,6-bis(2-hydroxyethylamino)-1,3,5-triazin-2-yl]-cyclohexane, 1,4-bis[4,6-bis(2-hydroxypropylamino)-1,3,5-triazin-2-yl]-cyclohexane, 1,2-bis[4,6-bis(1-hydroxymethylpropylamino)-1,3,5-triazin-2-yl]-cyclohexane, 1,4-bis[4,6-bis(3-hydroxypropylamino)-1,3,5-triazin-2-yl]-cyclohexane, 1,3-bis[4,6-bis(5-hydroxy-3-oxapentylamino)-1,3,5-triazin-2-yl]-cyclohexane, 1,4-bis[4,6-bis(4-hydroxyphenylamino)-1,3,5-triazin-2-yl]-cyclohexane, polyoxyethylenated 2,5-bis[4,6-diamino-1,3,5-triazin-2-yl]-bicyclo[2.2.1]heptane, polyoxypropylenated 2,6-bis[4,6-diamino-1,3,5-triazin-2-yl]-bicyclo[2.2.1]heptane, polyoxyethylenated 2-[4,6-diamino-1,3,5-triazin-2-yl]-6-[4-amino-6-anilino-1,3,5-triazin-2-yl]-bicyclo[2.2.1]heptane, polyoxyethylenated 2,6-bis[4-amino-6-(2-hydroxypropylamino)-1,3,5-triazin-2-yl]-bicyclo[2.2.1]heptane, polyoxypropylenated 2-[4-amino-6-(2-hydroxyethylamino)-1,3,5-triazin-2-yl]-5-[4,6-bis(2-hydroxyethylamino)-1,3,5-triazin-2-yl-bicyclo[2.2.1]heptane, polyoxyethylenated 2,6-bis[4,6-bis(5-hydroxy-3-oxapentylamino)-1,3,5-triazin-2-yl]-bicyclo[2.2.1]heptane, polyoxyethylenated 2,5-bis[4,6-bis(2-hydroxypropylamino)-1,3,5-triazin-2-yl]-bicyclo[2.2.1]heptane, polyoxypropylenated 2,6-bis[4,6-bis(4-hydroxyphenylamino)-1,3,5-triazin-2-yl]-bicyclo[2.2.1]heptane, polyoxyethylenated 2,5-bis[4,6-bis(N,N-dimethylolamino)-1,3,5-triazin-2-yl]-bicyclo[2.2.1]heptane, polyoxypropylenated 2,6-bis[4,6-bis(N-methylolamino)-1,3,5-triazin-2-yl]-bicyclo[2.2.1]heptane, polyoxyethylenated 1,4-bis(4,6-diamino-1,3,5-triazin-2-yl)-cyclohexane, polyoxypropylenated 1,3-bis(4,6-diamino-1,3,5-triazin-2-yl)-cyclohexane, polyoxystyrenated 1-[4,6-diamino-1,3,5-triazin-2-yl)-2-(4-amino-6- benzylamino-1,3,5-triazin-2-yl)-cyclohexane, polyoxypropylenated 1,4-bis[4,6-bis(2-hydroxypropylamino)-1,3,5-triazin-2-yl)-cyclohexane, polyoxyethylenated 1,3-bis[4,6-bis(4-hyroxyphenylamino)-1,3,5-triazin-2-yl]-cyclohexane, polyoxyethylenated 1,4-bis[4,6-bis-(N,N-dimethylolamino)-1,3,5-triazin-2-yl]-cyclohexane, polyoxypropylenated 1,3-bis[4,6-bis(N-methylolamino)-1,3,5-triazin-2-yl)-cyclohexane, 2-(4,6-diamino-1,3,5-triazin-2-yl)-5-[4-amino-6-(2-piperazinoethylamino)-1,3,5-triazin-2-yl]-bicyclo[2.2.1]heptane, 2,6-bis[4,6-bis(2-aminoethylamino)-1,3,5-triazin-2-yl]-bicyclo[2.2.1]heptane, 2,5-bis[4,6-bis(2-piperidinoethylamino)-1,3,5-triazin-2-yl]-bicyclo[2.2.1]heptane, 2,6-bis[4,6-bis(3-piperazinopropylamino)-1,3,5-triazin-2-yl]-bicyclo[2.2.1]heptane, 2,5-bis[4,6-bis(N-aminoethylpiperazinoethylamino)-1,3,5-triazin-2-yl]-bicyclo[2.2.1]heptane, 1,3-bis[4,6-bis(2-piperazinoethylamino)-1,3,5-triazin-2-yl]-cyclohexane, and 1,4-bis[4,6-bis(3-piperidinopropylamino)-1,3,5-triazin-2-yl]-cyclohexane.

Among the above-described diguanamine derivatives according to the present invention, preferred are hydroxyl-containing diguanamine derivatives in which $Y_1, Y_2, Y_3, Y_4, Y_5, Y_6, Y_7$ and $Y_8$ in formula (11) or (12) individually represent a substituent selected from the group consisting of a hydrogen atom and groups represented by HO—$Y_9$—, $Y_9$ being a divalent group containing at least two carbon atoms.

Also preferred are hydroxyl-containing diguanamine derivatives in which HO—$Y_9$— is a group selected from the group consisting of 2-hydroxyethyl, 2-hydroxypropyl, 1-hydroxymethylpropyl, 3-hydroxypropyl, 5-hydroxy-3-oxapentyl and 4-hydroxyphenyl groups.

Also preferred are oxaalkyl-containing diguanamine derivatives represented by formula (11) or (12) in which at least one of $Y_1, Y_2, Y_3, Y_4, Y_5, Y_6, Y_7$ and $Y_8$ represents a group selected from the group consisting of groups represented by formula (13) or (14). More preferably, $Y_{10}$ in formula (13) or (14) is at last one group selected from ethylene and propylene.

Each diguanamine derivative represented by formula (11) or (12) can be prepared by reacting at least one diguanamine, which is selected from the diguanamines represented by formula (1) or (2), with at least one amine selected from amines containing one or more amino groups and at least two carbon atoms.

As the amine for the above-described preparation of the diguanamine derivative, any amine can be used insofar as it contains at least one amino group and two or more carbon atoms. No particular limitation is imposed on the number of amino group(s). The amine contains an aliphatic, alicyclic, aromatic or heterocyclic group having two or more carbon atoms. Although no other particular limitation is imposed on the amines, those containing 2–20 carbon atoms are preferred for the availability of raw materials, the readiness of reactions, and the simpleness and convenience of steps such as purification and isolation. The amine may contain one or more groups other than amino group(s), for example, hydroxyl, ester, ether, carboxyl, carbonyl, amido, imido, sulfonic, carboxamido, imino and/or unsaturated groups. Those containing one or more hydroxyl, ester, ether and/or imino groups are particularly useful.

Specific examples of such amines include, but are not limited to, compounds represented by HO—$Y_9$—$NH_2$ in which $Y_9$ represents a divalent group containing at least two carbon atoms, such as 2-aminoethanol, 3-amino-1-propanol, 2-amino-1-propanol, 1-amino-2-propanol, 4-amino-1-butanol, 2-amino-1-butanol, 1-amino-2-methyl-2-propanol, 5-amino-1-pentanol, 3-amino-1-pentanol, 1-amino-3-pentanol, 2,2-dimethyl-3-amino-1-propanol, 6-amino-1-hexanol, 4-amino-2-hexanol, 8-amino-1-octanol, 10-amino-1-decanol, 12-amino-1-dodecanol, 3-amino-1-penten-5-ol, 4-amino-2-hexen-6-ol, 3-amino-1-hexen-5-ol, 5-amino-2-octen-6-ol, 5-amino-3-oxapentan-1-ol, 2-amino-3-methoxy-1-propanol, 3-amino-5-ethoxy-1-pentanol, 4-amino-7-methoxy-2-heptanol, 4-amino-1-cyclohexanol, p-aminophenol, 4-amino-m-cresol, p-aminophenyl ethanol, 8-amino-2-naphthol, p-aminobenzyl alcohol, 4-hydroxyphenethylamine, 2-amino-3-hydroxypyridine and 5-amino-8-hydroxyquinoline; aliphatic monoamines such as ethylamine, isopropylamine, butylamine, 1,2-dimethylpropylamine, hexylamine, 2-ethylhexylamine, dodecylamine, tetradecylamine, hexadecylamine, octadecylamine, allylamine, oleylamine, 3-ethoxypropylamine, propoxypropylamine, butoxypropylamine, 2-ethylhexyloxypropylamine and myristyloxypropylamine; aromatic monoamines such as aniline, o-toluidine, α-naphthylamine, β-phenethylamine and benzylamine; alicyclic monoamines such as cyclohexylamine and 4-methylcyclohexylamine; heterocyclic monoamines such as furfurylamine, N-(2-aminoethyl)morpholine, N-(2-aminoethyl)piperidine, N-(3-aminopropyl)piperazine and 2-aminopyridine; polyamines such as 1,2-ethylenediamine, 1,3-diaminopropane, 1,2-diaminopropane, 1,4-butylenediamine, 1,6-hexamethylenediamine, 1,4-diaminocyclohexane, 1,3-bis(aminomethyl)cyclohexane, N-(2-aminoethyl)piperazine, N,N'-bis(2-aminoethyl)piperazine, m-phenylenediamine, benzidine, 4,4'-diaminodiphenylmethane, xylylenediamine and 1,2-bis(3-aminopropoxy)ethane; alkyl aminobenzoates such as ethyl p-aminobenzoate, methyl anthranylate and butyl m-aminobenzoate; and polyalkylenepolyamines such as diethylenetriamine, triethylenetetramine, tetraethylenepentamine and pentaethylenehexamine. The compounds represented by HO—$Y_9$—$NH_2$ are particularly preferred as they can provide hydroxyl-containing diguanamine derivatives useful for a wide variety of applications. The proportion of an amine to be used can be chosen freely as needed. It is generally used in a proportion of 0.5–20 moles, preferably 1–16 moles per mole of the diguanamine. When an amine which tends to form byproducts such as cyclized compounds, such as 1-aminoethanol, is used, it is preferred to conduct the reaction by using the amine in a proportion of 8 moles or greater per mole of the corresponding diguanamine to reduce byproduction. Use of the amine in an unduly large excess tends to develop a reduction in reaction velocity. In such a case, it is therefore preferred to choose and take a suitable measure, for example, to conduct the reaction by adding the amine either continuously or discontinuously into the reaction system.

The above reaction can generally conducted at 120°–250° C., preferably 150°–200° C. in the presence of an acidic catalyst.

Useful as the acidic catalyst is a compound or the like, which releases or forms protons under reaction conditions. Illustrative acidic catalysts include, but are not limited to, mineral acids such as hydrofluoric acid, hydrochloric acid, hydrobromic acid, sulfuric acid and phosphoric acid; sulfonic acids such as amidosulfonic acid, thiocyanic acid, p-toluenesulfonic acid and methanesulfonic acid; carboxylic acids such as trifluroacetic acid and trichloroacetic acid; salts of such acids with diguanamines, amines, ammonia or the like; and Lewis acids such as boron trifluoride, aluminum chloride, tin (IV) chloride, antimony (V) fluoride and iron (III) bromide. The proportion of the acidic catalyst to be used can be chosen freely as needed. However the acidic catalyst is generally used at a ratio of 0.05–5.0 moles, preferably 0.1–2.0 moles per mole of the corresponding diguanamine.

The above reaction can be conducted in the presence or absence of a solvent. It is preferred to carry out the reaction in the absence of any solvent. In some instances, however, a solvent can be chosen as needed, for example, from 1-pentanol, 2-methyl-1-butanol, 1-hexanol, 3-heptanol, 1-octanol, 2-ethyl-1-hexanol, 1-decanol, ethylene glycol, 1,2-propylene glycol, diethylene glycol, triethylene glycol, 2-methyl-2,4-pentanediol, ethylene glycol diethyl ether, ethylene glycol dibutyl ether, ethylene glycol monobutyl ether, diethylene glycol dimethyl ether, diethylene glycol dibutyl ether, diethylene glycol monomethyl ether, diethylene glycol monoethyl ether, diethylene glycol monobutyl ether, triethylene glycol dimethyl ether and triethylene glycol monoethyl ether.

No particular limitation is imposed on a system for the above reaction. It is however preferred to conduct the reaction in the presence of a gas inert to the reaction such as nitrogen or argon because the inert gas is effective, for example, in reducing coloration of the reaction product. The reaction can be conducted under normal pressure or under naturally-occurring pressure or elevated pressure within a closed vessel. These reaction conditions can be chosen freely as needed.

The hydroxyl-containing or oxaalkyl-containing diguanamine derivatives according to the present invention can each be prepared by subjecting at least one diguanamine or diguanamine derivative—which is selected from the group consisting of the diguanamine derivatives containing an active hydrogen atom and represented by formula (11) or (12), diguanamines represented by formula (1) or (2) and N-methylol derivatives of diguanamine—and at least one epoxide to an addition reaction.

The above process is excellent because it can easily provide in a high yield the hydroxyl-containing diguanamine derivatives and the oxaalkyl-containing diguanamine derivatives, the latter derivatives containing at least one group selected from the group consisting of groups represented by formula (13) or (14).

As such diguanamine derivatives, those having an active-hydrogen-containing group such as an imino, amino or hydroxyl group are all useful. Useful examples of such diguanamine derivatives include, but are not limited to, diguanamine derivatives and hydroxyl-containing diguanamine derivatives, which are obtained by reacting diguanamine represented above formula (1) or (2) with amino-containing compounds having two or more carbon atoms such as aliphatic monoamines, alicyclic monoamines, aromatic monoamines, polyamines, compounds represented by HO—$Y_9$—$NH_2$, $Y_9$ being a divalent group containing at least two carbon atoms, and the like, with hydroxyl-containing diguanamine derivatives being preferred. Such diguanamine derivatives are particularly preferred, as they have excellent features that their reactions can be carried out substantially in the absence of any solvent, they can be obtained in a high yield as good reaction products having a narrow molecular weight distribution and high purity, and their preparation steps such as purification and isolation are simple.

As diguanamines, the compounds represented above by formula (1) or (2) are all useful. These compounds have excellent features absolutely unpredictable from the known technology, that is, advantageous features such that they have far better solubility in solvents compared with melamines, their reactions can be carried out smoothly under milder conditions, and good products can be obtained with a desired molecular weight and a narrow molecular weight distribution than those available from the melamine. These diguanamines are therefore extremely useful as raw materials for the preparation of the derivatives described above.

As N-methylol derivatives of diguanamines, those containing an N-methylol group and derived from the above-described diguanamines are all useful. Illustrative N-methylol derivatives of diguanamines include, but are not limited to, N-methyloldiguanamines obtained by subjecting the above-described diguanamines and aldehydes such as formaldehyde to addition reactions, respectively, etherified diguanamines by subjecting such N-methyloldiguanamines and alcohols having 1–20 carbon atoms to etherification, and primary condensates of N-methyloldiguanamine and primary condensates of etherified diguanamine obtained by subjecting such N-methyloldiguanamines and etherified diguanamines to condensation, respectively. Preferred are N-methyloldiguanamines and primary condensates of N-methyloldiguanamine, with N-methyloldiguanamines being particularly preferred. Such N-methylol derivatives of diguanamines have advantageous features extremely difficult to obtain with melamines and are preferred, as they are excellent inter alia in that their reactions can be conducted substantially in the absence of any solvent, they can be obtained as good products having a narrow molecular weight distribution, their preparation steps such as purification and isolation are simple, polyols having eight hydroxyl groups can be easily obtained, and their yields are good.

As epoxides usable for the preparation of the diguanamine derivatives described above, alkylene oxides containing one or more aliphatic groups, alicyclic groups, aromatic groups having 2–22 carbon atoms and/or the like are useful. Illustrative of such epoxides include, but are not limited to, ethylene oxide, propylene oxide, butylene oxide, isoprene oxide, n-hexene oxide, cyclohexene oxide, styrene oxide, cyclopentadiene monoxide, allyl glycidyl ether, n-butyl glycidyl ether, phenyl glycidyl ether, glycidyl methacrylate and butadiene oxide, with ethylene oxide and propylene oxide being preferred. These epoxides can be used either singly or in combination as mixtures. It is also possible to use them in such a way that one of such epoxides is reacted, followed by reaction of another one. No particular limitations are imposed on the selection of these epoxides and the manner of the reaction such as the charging method and sequence. The proportion of the epoxide can be chosen freely as needed. However, the epoxide can be used generally in an amount of 1–200 moles, preferably 2–100 moles, more preferably 4–20 moles per mole of the total amount of the diguanamine derivative, diguanamine and/or N-methyloldiguanamine derivative.

The above reaction is generally conducted at 80°–200° C., preferably 100°–150° C. in the presence of a basic catalyst.

Examples of the basic catalyst include, but are not limited to, alkali metal hydroxide and alkaline earth metal hydroxides such as lithium hydroxide, potassium hydroxide, sodium hydroxide and calcium hydroxide; and alkali metal alcoholates such as sodium methylate, sodium ethylate and potassium ethylate. The proportion of the basic catalyst to be used can be chosen freely as needed. However, the basic catalyst can be used generally in an amount of 0.01–1.0 mole, preferably 0.05–0.5 mole per mole of the total amount of the diguanamine derivative, diguanamine and/or N-methyloldiguanamine derivative.

The above reaction can be conducted in the presence or absence of a solvent, with the reaction in the absence of any solvent being preferred. Nevertheless, it is possible to choose and use a solvent as desired depending on the raw materials, reaction conditions and the like. Any compound can be used as a solvent as long as it is inert to the reaction. Examples of the solvent include, but are not limited to, aprotonic polar solvents such as ethers, dialkyl sulfoxides, alkyl-substituted acid amides and sulforans; esters; and ketones. Of these, ethers and aprotonic polar solvents are preferred.

Further, the above reaction can be conducted under normal pressure or under naturally-occurring pressure or elevated pressure within a closed vessel. These reaction conditions can be chosen freely as needed.

Each of the hydroxyl-containing diguanamine derivatives and oxaalkyl-containing diguanamine derivatives according to the present invention can also be obtained by reacting the corresponding diguanamine of formula (1) or (2) with the corresponding alkylene carbonate such as ethylene carbonate, propylene carbonate or 1,2-butylene carbonate at 75°–250° C. in the presence or absence of a solvent while using a basic catalyst such as potassium carbonate, sodium carbonate, caustic potash, caustic soda or pyridine.

The diguanamine derivatives according to the present invention can be obtained by any one of the preparation processes described above, although their preparation is not limited to these processes.

In the above process for the preparation of the diguanamine derivatives of this invention, the amine is preferably a compound represented by the following formula:

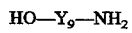

wherein $Y_9$ has the same meaning as defined above.

The compound represented by the formula HO—$Y_9$—$NH_2$ is preferably a compound selected from the group consisting of 2-aminoethanol, 1-aminopropan-2-ol, 2-aminobutan-1-ol, 3-aminopropan-1-ol, 5-amino-3-oxapentan-1-ol and 4-aminophenol.

In the above preparation process, it is preferred to subject at least one of the above diguanamine derivatives and at lease one of the above epoxides to an addition reaction.

It is also preferred to subject at least one diguanamine, which is selected from diguanamines represented by formula (1) or (2), and at least one of the above epoxides to an addition reaction. More preferably, said at least one epoxide is selected from ethylene oxide or propylene oxide.

The diguanamine derivatives according to the present invention are useful for an extremely wide variety of applications as modifiers such as flame retardants, heat resistance improvers, abrasion resistance improvers, thermal stabilizers and compatibilizing agents for resins and, since they are excellent in the polymerizability and reactivity with various compounds such as isocyanates, aldehydes, epoxides and carboxylic acids, as resin raw materials, derivative raw materials, curing agents, chain extenders, crosslinking agents and the like, which can provide resins and derivatives excellent in heat resistance, flame retardancy, flexibility, toughness and the like. They can provide, for example, flame-retardant resin compositions, polyurethane resin compositions, amino resin compositions, polyester resin compositions and the like, all of which have superb properties.

The diguanamine derivatives according to the present invention can provide a method for making a resin retardant to flame, which comprises incorporating 3–50 wt. %, based on the resin, of at least one diguanamine derivative selected from the diguanamine derivatives described above in the resin. It has also been found that combined use of the diguanamine derivative with at least one substance selected from phosphoruses, isocyanuric acids and cyanuric acids or with an amino-containing compound can provide a flame-retarding method for a resin, which method makes it possible to obtain still improved flame retardancy owing to synergistic effects. Resin compositions which can be obtained by such flame-retarding methods are useful in a wide variety of industrial fields such as construction materials, electrical materials, materials for vehicles such as automotive vehicles, fiber materials and household goods.

The above-described diguanamine derivatives, like the diguanamines described above, are useful in the flame retardation of resins. Conditions which are adopted upon employment of the diguanamine derivatives for the above application, for example, conditions for their combined use with other additives, their proportions in resin compositions, applicable resins and the like are similar to those set out above for the diguanamines. Some of such conditions will next be summarized below by way of example.

The amount of the diguanamine derivative to be used can be chosen freely as desired. However, it can be used generally in an amount of 3–50 wt. %, preferably 4–40 wt. % based on the resin.

As the phosphoruses, simple substances of phosphorus and phosphorus-containing compounds are both useful. Illustrative examples include, but are not to be limited to, red phosphorus; phosphoric acids such as phosphoric acid, polyphosphoric acid, phosphorous acid and phosphonic acid; salts obtained by partially or fully neutralizing these phosphoric acids with bases such as ammonia, amine, alkali metals and alkaline earth metals; phosphoric mono-, di- and tri-esters which may optionally contain one or more halogen atoms; salts of acidic phosphate esters with ammonia, amines, melamine, alkali metals and alkaline earth metals; phosphite esters such as phosphorous triesters and phosphorous diesters; phosphonate esters such as phosphonates esters, acidic phosphonate esters and salts thereof; phosphines such as phosphine, phosphine oxide and phosphonium salts; and sulfur-containing phosphorus compounds such as dialkylthiophosphoric acids and salts thereof. Preferred are polyammonium phosphates represented by formula $(NH_4)_{n+2}P_nO_{3n+1}$, n being an integer greater than 5, "Exolit 263" and "Exolit 422", trade names; products of Hoechst AG, phosphate esters and the like. The amount of the phosphorus to be used is generally 5–40 wt. %, preferably 10–30 wt. % based on the resin.

Illustrative isocyanuric acids and cyanuric acids include, but are not limited to, isocyanuric acid, trimethyl isocyanurate, tris(2-hydroxyethyl) isocyanurate, triphenyl isocyanurate, cyanuric acid, trimethyl cyanurate, tris(2-hydroxyethyl) cyanurate, diphenyl cyanurate, triphenyl cyanurate, dimethyl phenyl cyanurate, and triglycidyl cyanurate. The amount of the isocyanuric acids or cyanuric acids to be used can be chosen freely as needed. In general, they can however be used in an amount of 0.02–10 moles per mole of the above-described diguanamine derivative.

When at least one compound selected from the above-described amino-containing compounds is additionally used and incorporated in a resin, the flame retardancy of the resin can be improved further. The combined use of such an amino-containing compound is therefore preferred. The amount of the amino-containing compound can be chosen freely as needed. In general, it can however be used in an amount of 0.01–10 wt. % based on the resin.

Further, it is particularly preferred to incorporate the above-described phosphorus and amino-containing compound as flame-retarding aids in a resin.

The diguanamine derivatives described above can each be prepared by reacting at least one diguanamine, which is selected from those represented by formula (1) or (2), with at least one amine. Use of a compound containing two or more amino groups as such an amine can provide a diguanamine polymer depending on reaction conditions.

A flame-retarding method for a resin, which features incorporating in the resin such a diguanamine polymer in an amount of 3–50 wt. % based on the resin, can also substantially improve the flame retardancy of the resin like the above-described diguanamine derivatives, so that the flame-retarding method is extremely useful.

Each of the above-described diguanamine derivatives, when incorporated in an amount of 0.01–5 wt. % based on a resin, can significantly improve the thermal stability and ultraviolet light resistance of the resin and can minimized coloration or discoloration of the resin during its processing or forming at high temperatures. Such diguanamine derivatives are excellent in high-temperature stability and non-volatility and feature easy handling, so that they can provide an excellent thermal stabilization method for resins.

According to such a thermal stabilization method of a resin, the diguanamine derivative can be used generally in an amount of 0.01–5 wt. %, preferably 0.02–1 wt. % based on the resin.

Resins to which the thermal stabilization method of the present invention can be applied are approximately the same as the-above described resins to which the above-described flame retarding method can be applied.

These resins are preferably thermoplastic resins. At least one resin selected from the group consisting of polyphenylene ether resins, polyacetal resins, polyamide resins and polyolefin resins is more preferred. A still more preferred polyolefin resin is at least one resin selected from the group consisting of polyethylene resin, polypropylene resin and ethylene-propylene copolymers.

In the thermal stabilization method of such a resin, production of the resin composition and use of a phenolic antioxidant, an amine-base antioxidant, a sulfur-containing antioxidant, a light stabilizer, a nucleating agent, a phosphite antioxidant and/or other additives can be conducted, but are not limited to, in a similar manner to the above-described flame-retarding method.

The present invention can also provide a method for compatibilizing resins, which comprises incorporating the above-described diguanamine derivative in a blend of at least two resins of different types containing at least one resin selected from polyamide resins, polyphenylene ether resins, polyimide resins and polyaramid resins.

The above compatibilization method is excellent, because it can substantially improve the compatibility of said at least two resins of different types and, moreover, can reduce coloration or discoloration of the blend during its processing or forming at high temperatures, and the derivative has excellent high-temperature stability, does not undergo much sublimation, bleeding or the like and permits easy handling and has good dispersibility in melts of the polyamide resins, polyphenylene ether resins and the like.

In the resin compatibilization method according to the present invention, the diguanamine derivative can be used generally in an amount of 0.5–20 wt. % based on the total amount of the resins. Its amount can be chosen freely as needed depending on the case.

As resins to which the resin compatibilization method of this invention can be applied, resins to which the above flame-retarding method is applicable can be mentioned likewise. Specific examples of the at least two resins of different types include, but are not limited to, one resin selected from polyamide resins, polyphenylene ether resins, polyimide resins and polyaramid resins and other resins, for example, a polyamide resin and ABS resin; a polyamide resin and a polyphenylene ether resin; and a polyimide resin and a polyphenylene ether resin; a polyamide resin, polyphenylene ether resin and other resins.

In the compatibilization method of such resins, production of the resin composition and use of a phenolic antioxidant, an amine-base antioxidant, a sulfur-containing antioxidant, a light stabilizer, a nucleating agent, a phosphite antioxidant and/or other additives can be conducted, but are not limited to, in a similar manner to the above-described flame-retarding method.

The diguanamine derivatives according to the present invention can each provide a polyurethane resin composition which comprises a polyol component and an organopolyisocyanate component. The polyol component contains at least one diguanamine derivative selected from the above-described hydroxyl-containing diguanamine derivatives and oxaalkyl-containing diguanamine derivatives. Such a resin composition can provide a material having excellent properties, for example, excellent mechanical properties such as flame retardancy, heat resistance, water resistance, abrasion resistance, flexibility, toughness and elasticity. The resin composition is useful for a wide variety of applications, for example, as soft and hard polyurethane foams, paints, adhesives, plasticizers, sealants, caulking agents, film-waterproofing agents, floorings, polyurethane resin concretes, fiber treatments, sheets, films, rolls, tires, vibration-deadening materials, belts, tubes, diaphragms, air brakes, soles, artificial leathers and elastic fibers. In particular, soft and hard polyurethane foams are useful. It is to be noted that the resin composition is not limited to such applications.

Illustrative specific embodiments of such applications include, but are not limited to, preparation of a foaming polyurethane resin composition comprising the above-described polyol component and organopolyisocyanate component, a foaming agent and a catalyst, followed by the production of polyurethane foam from the resin composition.

As an essential component of the polyol component, any derivative is useful as long as it has been derived from one of the above-described diguanamines and containing one or more hydroxyl groups. Examples of such derivatives include the above-described hydroxyl-containing diguanamine derivatives and oxaalkyl-containing diguanamine derivatives. The number of hydroxyl group(s), the molecular weight, the type of the epoxide, the manner of addition, etc. can be chosen freely as desired. Incidentally, the polyol component may include one or more polyols other than the above-described essential component to an extent not impairing the effects of the present invention. Illustrative examples of such additional polyols include, but are not limited to, water; alkylene oxide adducts such as ethylene glycol, trimethylolpropane, glycerin, pentaerythritol, sorbitol and sugar; and alkylene oxide adducts such as polyester polyols, acrylic polyols, butadiene polyols, phenolic polyols, halogen-containing polyols, phosphor-containing polyols, tris(2-hydroxyethyl) isocyanurate and tris(2-hydroxyethyl) melamine.

Exemplary organopolyisocyanate components include, but are not limited to, 2,4-(2,6-)tolylene diisocyanate, diphenylmethane-4,4'-diisocyanate, 2,2'-dimethylphenylmethane-4,4'-diisocyanate, biphenyl-4,4'-diisocyanate, 1,5-nephthalene diisocyanate, tolidine diisocyanate, isophorone diisocyanate, p-phenylene diisocyanate, cyclohexane-1,4-diisocyanate, hexamethylene diisocyanate, xylylene diisocyanate, hydrogenated xylylene diisocyanate, hydrogenated diphenyl methane-4,4'-diisocyanate, lysine diisocyanate, triphenylmethane triisocyanate, tris(isocyanate phenyl) thiophosphate, tetramethylxylene diisocyanate, lysine ester triisocyanates, 1,6,11-undecanetriisocyanate, 1,8-diisocyanato-4-isocyanatomethyloctane, 1,3,6-hexamethylene triisocyanate, trimethylhexamethylene diisocyanate, azobenzene-4,4'-diisocyanate, 2-nitrobiphenyl-4,4'-diisocyanate, and diphenylsulfone-4,4'-diisocyanate; and modified products, derivatives and the like of such isocyanates, such as their block isocyanates, isocyanate prepolymers, urethane adducts and isocyanurates.

The amount of the organopolyisocyanate to be used can be chosen freely as needed. However, it is generally used in an amount equivalent to the hydroxyl number of the associated polyol component or in an amount greater or smaller than the equivalent amount.

In the above-described foaming polyurethane resin composition, known foaming agents for urethane foams can each be used as a foaming agent. Illustrative of such foaming agents include, but are not limited to, reactive foaming agents such as water, nitroethane, acetaldoxime, formamidoboric acid, diazoaminobenzene and azobisisobutyronitrile; and non-reactive foaming agents such as trichlorofluoromethane, dichlorodifluoromethane and trichlorotrifluoroethane. Examples of the catalyst include, but are not limited to, known amine-base catalysts, organotin catalysts, alkali metal salts and alkali metal alcoholates.

Each diguanamine derivative according to the present invention can provide an amino resin composition characterized in that the amino resin composition comprises a reaction product, which has been obtained by reacting an amino compound including the diguanamine derivative with at least one aldehyde, and at least one resin selected from amino resins obtained by subjecting the above reaction product and alcohols to etherification, respectively. Such a resin composition can provide a material which is excellent in properties such as flame retardancy, heat resistance, flexibility, toughness and elasticity and is hence useful for a wide variety of applications, for example, as elastic foams such as dividing walls (partitions) for buildings, heat insulating materials and soundproofing materials for housings and transportation equipments, warm materials, and impact-resistant packaging materials; general molding for household appliances, automotive parts or components, various machines, and electrical parts and components; laminate forming materials; molding materials for SMC (sheet molding compounds) or BMC (bulk molding compounds); paints; and adhesives.

The present invention also provides polymeric microspheres characterized in that the polymeric microspheres have been obtained by emulsifying an amino resin with a protective colloid, adding a curing agent to the emulsion so formed, and then polymerizing the resultant mixture. The amino resin was obtained by reacting an amino compound containing at least one diguanamine selected from the diguanamines represented by formula (1) or (2) with at least one aldehyde selected from the aldehydes. In addition, the present invention also provides colored polymeric microspheres obtained by coloring the above microspheres with a colorant as well as a method for making a resin retardant to flame, which comprises incorporating 3–50 wt. %, based on the resin, of the uncolored or colored polymeric microspheres.

The proportion of the diguanamine in the polymeric microspheres according to the present invention can be chosen freely depending on the desired properties. To provide an amino resin having good solubility or dispersibility in solvents such as water and also polymer microspheres having excellent heat resistance, solvent resistance, weatherability, impact resistance and abrasion resistance, it is preferred to control the proportion of the diguanamine in an amount of at least 40 wt. % more desirably at last 60 wt. % based on the amino compound. The amino compound can additionally include one or more compounds other than the above-described diguanamines. Illustrative of such compounds include melamine, N-methylmelamine, benzoguanamine, acetoguanamine, cyclohexane carboguanamine, cyclohexene carboguanamine, norbonane carboguanamine, norbornene carboguanamine, dicyandiamide, urea, thiourea, guanidine, urethane, phenol, p-methylphenol, nonylphenol, resoles, aniline, tetramethylenediamine, furfural, furfuryl alcohol, p-toluenesulfonamide, o-toluenesulfonamide, benzenesulfonamide, tetralinsulfonamide, carboxylic amides, sulfuryl amide, and lower polymer of phosphorus diamide nitride. Such additional compounds can be used in any total amount insofar as the significance of the use of the amino compound in the present invention is not impaired, but preferably in a total amount smaller than 60 wt. % of the amino compound.

Examples of the aldehyde usable for the production of the polymeric microspheres according to the present invention include formaldehydes such as formaldehyde, paraformaldehyde, hexamethylenetetramine, methylhemiformal, butylhemiformal and formaldehydesodium bisulfite adduct; glyoxal; acetaldehyde; trimethylol acetaldehyde; acrolein; benzaldehyde; furfural; phthalaldehyde; and terephthaldehyde. Among these, formaldehydes and glyoxal are preferred, with an aqueous solution of formaldehyde and paraformaldehyde being more preferred. Such formaldehyde(s) preferably account for at least 50 wt. % of the aldehyde. The aldehyde can be used generally in an amount of 1.5–16 moles, preferably 2.0–10 moles, more preferably 2.5–6.0 moles per mole of the amino compound.

Although no particular limitation is imposed on the manner of obtaining the amino resin for use in the production of the polymeric microspheres according to the present invention, several processes may be mentioned as examples. A liquid mixture, which has been formed by stirring and mixing the above-described amino compound and aldehyde in one or more solvents such as water, alcohols and/or aromatic compounds, is subjected to an addition reaction at 30°–80° C. and pH 8–13, whereby an N-methyloldiguanamine is obtained. As an alternative, such a liquid mixture is subjected to addition condensation under high alkaline conditions of pH 13 or higher or under conditions of pH 8 or lower, whereby a primary condensate N-methyloldiguanamine is obtained. As a further alternative, the N-methyloldiguanamine or primary condensate N-methyloldiguanamine so obtained is caused to undergo further condensation at pH 1–6 and 30°–80° C. so that a condensate is obtained with a condensation degree increased to an appropriate extent. As a still further alternative, the N-methyloldiguanamine or primary condensate N-methylolguanamine obtained above can be subjected to etherification with an alcohol having 1–20 carbon atoms at pH 1–6 and 30°–90° C. to obtain a partially etherified product. This partially etherified product can also be used as an amino resin in the present invention. Use of such a partially etherified product is generally not preferred, because it tends to result in poor emulsification and/or curing upon production of polymeric microspheres and/or in polymeric microspheres reduced in impact resistance, solvent resistance and the like. Such a partially etherified product may provide polymeric microspheres which are still useful for certain applications. It is to be noted that the manner of obtaining an amino resin useful in the production of polymeric microspheres according to this invention is not limited to the processes exemplified above.

Examples of the protective colloid employed for the production of polymeric microspheres according to the present invention include, but are not limited to, alkali metal salts of polyacrylic acids, alkali metal salts of styrene-maleic acid copolymers, alkali metal salts of isobutylene-maleic acid copolymers, alkali metal salts of p-styrenesulfonic acid polymer, alkali metal salts of sulfonic-acid-modified amino resins, saponified products of vinyl acetate polymers such as polyvinyl alcohol, and polyvinyl pyrrolidone, with saponified products of vinyl acetate polymers being preferred. The amount of the protective colloid to be used can be chosen freely as desired depending on the desired properties, sphere size and the like. In general, however, the protective colloid can be used in an amount of 0.2–25 wt. % preferably 1.0–15 wt. % based on the amino resin. No particular limitation is imposed on the manner of emulsification. Any method useful in emulsifying resins in prior art can be applied. For example, the amino resin can be emulsified by agitating it with a stirring blade in the form of an anchor, a propeller, a turbine or the like or in an agitator such as a colloid mill, dispersion mill or homomixer. It is however to be noted that the emulsification of the amino resin is not limited to the above-exemplified methods.

As the curing agent usable in the production of the polymeric microspheres according to the present invention, any compounds can be used as long as they can release or form protons under production conditions. Illustrative curing agents include, but are not limited to, mineral acids such as hydrochloric acid, sulfuric acid, phosphoric acid and nitric acid; carboxylic acids such as formic acid, benzoic acid, phthalic acid, acetic acid, $\alpha$-chloroacetic acid, trifluoroacetic acid, propionic acid, oxalic acid, lactic acid, amino acids and salicylic acid; sulfonic acids such as benzenesulfonic acid, p-toluenesulfonic acid, o-toluenesulfonic acid and dodecylbenzenesulfonic acid; ammonium salts such as ammonium chloride, ammonium sulfate, ammonium phosphate, ammonium dihydrogenphosphate, diammonium hydrogenphosphate, ammonium nitrate, ammonium formate, ammonium acetate, ammonium p-toluenesulfonate, ammonium sulfamate and diammonium imidosulfonate; chloroacetamides; and water-soluble metal salts of metals such as zinc, magnesium, calcium and aluminum with acids such as nitric acid, sulfuric acid and phosphoric acid, with sulfonic acids being preferred. The curing agent can be used in an amount of 0.01–5 wt. %, preferably 0.05–3 wt. % based on the above-described amino resin. Amounts smaller than 0.01 wt. % lead to insufficient curing and hence to polymeric microspheres reduced in impact resistance, solvent resistance and the like, whereas amounts greater than 5 wt. % can hardly achieve emulsification in a good state. Amounts outside the above range are therefore not preferred.

In the present invention, polymeric microspheres colored with a colorant are also provided. The colorant can be chosen freely depending on the application or the like of the polymeric microspheres. A dye such as a water-soluble dye or an oil-soluble dye, a pigment or the like is useful as the colorant. Illustrative examples of such a colorant include, but are not limited to, basic dyes such as Rhodamine B, Rhodamine 6GCF, Methylviolet B, Aizen Astraphloxine FF, Malachite Green A, Victoria Pure Blue RB and Methylene Turquoise J; acidic dyes such as Acilan Scarlet A, Acid Red XB, Eosine, Lissamine Flavin FF, Alizarine Fast Violet 2RC and Sulforhodamine G; cationic dyes such as Astrazone Pink FG, Astrazone Red 6B, Aizen Cathilon Brilliant Yellow 5GLH and Aizen Cathilon Orange RH; solvent-soluble dyes such as Rhodamine B Base, Azosole Brilliant Yellow 8GF, Azosole Brilliant Yellow 6GF and Azosole Brilliant Blue B; fluorescent brightening dyes such as Uvi-Tex ERN and Tipanol PCR; and pigments such as Heliogen Green 6G and Heliogen Blue LBGM. No particular limitation is imposed on the manner of coloration with such a colorant and any method employed upon coloring resins in prior art or the like can be applied. It is however preferred to add a colorant at a stage from a time point, at which conversion of a product into a hydrophobic form is initiated, to the end of production of polymeric microspheres in the production of the polymeric microspheres. The amino resin can be colored, for example, by adding the colorant in the course of the production of the amino resin or after the completion of the production or by adding the colorant after the amino resin has been emulsified using a protective colloid. It is however to be noted that the manner of coloration is not limited to the methods-exemplified above.

The polymeric microspheres according to the present invention can contain, to an extent not impairing the effects of the present invention, other additives, for example, flame retardants, antistatic agents, antihazing agents, lubricants, fluorescent agents, plasticizers, mildewproofing agents, bacteriocides, antioxidants, ultraviolet light absorbers, fillers, metal inactivating agents and/or the like as needed.

According to the process of the present invention for the production of polymeric microspheres, the polymeric microspheres can be obtained with a desired sphere size, generally of 0.1–20 micrometers, and desired properties. It is also useful to subject the resulting polymeric microspheres to post-treatment, for example, to separate them by filtration, centrifugal separation or the like, followed by water washing, drying and the like, or to subject them to heat treatment at 100°–250° C. for 0.5–5.0 hours. Such post-treatment can be chosen freely depending on the application or the like.

The polymeric microspheres according to the present invention are excellent in heat resistance, solvent resistance, weatherability, abrasion resistance, flame retardancy and the like, and are useful for a wide variety of applications as modifiers, compatibilizing agents or fillers for thermoplastic resins, thermosetting resins and rubbers; blocking preventives for plastic films, cellophane films and inks; abrasion resistance improvers or stress relaxing agents for epoxy resins and phenol resins; flowability improvers for plastics and rubbers; heat resistance improvers, thermal stability improvers, elasticity (e.g., impact resistance) regulating agents or slidability improvers for plastics, films and sheets; viscosity regulating agents for paints, inks and adhesives; paper quality modifiers; dispersibility improvers or anticaking agents for powders; strippable adhesion imparting agents for adhesive tapes and sticking plasters; dispersants or dispersion stabilizers for pigments and the like; delustering agents; powdery lubricants; car waxes; forming aids for sintering materials; concavity/convexity imparting agents; mold release agents; strippability modifiers; transparency and/or gloss improvers for plastics; additives for cosmetics; pigments for cosmetics; scrubbing agents; drying paints; ink conditioners; pressure-sensitive paper conditioners; spacers for liquid crystal panels; special inks for recording materials such as toner; resinous colorants for water-base and oil-base paints; fluorescent paints; traffic paints; resinous colorants for printing inks such as gravure inks, offset inks and silk screening inks; and resinous colorants or pigment printing agents for plastics and fibers.

The above-described polymeric microspheres, like the diguanamines described above can provide a method for a resin retardant to flame. Conditions which are adopted upon employment of the polymeric microspheres for the above application, for example, conditions for their combined use with other additives, their proportions in resin compositions, applicable resins and the like are similar to those set out above for the diguanamines. Some of such conditions will next be described by way of example.

In the flame-retarding method for a resin which features incorporation of the above polymeric microspheres, it is preferred to incorporate at least one phosphorus selected from phosphoruses consisting of simple substances of phosphorus and phosphorus-containing compounds. Preferred examples of such phosphoruses include red phosphorus, phosphoric acid, polyphosphoric acid, phosphorous acid, phosphonic acid, phosphate salts, polyphosphate salts, phosphite salts, phosphonate salts, phosphate esters, phosphite esters, phosphonate esters, phosphines and sulfur-containing phosphorus compounds. Such polyphosphate salts are preferably ammonium polyphosphates represented by formula $(NH_4)_{n+2}P_nO_{3n+1}$ in which n represents an integer greater than 5. The phosphoruses can be used in an amount of 5–40 wt. %, preferably 10–30 wt. % based on the resin.

It is also preferred to incorporate at least one compound selected from the isocyanuric acids and cyanuric acids represented by formulas (9) and (10), respectively. The proportion the isocyanuric acid or the cyanuric acid to be used can be chosen freely as needed but can generally range from 0.02 mole to 10 moles per equivalent of the diguanamine skeleton in the polymeric microspheres.

In the above-described flame-retarding method, it is possible and preferred to improve the flame retardancy of the resin further by using an amino-containing compound in combination with the diguanamine. The amount of such an amino-containing compound can be chosen freely as needed but can generally range from 0.01 wt. % to 10 wt. % based on the resin.

Further, it is particularly preferred to incorporate the above-described phosphoruses and amino-containing compound together in a resin.

Preferred examples of the resin are thermoplastic resins and thermosetting resins. The thermoplastic resins are preferably polyolefin resins, polyamide resins, styrene resins, polyphenylene ether resins, saturated polyester resins, polycarbonate resins, polyacetal resins and acrylic resins. The thermosetting resins are preferably unsaturated polyester resins, diallyl phthalate resins, epoxy resins and urethane resins.

A method for making a resin retardant to flame—which comprises incorporating 3–50 wt. % based on the resin, of a product obtained by reacting at least one compound selected from the diguanamines represented by formula (1) or (2) and the diguanamine derivatives represented by formula (11) or (12) with at least one compound selected from the above-described aldehydes, a product obtained by etherifying the former product with an alcohol, or a condensate or polymer thereof—can significantly improve the flame retardancy of the resin like the flame-retarding methods described above and is therefore an extremely useful method.

In the above-described method, the conditions adopted for the above-described flame-retarding methods making use of the diguanamine, for example, the conditions for the combined use of the phosphoruses, the isocyanuric acids, the cyanuric acids and/or the amino-containing compounds, their proportions in resin compositions, applicable resins and the like can be applied likewise.

The use of the diguanamines, the diguanamine derivatives and their preparation process and use, and the polymeric microspheres and their use, all of which have been described above and pertain to the present invention, can bring about the following effects as advantages of the present invention.

According to the flame-retarding method of the present invention for a resin, the flame retardancy of the resin can be significantly improved owing to the incorporation of the novel diguanamine having the specific structure in the resin. The diguanamine has better heat resistance and its sublimation, bleeding or the like is not observed compared with melamines. The flame-retarding method has excellent effects for the improvement of the flame retardancy of the resin, because the resin so treated is extremely good in char formability or the like, develops extremely little sagging or dripping of oil droplets or a melt and does not give off extremely noxious gas during burning. Further, the combined use of the diguanamine with the phosphoruses, the isocyanuric acids, the cyanuric acids and/or the amino-containing compounds can provide the flame-retarding method for a resin, which can obtain still improved flame retardancy because of synergistic effects. These methods have made it possible to expand the application field of resins still further. The present invention is therefore extremely important from the industrial standpoint.

The thermal stabilization method of the present invention for a resin, on the other hand, features the incorporation of the novel diguanamine of the specific structure in the resin, so that the resin is significantly improved in ultraviolet light resistance, thermal stability and the like. Even when the resin so treated is molded or otherwise formed at high temperatures, coloration or discoloration of the resin is minimized, thereby demonstrating improved thermal stability. Further, even when used for a long time at relatively high temperatures, deterioration is reduced so that the retention of physical properties has been improved substantially. The thermal stabilization method is extremely effective for the stability to heat, light and the like and can exhibit its effects for a long time, without developing any secondary disadvantages. In addition, the thermal stabilization method can substantially overcome the drawback that degradation or deterioration of the resin is promoted by heavy metal ions such as copper ions. The above thermal stabilization is therefore very effective for the improvement of the thermal stability of the resin. This method has made it possible to expand the application field of the resin still further. The present invention is therefore extremely important from the industrial standpoint.

According to the compatibilization method of the present invention, the novel diguanamine having the specific structure is incorporated in a blend of two or more resins of different kinds. This method is extremely effective for the improvement of the compatibility of the two or more resins of different kinds, because the compatibility of the resins can be significantly improved and, moreover, the blend so treated does not undergo much coloration or discoloration upon its processing or forming at high temperatures, the diguanamine is excellent in high-temperature stability and non-volatility, undergoes minimized sublimation, bleeding or the like, features easy handling and preparation and has good dispersibility in melts of polyamide resins, polyphenylene ether resins and the like, and the resin so treated is also improved in thermal stability. This method has made it possible to expand the application field of the resin still further. The present invention is therefore extremely important from the industrial standpoint.

Each diguanamine derivative according to the present invention features that it can impart excellent heat resistance, flame retardancy, weatherability, flexibility and toughness to resins, contains active hydroxyl and imino groups capable of exhibiting excellent reactivity with compounds having one or more of various functional groups such as isocyanate, carboxyl, epoxy and aldehyde group and the like, and permits selection of the number of functional group(s) from a wide range, for example, eight functional groups containing an active hydrogen atoms. Further, the diguanamine derivative is also excellent in properties such as curing property and high-hardness-imparting property so that it can provide compounds, resins, compositions and the like having excellent properties. The diguanamine derivative is therefore useful for an extremely wide variety of applications. In addition, the process of the present invention for the preparation of the diguanamine derivative comprises reacting the novel diguanamine having the specific structure with the diamine or the above diguanamine and/or diguanamine derivative with the epoxide under the particular conditions so that the target derivative can be obtained easily in a high yield. The preparation process is therefore excellent.

The diguanamine derivatives according to the present invention have excellent effects such that, when incorporated in a resin to make the resin retardant to flame, they can substantially improve the flame retardancy of the resin, and the resin so treated is extremely good in char formability or the like, develops no substantial sagging or dripping of oil droplets or a melt and good in self-extinguishment. The combined use of the phosphoruses, the isocyanuric acids, the cyanuric acids and/or the amino-containing compounds in the above-described method can provide a flame-retarding method which can impart still improved flame retardancy owing to synergistic effects. The present invention is therefore extremely important from the industrial standpoint.

Each diguanamine derivative described above has excellent effects such that, when incorporated in a resin to thermally stabilize the resin, the derivative can significantly improve the thermal stability and ultraviolet light resistance of the resin, can minimize coloration or discoloration of the resin upon processing or forming it at high temperatures, has superb high-temperature stability, does not undergo substantial sublimation, bleeding or the like, can be handle easily, and has good dispersibility in a melt of the resin. Further, when the diguanamine derivative is incorporated in a blend of two or more resins of different kinds to compatibilize the resins, the diguanamine derivative shows excellent effects such that it can substantially improve the compatibility of the different resins and, moreover, it can minimize coloration or discoloration of the resins upon processing or forming it at high temperatures, does not undergo substantial sublimation, bleeding or the like, can be handled easily, and has good dispersibility in a melt of the resin. These resin modification methods making use of the above-described diguanamine derivative according to the present invention have made it possible to expand the application field of the resin still further. The present invention is therefore extremely important from the industrial standpoint.

The above-described diguanamine derivatives can each be incorporated together with an organoisocyanate component to provide a polyurethane resin composition. Such a resin composition can provide a material excellent in properties, for example, mechanical properties such as flame retardancy, heat resistance, water resistance, abrasion resistance, flexibility, toughness and elasticity. The present invention is therefore extremely important from the industrial standpoint.

The polymeric microspheres according to the present invention can be obtained by emulsifying an amino resin with a protective colloid, adding a curing agent to the emulsion so formed, and then polymerizing the resultant mixture. The amino resin has been obtained by reacting an amino compound, which contains the novel diguanamine having the particular structure, with the aldehyde. The polymeric microspheres are excellent in heat resistance, solvent resistance, weatherability, impact resistance and abrasion resistance. When colored with a colorant, polymeric microspheres useful as a resinous colorant can be provided. Such polymeric microspheres are extremely useful for a wide variety of applications, for example, as resin modifiers (such as fillers, heat resistance improvers, flame retardancy improvers, thermal stability improvers, abrasion resistance improvers, and elasticity regulating agents) for thermoplastic resins, thermosetting resins and rubbers; anti-blocking agents for plastic films, cellophane films and inks; viscosity regulating agents for paints, inks, adhesives and cosmetics; and surface modifiers. The present invention is therefore extremely important from the industrial standpoint.

The polymeric microspheres according to the present invention have excellent effects such that, when incorporated in a resin to make the resin retardant to flame, they can substantially improve the flame retardancy of the resin, they do not undergo sublimation, bleeding or the like as opposed to melamines, and the resin so treated is good in heat resistance and extremely good in char formability or the like, develops no substantial sagging or dripping of oil droplets or a melt, and does not give off extremely noxious gas or the like upon burning. The combined use of the phosphoruses, the isocyanuric acids, the cyanuric acids and/or the amino-containing compounds in the above-described method can provide a flame-retarding method which can impart still improved flame retardancy owing to synergistic effects. This flame-retarding method has made it possible to expand the application field of the resin still further. The present invention is therefore extremely important from the industrial standpoint.

THIRD INVENTION GROUP

TECHNICAL FIELD

This invention relates to a thermosetting molding composition extremely useful, for example, as general molding materials for household appliances, automotive parts or components, various machines and electrical parts or components, laminate-molding materials, and molding materials for sheet and bulk molding processes for the formation of fiber-reinforced plastics. This invention is also concerned with a thermosetting expansion-forming composition useful as an expansion-forming material for dividing walls (partitions) in buildings, a heat-insulating, sound-proofing or low-temperature shielding material for housing and transportation equipments, a warm material for tanks, an impact-resistant packaging material, or a filler. The term "forming" as used herein should be interpreted in a broad sense so that it embraces not only molding but also other forming techniques such as extrusion.

BACKGROUND ART

Thermosetting Molding Material

In general, the term "thermosetting molding material" means a material which has been obtained by impregnating a thermosetting resin with a curing agent, a filler, a mold release agent, a dye or pigment, a thickening agent and the like as needed so that it can be conveniently formed into a desired shape by heating and pressing it as needed. Such materials are advantageous inter alia in that they can be directly formed into products of various shapes, the products so formed have a good surface finish, formed products of a desired color can be obtained by dispersing the corresponding dye or pigment in advance and no coating work is needed, so that they are useful as industrial materials. Known examples of the thermosetting resin include phenol resins, melamine resins, and unsaturated polyester resins.

Among these molding materials, phenol resins are excellent in electrical insulating property and cracking resistance but, as their defects, are poor in weatherability and high-temperature discoloration resistance as well as arc resistance and anti-tracking properties, so that their applications are considerably limited. Melamine resins are excellent in colorability, surface hardness, anti-tracking properties and the like but exhibit insufficient flowability upon molding. Molded products obtained from melamine resins lack flexibility and have poor impact resistance and, as their defects, tend to develop seasoning cracks and metal insert cracks. Unsaturated polyester resins, on the other hand, are excellent in flexibility, water resistance and the like but, as their defects, lack heat resistance and at relatively high temperatures, chemical resistance and are susceptible to burning. Accordingly, these thermosetting molding materials are still dissatisfactory for practical use and substantial limitations are imposed thereon technically and economically.

With a view to overcoming the above-described drawbacks of molding materials making use of such thermosetting resins, the present inventors have conducted an extensive investigation. As a result, it has been found that use of an amino resin—which is obtained by reacting an aldehyde with an amino compound containing a novel specific diguanamine totally different in structure and properties from conventionally known compounds—features easy and simple production and handling of the resin and can conveniently provide a thermosetting molding composition which is easy to handle and has excellent flowability upon forming, and easy formation of products of various shapes having excellent weatherability, heat resistance, electrical characteristics, mechanical properties and the like, leading to the present invention.

Thermosetting Expansion-forming Composition

Further, this invention also relates to a thermosetting expansion-forming composition.

It is conventionally known that a foam can be obtained from a resin composition, which contains a primary condensate obtained by reacting melamine, urea or the like with formaldehyde, by causing the resin composition to expand and cure.

In such a resin composition, use of a primary condensate of melamine or the like involves the drawbacks that the resulting foam is hard and brittle and tends to break upon processing or forming. It has been proposed to improve its elasticity and shatter resistance by introducing a polyol or the like. This proposal is however accompanied by drawbacks such that the resulting foam is still insufficient in elasticity, shape restorability and the like and is significantly reduced in flame retardancy, heat resistance and the like. It has also been proposed to obtain a foam of relatively good mechanical properties, heat insulating property and the like by exposing a resin composition, which contains a primary condensate of melamine or the like having a relatively large condensation degree, to a high frequency wave and causing it to expand and cure. A primary condensate of melamine or the like having a small condensation degree, however, involves drawbacks such that it leads to a foam significantly reduced in mechanical properties, heat insulating property end the like and can hardly provide any good foam and moreover a liquid formulation of the primary condensate tends to form a precipitate and has poor workability and storage stability, although the solubility and dispersibility in a solvent are improved to some extents. A large condensation degree, on the other hand, can provide a foam having relatively good mechanical properties and heat insulating property, but such a large condensation degree is accompanied by drawbacks such that the resulting foam has very poor solubility or dispersibility in a solvent such as water. Achievement of an increased condensation degree upon production of a resin results in drawbacks such that the solubility and compatibility are substantially lowered and the resin may separate during the reaction, whereby it is extremely difficult to obtain any preferred primary condensate. With a view to improving these drawbacks and difficulty, it has also been proposed to evaporate a liquid mixture of a resin having a relatively small condensation degree to dryness, to allow the resin to age to have a larger condensation degree and then to redissolve and disperse the resin. These processes however require complex production steps, need substantial consumption of heat and are disadvantageous economically. Moreover, the above methods are accompanied by drawbacks such that substantial difficulties are encountered for the control of the condensation, they require additional steps for re-dissolution, dispersion or the like of the resin and are cumbersome, the distribution of condensation degree is wide, thereby making it difficult to achieve full dissolution, dispersion or the like the resin, significant limitations are imposed on the conditions for the production of foams, storage stability and workability are insufficient, the resulting foam can hardly be controlled in performance and quality, and the performance is not still sufficient and the application is considerably limited.

It has also been proposed to obtain a foam with improved elasticity and flexibility from a resin composition containing a primary condensate or urea or the like. Although this method can provide a foam having somewhat improved mechanical properties, it is accompanied by drawbacks such that the resulting foam is considerably inferior in flame retardancy, heat resistance and the like and its application is therefore very limited.

These resin compositions have the above-described drawbacks and are still insufficient for practical use. Substantial limitations have hence been imposed technically and economically on them.

With a view to overcoming the above-described drawbacks of such resin compositions and foams obtained therefrom, the present inventors have conducted an extensive investigation. As a result, it has been found that use of an amino resin—which is obtained by reacting an aldehyde with an amino compound containing a novel specific diguanamine different in structure and properties from conventionally known compounds—or a modified amino resin obtained by modifying the above amino resin with a sulfonic acid can provide an expansion-forming composition featuring extremely good solubility or dispersibility in a solvent such as water, storage stability and the like, easy and simple production and handling of the resin and composition, and the ability to provide a foam excellent in flame retardancy and mechanical properties. It has also been found that an elastic foam excellent in heat insulating property, sound-proofing property, flame retardancy, heat resistance, impact resistance, vibration resistance, processability, formability, mechanical properties and the like and useful for a wide variety of application can be provided. These findings have led to the present invention.

DISCLOSURE OF THE INVENTION

An object of the present invention is to improve the drawbacks of the conventional thermosetting molding compositions and thermosetting expansion-forming compositions as described above. This invention therefore provides:

(a) a thermosetting molding composition comprising an amino resin and a reinforcing material, said amino resin having been obtained by reacting at least one aldehyde with an amino compound comprising at least one diguanamine selected from diguanamines represented by the following formula (1):

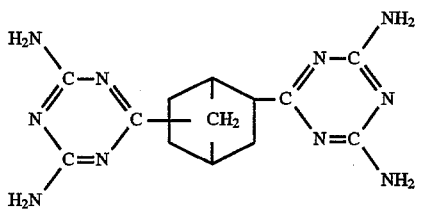

wherein the bonding sites of the 4,6-diamino-1,3,5-triazin-2-yl groups are the 2,5- or 2,6-positions, or by the following formula (2):

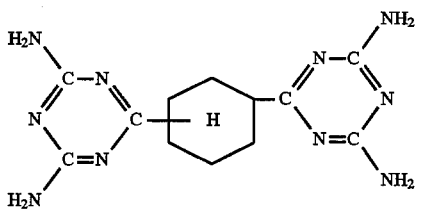

wherein the bonding sites of the 4,6-diamino-1,3,5-triazin-2-yl groups are the 1,2-, 1,3- or 1,4-positions; and (b) a thermosetting molding composition comprising an amino resin and a reinforcing material, said amino resin having been obtained by reacting at least one aldehyde with an amino compound comprising at least one diguanamine derivative selected from diguanamine derivatives represented by the following formula (11):

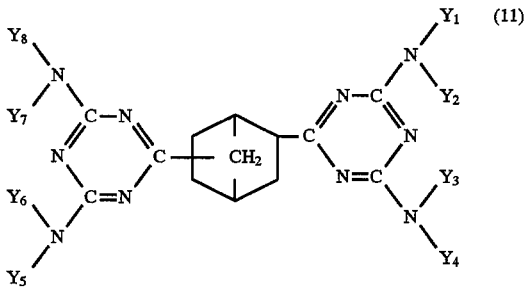

wherein the bonding sites of the 1,3,5-triazin-2-yl groups are the 2,5- or 2,6-positions, and $Y_1$, $Y_2$, $Y_3$, $Y_4$, $Y_5$, $Y_6$, $Y_7$ and $Y_8$ are the same or different and individually represent a substituent selected from the group consisting of a hydrogen atom and groups containing at least two carbon atoms, with the proviso that at least one of $Y_1$, $Y_2$, $Y_3$, $Y_4$, $Y_5$, $Y_6$, $Y_7$ and $Y_8$ is a group containing at least two carbon atoms, or by the following formula (12):

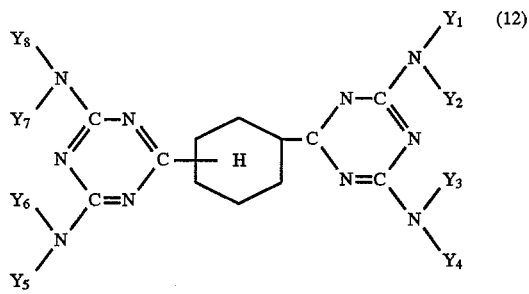

wherein the bonding sites of the 1,3,5-triazin-2-yl groups are the 1,2-, 1,3- or 1,4-positions and $Y_1$, $Y_2$, $Y_3$, $Y_4$, $Y_5$, $Y_6$, $Y_7$ and $Y_8$ have the same meanings as defined in formula (11).

The present invention also provides:

(c) a thermosetting expansion-forming composition comprising an amino resin, an emulsifier, a foaming agent and a curing agent, said amino resin having been obtained by reacting at least one aldehyde with an amino compound comprising at least one diguanamine selected from the diguanamines represented by formula (1) or (2);

(d) a thermosetting expansion-forming composition comprising an amino resin, an emulsifier, a foaming agent and a curing agent, said amino resin having been obtained by reacting at least one aldehyde with an amino compound comprising at least one diguanamine derivative selected from the diguanamines derivatives represented by formula (11) or (12); and (e) a thermosetting expansion-forming composition comprising a modified amino resin, an emulsifier, a foaming agent and a curing agent, said modified amino resin having been obtained by sulfonating the amino resin set out above under (c) or (d).

BEST MODE FOR CARRYING OUT THE INVENTION

Among the above-described diguanamine derivatives according to the present invention, preferred are hydroxyl-containing diguanamine derivatives represented by formula (11) or (12) in which $Y_1$, $Y_2$, $Y_3$, $Y_4$, $Y_5$, $Y_6$, $Y_7$ and $Y_8$ individually represent a substituent selected from the group consisting of a hydrogen atom and groups represented by HO—$Y_9$—, $Y_9$ being a divalent group containing at least two carbon atoms. Also preferred are hydroxyl diguanamine derivatives in which HO—$Y_9$— is a group selected from the group consisting of 2-hydroxyethyl, 2-hydroxypropyl, 1-hydroxymethylpropyl, 3-hydroxypropyl, 5-hydroxy-3-oxapentyl and 4-hydroxyphenyl groups. Also preferred are oxaalkyl-containing diguanamine derivatives represented by formula (11) or (12) in which at least one of $Y_1$, $Y_2$, $Y_3$, $Y_4$, $Y_5$, $Y_6$, $Y_7$ and $Y_8$ represents a group selected from the group consisting of groups represented by formula (13) or (14). More preferably, $Y_{10}$ in formula (13) or (14) is at last one group selected from ethylene and propylene.

More preferred are diguanamine derivatives represented by formula (11) or (12) in which $Y_2$, $Y_4$, $Y_6$ and $Y_8$ are individually a hydrogen atom and $Y_1$, $Y_3$, $Y_5$ and $Y_7$ are individually a substituent selected from the group consisting of a hydrogen atom, the above-described groups HO—$Y_9$—, and groups represented by formulas (13) and (14) respectively.

The proportion of the diguanamine or the diguanamine derivative in the thermosetting molding composition according to the present invention can be chosen freely depending on the desired properties. To provide a thermosetting molding composition which can be produced easily and simply, has excellent flowability upon molding, permits easy formation of products of various shapes and are excellent in weatherability, heat resistance, flame retardancy, electrical characteristics, mechanical properties and the like, it is preferred to control the proportion of the diguanamine or the diguanamine derivative in an amount of at least 40 wt. %, more desirably at least 80 wt. % based on the amino compound.

To obtain a liquid amino resin formulation, which has better storage stability and can provide formed products superior in adhesion properties, mechanical properties and the like, by using the diguanamine derivative, the diguanamine derivative should amount preferably to 0.1–70 wt. %, more preferably 1–30 wt. % of the amino compound.

The amino compound can additionally include one or more compounds other than the above-described diguanamines or diguanamine derivatives. Illustrative of such compounds include melamine, N-methylmelamine, benzoguanamine, acetoguanamine, cyclohexanecarboguanamine, cyclohexenecarboguanamine, norbonanecarboguanamine, norbornenecarboguanamine, dicyandiamide, urea, thiourea, guanidine, urethane, phenol, p-methylphenol, nonylphenol, resoles, aniline, tetramethylenediamine, furfural, furfuryl alcohol, p-toluenesulfonamide, o-toluenesulfonamide, benzenesulfonamide, tetralinsulfonamide, carboxylic amides, sulfuryl amide, and lower polymer of phosphorus diamide nitride. Such additional compounds can be used in any total amount insofar as the significance of the use of such an amino compound as described above in the present invention is not impaired, but preferably in a total amount smaller than 60 wt. % of the amino compound.

Usable examples of the aldehydes usable in the present invention include formaldehydes such as formaldehyde, paraformaldehyde, hexamethylenetetramine, methylhemiformal, butylhemiformal and formaldehydesodium bisulfite adduct; glyoxal; acetaldehyde; trimethylol acetaldehyde; acrolein; benzaldehyde; furfural; phthalaldehyde; and terephthaldehyde. Among these, an aqueous solution of formaldehyde and paraformaldehyde are preferred. Such aldehydes can be used generally in an amount of 1.0–16 moles, preferably 1.5–8.0 moles, more preferably 2.0–7.5 moles per mole of the amino compound.

Although no particular limitation is imposed on the manner of obtaining the amino resin for use in the present invention, several processes may be mentioned as examples. A liquid mixture, which has been formed by stirring and mixing the above-described amino compound and aldehyde in a solvent system such as one or more of water, alcohols, ethers and/or aromatic compounds, is subjected to an addition reaction at 30°–80° C. and pH 8–13, whereby an N-methyloldiguanamine is obtained. As an alternative, such a liquid mixture is subjected to addition condensation under high alkaline conditions of pH 13 or higher or under conditions of pH 8 or lower, whereby a primary condensate of an N-methyloldiguanamine is obtained. As a further alternative, the N-methyloldiguanamine or the primary condensate of the N-methyloldiguanamine so obtained is caused to undergo further condensation at pH 1–6 and 50°–100° C. so that a condensate is obtained with an increased condensation degree. As a still further alternative, the amino resin obtained by conducting a reaction as described above is heated at 60°–150° C. under normal or reduced pressure to eliminate water originated from the aldehyde as the raw material, water formed by the condensation reaction, the solvent and the like. The amino resin so obtained is also useful. It is however to be noted that the manner of production of the amino resin is not limited to such processes and conventionally-known processes can also be used likewise. In some instances, conditions such as the condensation degree of the amino resin, the solvent and the pH can be chosen as needed.

The thermosetting molding composition according to the present invention features the inclusion of the above-described amino resin and a reinforcing material as essential components. The combined use of such an amino resin and a reinforcing material can provide a thermosetting molding composition having excellent properties extremely difficult to obtain with conventional melamine-type amino resins, such as excellent flowability upon molding, weatherability and adhesion properties with the reinforcing material and, owing to synergistic effects, still improved heat resistance, flame retardancy, mechanical properties and the like.

Illustrative examples of the reinforcing material include, but are not limited to, glass fibers such as E-glass fibers, C-glass fibers, A-glass fibers, S-glass fibers, and glass fibers obtained by finishing such glass fibers with a coupling agent; glass fiber products such as glass rovings, glass cloths, chopped glass strands, and chopped glass strand mats, all obtained from such glass fibers as described above; polycrystalline fibers such as a variety of carbon fibers, alumina fibers, zirconia fibers and boron nitride fibers; composite fibers such as boron fibers, silicon carbide fibers, polytitanocarbosilane fibers and calcium titanate fibers; organic fibers such as aramid fibers, polypropylene fibers, polyethylene fibers, polyester fibers, vinylon fibers, polyimide fibers and polyimideamide fibers; metal fibers such as tungsten fibers, molybdenum fibers, steel fibers and gallium fibers; and various products formed of such fibers or fiber products. Among these, glass fibers are preferred.

The thermosetting molding composition according to the present invention can contain, as needed, one or more of known auxiliary raw materials for molding materials, such as curing agents, fillers, mold release agents, colorants, stabilizers and preform bonding materials. In addition, a viscosity regulating agent such as a solvent can also be incorporated as needed.

The thermosetting molding composition according to the present invention can provide a molded product in the presence or absence of a curing agent. A suitable curing agent can be chosen as needed.

Examples of the curing agent include, but are not limited to, mineral acids such as hydrochloric acid, sulfuric acid, phosphoric acid and nitric acid; carboxylic acids such as formic acid, benzoic acid, phthalic acid, acetic acid, α-chloroacetic acid, trifluoroacetic acid, propionic acid, salicylic acid, oxalic acid, lactic acid and amino acids; sulfonic acids such as benzenesulfonic acid, p-toluenesulfonic acid and dodecylbenzenesulfonic acid; ammonium salts such as ammonium chloride, ammonium sulfate, ammonium phosphate, ammonium dihydrogenphosphate, diammonium hydrogenphosphate, ammonium nitrate, ammonium formate, ammonium acetate, ammonium p-toluenesulfonate, ammonium sulfamate and diammonium imidosulfonate; chloroacetamides; and water-soluble metal salts of metals such as zinc, magnesium, calcium and aluminum with acids such as nitric acid, sulfuric acid and phosphoric acid, with ammonium salts such as ammonium nitrate and water-soluble metal salts such as zinc nitrate being preferred.

Usable exemplary fillers include, but are not limited to, calcium carbonate, calcium sulfate, barium sulfate, hydrated alumina, calcium oxide, magnesium oxide, calcium hydroxide, magnesium hydroxide, ultrafine silica powder, mica, asbestos, clay, talc, silica sand, glass balloons, shirasu (white volcanic ash) balloons, sand, gravel, porcelain powder, glass powder, polycarbonate powder, polyethylene powder, pulp dust, paper, waste threads and fabric pieces.

Illustrative examples of the mold release agent include, but are not limited to, wax, POVAL (polyvinyl alcohol), silicone, zinc stearate, magnesium stearate, calcium stearate, aluminum distearate, stearic acid, soybean lecithin, carboxylic esters such as dimethyl oxalate, maleic anhydride, phthalic anhydride, and organophosphoric esters. These mold release agents can be chosen freely as needed depending on the molding method, the material and shape of the mold, the post-coating, etc.

In the thermosetting molding composition according to the present invention, a dye and/or a pigment can be used as a colorant to give a desired color to molded products or coatings.

Illustrative examples of the colorant include but are not limited to, cadmium red, red iron oxide, Lake Red G, Carmine 6B, condensed azo red, quinacridone red, perylenes, anthraquinone, cadmium orange, chrome vermilion, pyrazolones, perinones, cadmium yellow, chrome yellow, yellow iron oxide, titanium yellow, disazo yellow, isoindolinones, chromium oxide, copper phthalocyanine green, ultramarine, cobalt blue, copper phthalocyanine blue, quinacridone violet, dioxadiviolet, titanium white, black iron oxide, carbon black, Oil Orange S, Rhodamine B, and Rhodamine 6GCP.

Upon production, processing or forming of the thermosetting molding composition according to the present invention, known methods which are employed for molding compositions are all useful and can be chosen for use as needed. For example, materials which are generally used in molding materials are added at a desired stage until the amino resin reaches the B-stage. The resulting mass is thoroughly kneaded at room temperature or under heat by using a kneader, a heating roll, an extruder or the like. A curing agent, a mold release agent, a colorant and/or the like are then added as needed, followed by grinding in a ball mill or the like. As another example, a glass cloth or the like is impregnated with a liquid formulation of the amino resin, followed by desolvation or the like. The glass cloth of the like so treated is then subjected to aging under heat. As a further example, a mixture—which has been formed by uniformly dispersing a curing agent, a filler a mold release agent, a colorant and/or the like in a liquid formulation of the amino resin—is coated on a film of polyethylene or the like. The thus-coated film is then compression-bonded to a desired reinforcing material such as glass fibers to impregnate the reinforcing material with the mixture, whereby a sheet-like prepreg is obtained. This prepreg is subjected to defoaming, desolvation and the like, followed by aging. As a still further example, a liquid formulation of the amino resin is added with a curing agent, a filler, a mold release agent, a colorant and/or the like, followed by desolvation. The resulting mixture is kneaded in a kneader, to which glass fibers are added and then dispersed evenly. The mass so molded is then taken out of the kneader, divided into desired sizes and then subjected to aging. It is however borne in mind that the production, processing and/or molding of the thermosetting molding composition is not limited to the methods exemplified above.

In the thermosetting molding composition according to the present invention, the reinforcing material is preferably glass fibers.

It is more preferred to incorporate at least one of the curing agents.

The above-described thermosetting molding composition according to the present invention can preferably be used as a laminate-molding composition, a sheet molding composition or a bulk molding composition.

As has been described above, the thermosetting molding composition according to the present invention can be added with various components as needed. These components can be changed in various ways depending on the workability, the molding conditions, the application of the molded product and the like. Preferred compositions may comprise, for example, 5–95 parts by weight of an amino resin useful in the present invention, 0.5–10 parts by weight of a curing agent, 0–90 parts by weight of a filler, 5–90 parts by weight of a reinforcing material and 0–50 parts by weight of a mold release agent, although the thermosetting molding composition according to the present invention is not limited to them.

The thermosetting molding composition according to this invention, which has been obtained as described above, has excellent flowability upon molding, so that it can be employed for the formation of products having complex shapes or large dimensions. Molded products, which have been obtained using the thermosetting molding composition, are excellent in weatherability, heat resistance, flame retardancy, electrical characteristics, mechanical properties and the like and are useful in a wide variety of fields, for example, household appliances such as bath tabs, purifying tanks, sink cabinets, table ware and chairs; automobile parts and components such as fenders, front and rear skirts, engine hoods, wheel caps and instrument panels; corrosion-resistant equipments such as filter presses, pump housings, tanks, vessels and cleaning towers; mechanical parts and components; and electrical parts and components such as switch boxes, meters, covers, electrically insulating parts, laminated substrates and electronic circuit boards.

This invention also provides an excellent thermosetting expansion-forming composition which makes use of an amino resin obtained from one or more of the above-described diguanamines and diguanamine derivatives.

The proportion of the diguanamine or the diguanamine derivative in the thermosetting expansion-forming composition according to the present invention can be chosen freely depending on the desired properties. To provide a thermosetting expansion-forming composition which has excellent solubility or dispersibility in a solvent such as water and superb storage stability and can provide foams excellent in heat insulating property, soundproofing property, flame retardancy, mechanical properties and the like, it is preferred to control the proportion of the diguanamine or the diguanamine derivative in an amount of at least 40 wt. % more desirably at last 80 wt. % based on the amino compound.

To obtain a liquid amino resin formulation, which has better stability in an aqueous solution and can provide foams superior in mechanical properties such as elongation at break, by using the diguanamine derivative, the diguanamine derivative should amount preferably to 0.1–80 wt. %, more preferably 1–60 wt. % based on the amino compound.

The amino compound useful in the present invention can include one or more compounds other than the above-described diguanamines and diguanamine derivatives, for example, one or more of the amino compounds exemplified above in connection with the thermosetting molding composition to an extent not impairing the significance of the use of the amino compound in the present invention, so that these compounds should amount preferably to less than 60% based on the amino compound.

As the aldehyde in the thermosetting expansion-forming composition according to the present invention, aldehydes usable, for example, in the above-described thermosetting molding composition are also useful. Among these, formaldehydes and glyoxal are preferred, with an aqueous solution of formaldehyde and paraformaldehyde being more preferred. Such formaldehyde(s) preferably account for at least 50 wt. % of the aldehyde. The aldehyde can be used generally in an amount of 1.0–16 moles, preferably 1.5–8.0 moles, more preferably 2.5–6.0 moles per mole of the amino compound.

Although no particular limitation is imposed on the manner of obtaining the amino resin for use in the production of the thermosetting expansion-forming composition according to the present invention, several processes may be mentioned as examples. A liquid mixture, which has been formed by stirring and mixing the above-described amino compound and aldehyde in one or more solvents such as water, alcohols and/or aromatic compounds, is subjected to an addition reaction at 30°–80° C. and pH 8–13, whereby an N-methyloldiguanamine is obtained. As an alternative, such a liquid mixture is subjected to addition condensation under high alkaline conditions of pH 13 or higher or under conditions of pH 8 or lower, whereby a primary condensate of the N-methyloldiguanamine is obtained. As a further alternative, the N-methyloldiguanamine or the primary condensate of the N-methyloldiguanamine so obtained is caused to undergo further condensation at pH 1–6 and 30°–80° C. so that a condensate is obtained with an increased condensation degree.

When an amino resin useful in the present invention is produced using the diguanamine or diguanamine derivative in a manner described above, the amino resin shows good water solubility even when its methylolation is allowed to proceed to a high degree. The amino resin so obtained is excellent in solubility, dispersibility, storage stability and the like and, moreover, has the excellent characteristic that no precipitation is observed even when the reaction is carried out at a high concentration. The resulting amino resin also has the excellent feature that it contains neither much low-molecular substances as sources for the formation of a precipitate, said low-molecular substances being responsible for reduced mechanical properties of a foam to be obtained, nor much high-molecular substances and branched substances as causes for poor solubility and/or dispersibility. The amino resin so obtained is superior to that available when the hydroxyl-containing diguanamine derivative is used. Use of such an amino resin can provide a thermosetting expansion-forming composition which is excellent in solubility, dispersibility, storage stability, production readiness and the like and can afford foams having excellent mechanical properties and the like.

A modified amino resin can be obtained by sulfonating a product which has been obtained by reacting an amino compound, which contains the above-described diguanamine or diguanamine derivative, with an aldehyde. This modified amino resin is also extremely useful as a component in thermosetting expansion-forming composition according to the present invention.

The modified amino resin can be obtained by adjusting the pH of an aqueous solution of the above-described N-methyloldiguanamine or primary condensate of N-methyloldiguanamine to 10–13, adding a sulfonating agent such as an alkali sulfite to the aqueous solution and then stirring the resultant mixture at 60°–80° C. until no sulfite salt is detected.

Also useful is a resin obtained by subjecting the modified product to condensation at pH 1.0–6.0 and 30°–80° C. to increase its condensation degree by an appropriate degree. The sulfonating agent can be used generally in an amount of 0.05–3.0 moles, preferably 0.1–2.0 moles per mole of the amino compound.

The modified amino resin has still better solubility or dispersibility in a solvent such as water, so that good solubility or dispersibility can be retained even if its condensation degree is increased substantially compared with the corresponding unmodified amino resin. Use of such a modified amino resin makes it possible to provide an expansion-forming composition excellent in storage stability, emulsifiability and the like and also a foam excellent in mechanical properties and the like.

Also useful is that obtained by heating an amino resin or modified amino resin, which has been obtained by conducting a reaction as described above, to 60°–150° C. under normal pressure or reduced pressure so that water originated from an aldehyde as a raw material, water formed by a condensation reaction, a solvent or the like are eliminated. It is however to be noted that the manner of production of the amino resin is not limited to the processes described above and conventionally known processes can also be used likewise. In some instances, it is possible to choose conditions such as the condensation degree, methylolation degree and/or sulfonation degree of the amino resin or modified amino resin, the solvent, pH, etc. as needed.

Such an emulsifier can lower the interfacial tension between the amino resin or modified amino resin, the foaming agent and the solvent such as water, so that the system so formed can be uniformly emulsified or dispersed into a stable system. Upon production of a foam, the emulsifier acts on minute bubbles so that the bubbles can be rendered uniform and stable. Use of the emulsifier is therefore preferred for obtaining a desired foam.

Illustrative emulsifiers include, but are not limited to, anionic emulsifiers, for example, alkylbenzenesulfonates such as sodium dodecylbenzenesulfonate and sodium dodecyldiphenylether disulfonate, alkyl naphthalenesulfonates such as sodium dipropylnaphthalenesulfonate and sodium naphthalenesulfonateformaldehyde condensate, alkylsulfonates such as sodium octadecanesulfonate and potassium dodecanesulfonate, dialkylsulfosuccinates such as sodium diisobutylsulfosuccinate and sodium dioctylsulfosuccinate, α-sulfonated fatty acid salts such as sodium α-sulfopalmitate, N-methyltaurine salts such as sodium N-methyl-N-oleyltaurine, sulfated oils such as α-olefinsulfonates, petroleum sulfonates and turkey red oil, alkylsulfates such as sodium laurylsulfate, sulfate esters such as polyoxyethylene alkyl ether, polyoxyethylene alkylphenyl ether, phosphate esters and salts, and alkylphosphate salts; nonionic emulsifiers, for example, the ethylene oxide adducts of alcohols, carboxylic acids and phenols, such as polyoxyethylene stearyl ether, polyoxyethylene nonylphenyl ether and sorbitol tristearate, and block copolymers such as ethylene oxide-propylene oxide block copolymers; cationic emulsifiers such as laurylamine acetate, stearyl trimethyl ammonium chloride, stearyl benzyl dimethyl ammonium chloride and dodecylpyridium bromide; and amphoteric emulsifiers such as lauryl betaine and stearyl betaine, with anionic emulsifiers and non-ionic emulsifiers being preferred. The emulsifier can be used in an amount of 0.2–5.0 wt. %, preferably 0.5–4.0 wt. % based on the total amount of the above-described amino resin and/or modified amino resin.

As such a foaming agent, it is possible to incorporate water or an alcohol as a solvent or a dispersant in a thermosetting molding composition according to the present invention and to use it as a principal component of the foaming agent. It is however preferred to incorporate a volatile foaming agent having a boiling point in a range of from −20° C. to 100° C., preferably from 20° C. to 80° C. Illustrative examples of the volatile foaming agent include, but are not limited to, aliphatic, alicyclic and aromatic hydrocarbons, halogenated hydrocarbons, alcohols, ketones, ethers, esters, azo compounds, carbonates and isocyanates, with pentane, hexane, heptane, trichlorotrifluoroethane, trichlorofluoromethane and the like being preferred. The amount of the volatile foaming agent can be chosen freely as needed depending on the desired final density of the foam and the kind of the foaming agent. In generally, the volatile foaming agent is used in an amount of 1–50 wt. %, preferably 3–40 wt. % based on the total amount of the above-described amino resin and/or modified amino resin.

As the curing agent, any compound can be used as long as it can release or form protons under production conditions. Compounds having high water solubility are preferred. For example, the curing agents usable in the above-described thermosetting molding composition are also useful. Formaldehyde itself forms formic acid and acts as a curing agent, so that formaldehyde is also useful. It is however to be noted that the curing agent is not limited to such exemplified ones. The curing agent can be used in an amount of 0.01–20 wt. %, preferably 0.05–5 wt. % based on the total amount of the above-described amino resin and/or modified amino resin.

Further, the thermosetting expansion-forming composition according to the present invention can contain other additives, for example, a dye or pigment, a flame retardant and/or a filler, a reinforcing material such as glass fibers, carbon fibers or polyaramid fibers, a gas toxicity lowering agent, a hydrophobicity imparting agent, a mold release agent, a mildewproofing agent, a bacteriocide and/or one or more other polymers as needed insofar as the effects of the present invention are not impaired.

In the thermosetting expansion-forming composition according to the present invention, the concentration of the above-described amino resin and/or modified amino resin in a solvent such as water is chosen as desired depending on the temperature of a system in which foaming is conducted, the kind of the foaming agent, the viscosity of the liquid formulation at the time of initiation of foaming, etc. In general, the concentration is in a range of from 50 wt. % to 90 wt. %, preferably in a range of from 60 wt. % to 85 wt. %.

No particular limitation is imposed on the manner of production of an elastic foam according to the present invention. Processes which are employed upon foaming known expansion-forming liquid resin formulations can be applied. For example, the above-described thermosetting expansion-forming composition is supported on a heating band or the like and is heated by radiation such as hypersonic wave (0.2 GHz to 100 GHz), infrared rays or far infrared rays, hot air or the like to a temperature sufficient to cause evaporation or boiling of the foaming agent or production of blowing gas such as carbon dioxide under a preset pressure while choosing the quantities of radiation, heat and the like, whereby its foaming and curing are conducted. It is however borne in mind that the production process is not limited to the above-exemplified one.

It is also useful to subject the thus-obtained elastic foam to post-treatment, for example, to heat the elastic foam at 100°–250° C. for 1–200 minutes to sufficiently eliminate a solvent such as water, a foaming agent, formaldehyde and the like and then to cure the thus-heated elastic foam or to compress the elastic foam by 40–90% and then to allow it to expand. Such post-treatment has excellent effects such that the resulting elastic foam has a smaller shrinkage factor, a lower equilibrium moisture content and an improved modulus of elasticity and the release of formaldehyde from the resulting elastic foam is substantially reduced.

The elastic foam so obtained can be used as is or after cutting it into a desired plate, sheet or the like. As a further alternative, a cover layer can be applied or bonded to one or each side of the elastic foam by using a paper sheet, a cardboard, a board, a gypsum board, a metal plate, a metal foil, a plastic sheet or the like.

The thermosetting expansion-forming composition according to the present invention is excellent in heat insulating property, sound absorbing qualities, heat resistance, flame retardancy, impact resistance, vibration resistance and the like and can provide foams useful for a wide variety of applications, for example, as heat-insulating soundproof materials such as dividing walls (partitions), wall materials, ceiling materials, door materials, floor materials, curtain wall core materials and panel core materials for buildings; low-temperature heat insulating materials for roofs, eaves and the like of refrigerators, freezers, liquefied gas containers, containers and cold storages; low-temperature insulating materials for oil and like storage tanks, ducts, pipes and the like in factories; flame-retardant fillers for metal sidings, sealing materials and heat-resistant materials; heat-insulating soundproof materials, vibration-resistant materials and cushioning materials for transportation equipments such as automobiles, vehicles and aircraft; impact-absorbing packing materials; fillers; and the like.

In the above-described thermosetting expansion-forming composition, the emulsifier is preferably at least one emulsifier selected from anionic emulsifiers and nonionic emulsifiers while the foaming agent is preferably a volatile foaming agent having a boiling point in a range of 20°–80° C. under normal pressure.

Further, a particularly useful elastic foam is one having a bulk density of 1.5–80 g/l and obtained by foaming and curing a liquid formulation of the above-described thermosetting expansion-forming composition.

Owing to the use of the amino resin obtained by reacting the amino compound, which contains the novel diguanamine having the particular structure, with the aldehyde, the above-described thermosetting molding composition according to the present invention features simple and easy production and handling of the resin and composition, shows excellent formability and flowability upon molding, permits easy forming of product of complex shapes and can provide formed products excellent in high-temperature discoloration resistance, light resistance, electrical characteristics such as electrical insulating property and arc resistance, heat resistance, flame retardancy, mechanical properties and the like. The thermosetting molding composition is useful as a general molding material, a laminate-molding material, a sheet molding material, a bulk molding material or the like and its application can be expanded to a wide variety of fields such as household appliances, parts and components of transportation equipments such as automobiles, industrial parts and components, tanks, containers, apparatuses, and electrical parts and components such as electrical insulating materials and electronic circuit substrates. This invention is therefore extremely important from the industrial standpoint.

Owing to the use of the amino resin obtained by reacting the amino compound, which contains the novel diguanamine having the particular structure, with the aldehyde, and/or the modified amino resin obtained by sulfonating the amino resin, the thermosetting expansion-forming composition according to the present invention has extremely good solubility or dispersibility in a solvent such as water and also extremely good storage stability, features simple and easy production of the resin and the composition, provides excellent foams and are hence extremely useful. By foaming and curing the thermosetting expansion-forming composition, it is possible to provide an elastic foam excellent in heat insulating property, soundproofing qualities, flame retardancy, heat resistance, impact resistance, vibration resistance, processability, formability, mechanical properties and the like. The thermosetting expansion-forming composition is therefore extremely useful for a wide variety of applications, for example, as heat-insulating materials and sound-deadening and soundproof materials for dividing walls (partitions), roofs, doors and floors of buildings and the like, refrigerators, constant-temperature rooms and the like; heat-insulating materials, soundproof materials and heat insulating barriers for transportation equipments such as automobiles, vehicles and aircraft; heat insulating materials for tanks, containers and the like in industrial equipments; insulating materials; impact absorbing packaging materials; fillers; etc. The present invention is therefore extremely important from the industrial standpoint.

The present invention will next be described in detail by the following referential examples and examples. It should however be borne in mind that this invention is by no means limited to or by these referential examples and examples.

Incidentally, tests of the elastic foam in each Example were performed in accordance with the following testing methods:
(1) bulk density (g/l)—DIN 53420,
(2) percent shape restoration (%)—DIN 53577,
(3) deformation at break (mm)—DIN 53423,
(4) tensile strength (N/mm$^2$)—DIN 53571, and
(5) fire resistance—DIN 4102.

REFERENTIAL EXAMPLE 1

Preparation of a Dicarbonitrile (3)

In a 500-ml flask equipped with a stirrer, a thermometer, a liquid inlet tube and a condenser, 297.92 g, (2.50 moles) of bicyclo[2.2.1]hepta-5-ene-2-carbonitrile, 8.77 g (6.75 mmoles) of Ni[P(OC$_6$H$_5$)$_3$]$_4$, 4.80 g (35.22 mmoles) of ZnCl$_2$ and 32.27 g (0.104 mole) of P(OC$_6$H$_5$)$_3$ were charged. After the flask was fully purged with nitrogen gas, the reaction mixture was maintained at 65° C. under stirring. Into the flask, 94.59 g (3.50 moles) of ice-cooled liquid hydrocyanic acid were then charged at a flow rate of 45–55 ml/hr over three hours, followed by a further reaction for one hour.

The flask was again purged with nitrogen gas, followed by the addition of deionized water. The water layer so obtained was removed, whereby an oil was obtained in a semi-solid form. The oil was filtered and then was subjected to vacuum distillation, whereby 362.20 g of a mixture of bicyclo[2.2.1] heptane-2,5-dicarbonitrile and bicyclo[2.2.1]heptane-2,6-dicarbonitrile were obtained at 129°–137° C./1 mmHg (yield: 99.01%). The following is the results of an elemental analysis of the target product.

Elemental analysis:

|  | C | H | N |
| --- | --- | --- | --- |
| Found: | 73.9% | 6.9% | 19.2% |
| Calculated: | 73.94% | 6.90% | 19.16% |

REFERENTIAL EXAMPLE 2

Preparation of Bicyclo[2.2.1]heptane-2,5-dicarbonitrile

In a 2-l flask equipped with a stirrer, a thermometer and a reflux condenser, 179.0 g (1.2 moles) of 5-cyano-bicyclo [2.2.1]hepta-2-carbaldehyde, 292.6 g (1.3 moles) of N,O-bis(trifluoroacetyl)hydroxylamine, 197.8 g (2.5 moles) of pyridine and 600 ml of benzene were charged. The resulting mixture was gradually heated and refluxed for 3 hours under stirring. Deionized water (500 ml) was thereafter added to the reaction mixture. The water layer so obtained was removed, whereby an oil was obtained. The oil was distilled under reduced pressure, whereby 128.0 g of bicyclo[2.2.1] heptane-2,5-dicarbonitrile were obtained at 131°–136° C./1 mmHg (yield: 73%). The following is the results of an elemental analysis of the target product.

Elemental analysis:

|  | C | H | N |
| --- | --- | --- | --- |
| Found: | 74.0% | 6.9% | 19.1% |
| Calculated: | 73.94% | 6.90% | 19.16% |

REFERENTIAL EXAMPLE 3

Preparation of a Dicarbonitrile (4)

In a 500-ml flask equipped with a stirrer, a thermometer, a gas inlet tube and a condenser, 188.6 g of 4-cyanocyclohexene, 6.0 g of Ni[P(OC$_6$H$_5$)$_3$]$_4$, 3.0 g of ZnCl$_2$ and 23.9 g of P(OC$_6$H$_5$)$_3$ were charged. After the flask was fully purged with nitrogen gas, the reaction mixture was maintained at 75° C. under stirring. Into the flask, nitrogen-diluted hydrocyanic acid gas having a concentration of 42 mole % was then charged at a rate of 177.0 mmoles/hour for seven hours. After the flask was again purged with nitrogen gas, the reaction mixture was cooled. As a result of its analysis, a dicarbonitrile (4) was obtained in a yield of 64.9%.

Water and ethyl acetate, each 500 g, were added to the reaction mixture. After the resulting mixture was left over under stirring for 5 hours, the organic layer was separated. Ethyl acetate was then caused to evaporate, followed by vacuum distillation at 0.5–1.0 mmHg, whereby 132.0 g of a mixture of 1,3-cyclohexane dicarbonitrile and 1,4-cyclohexane dicarbonitrile were obtained as a 120°–130° C. fraction. As a result of its analysis, the fraction was found to consist of 64.4% of 1,3-cyclohexane dicarbonitrile and 35.6% of 1,4-cyclohexane dicarbonitrile. The following is the results of an elemental analysis of the target product.

Elemental analysis:

|  | C | H | N |
| --- | --- | --- | --- |
| Found: | 71.5% | 7.6% | 20.9% |
| Calculated: | 71.61% | 7.51% | 20.88% |

EXAMPLE 1

Preparation of a Diguanamine (1)

Figure 2A:
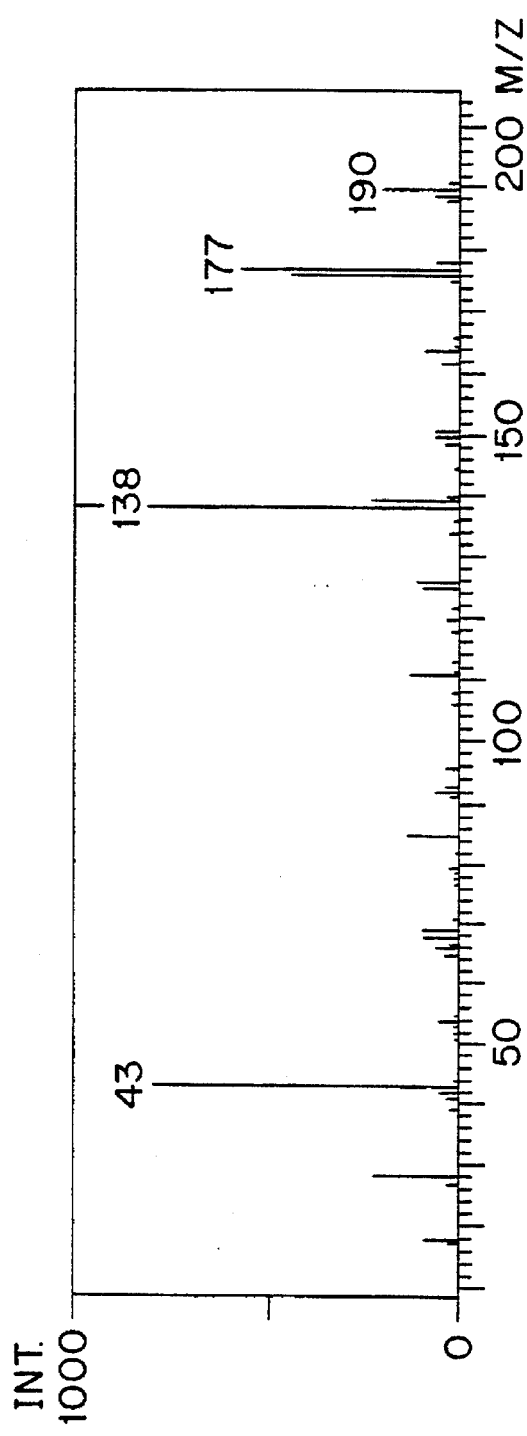
FIG. 2 is a mass spectrum of the compound obtained in Example 1.
Figure 2B:
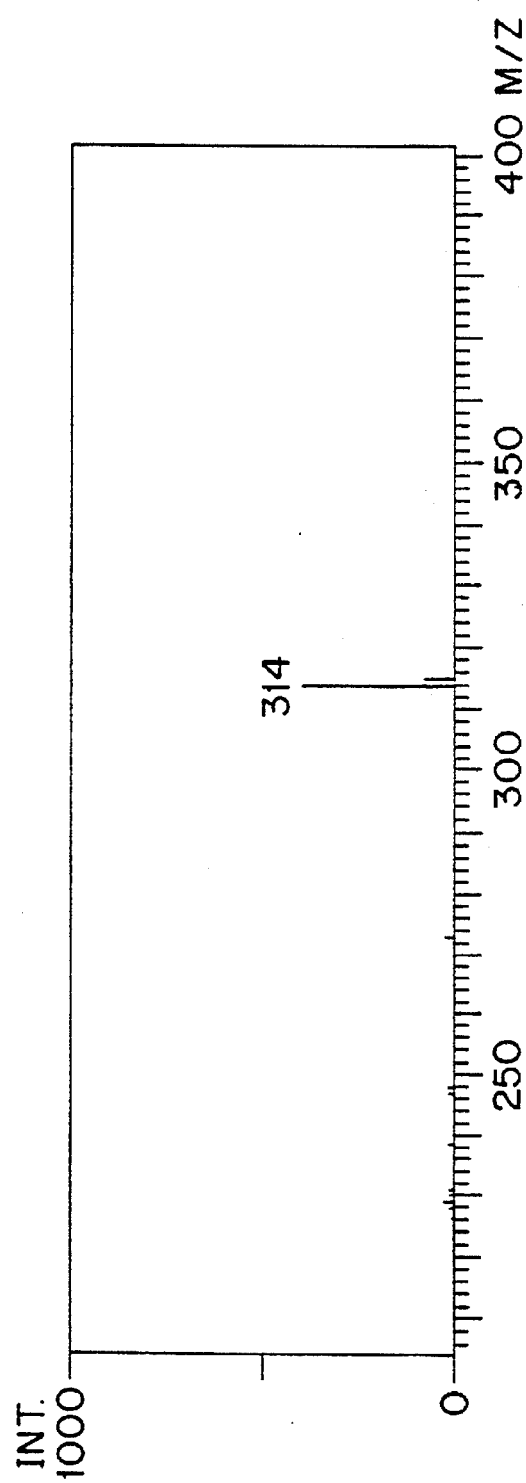

In a 3-l flask equipped with a stirrer, a thermometer and a reflux condenser, 146.2 g (1.0 mole) of the dicarbonitrile (3) prepared in the same manner as in Referential Example 1, 210.2 g (2.5 moles) of dicyandiamide, 16.8 g of potassium hydroxide and 1,000 ml of methyl cellosolve were charged, followed by gradual heating. The reaction mixture became transparent as its temperature arose. When the temperature approached about 105° C., the reaction proceeded rapidly with substantial exotherm so that the solvent was refluxed. Some time after the reflux started, the reaction mixture became turbid. The resulting mixture was reacted at 120°–125° C. for 10 hours under stirring. Subsequent to removal of the solvent from the reaction mixture, 3 l of deionized water were poured. The resulting white precipitate was collected by filtration. The solid so obtained was washed with deionized water and then with methanol, followed by vacuum drying. The resulting solid was dissolved in ethyl cellosolve, to which deionized water was added to conduct precipitation. The precipitate was collected by filtration. The solid so obtained was washed with water and then dried in a vacuum, whereby 2,5-bis(4,6-diamino-1,3,5-triazin-2-yl)-bicyclo[2.2.1]heptane and 2,5-bis(4,6-diamino-1,3,5-triazin-2-yl)bicyclo[2.2.1]heptane were obtained as a mixture in the form of white powdery crystals having a melting point of 317°–324° C. (as measured by DSC). Incidentally, as a result of an analysis of the reaction mixture (before treatment) by liquid chromatography, it was found that, based on the amount of the dicarbonitrile (3) charged, the yield (mole %) of the diguanamine (1) was 98.2% and that of compounds other than the raw materials and the target compound was 0.08 wt. %. The results of an elemental analysis and $^1$H nuclear magnetic resonance spectrum analysis of the target compound are presented below. In addition, the results of an infrared ray absorption spectrum analysis and mass spectrum analysis of the target compound are shown in FIG. 1 and FIG. 2, respectively.

Elemental analysis:

|  | C | H | N |
| --- | --- | --- | --- |
| Found: | 49.7% | 5.8% | 44.5% |
| Calculated: | 49.67% | 5.77% | 44.56% |

$^1$H Nuclear magnetic resonance spectrum analysis (internal standard substance: TMS, solvent: $d_6$-DMSO)

Absorption based on $NH_2$ groups, δ 6.50 ppm (singlet), 6.72 ppm (singlet)

EXAMPLE 2

Preparation of 2,5-bis(4,6-diamino-1,3,5-triazin-2-yl)-bicyclo[2.2.1]heptane

In a similar manner to Example 1 except that 146.2 g (1.0 mole) of the dicarbonitrile (3) prepared in the same manner as in Referential Example 1 were replaced by 160.8 g (1.1 moles) of bicyclo[2.2.1]heptane-2,5-dicarbonitrile prepared in the same manner as in Referential Example 2, a reaction was conducted and the resulting reaction mixture was treated. The solid so obtained was subjected to vacuum drying, whereby 2,5-bis(4,6-diamino-1,3,5-triazin-2-yl)-bicyclo[2.2.1]heptane was obtained as white powdery crystals having a melting point of 318°–321° C. (as measured by DSC). Incidentally, as a result of an analysis of the reaction mixture (before treatment) by liquid chromatography, it was found that the yield of the diguanamine (1) was 96.4 mole % based on the amount of the dicarbonitrile (3) charged. In an infrared absorption spectrum of the target compound, the nitrile-based absorption (at 2235 $cm^{-1}$) of the raw material compound disappeared and instead, a triazine-ring-based absorption was observed at 821 $cm^{-1}$. Its elemental analysis data were found to conform well with the calculated values as shown below.

Elemental analysis:

|  | C | H | N |
| --- | --- | --- | --- |
| Found: | 49.7% | 5.7% | 44.6% |
| Calculated: | 49.67% | 5.77% | 44.56% |

EXAMPLE 3

Preparation of a Diguanamine (2)

In a 3-l flask equipped with a stirrer, a thermometer and a reflux condenser, 134.2 g (1.0 mole) of the dicarbonitrile (4) prepared in the same manner as in Referential Example 3, 210.2 g (2.5 moles) of dicyandiamide, 16.8 g of potassium hydroxide and 1,000 ml of methyl cellosolve were charged, followed by gradual heating. The reaction mixture became transparent as its temperature arose. When the temperature approached about 105° C., the reaction proceeded rapidly with substantial exotherm so that the solvent was refluxed. Some time after the reflux started, the reaction mixture became turbid. The resulting mixture was reacted at 120°–125° C. for 10 hours under stirring.

Figure 3:
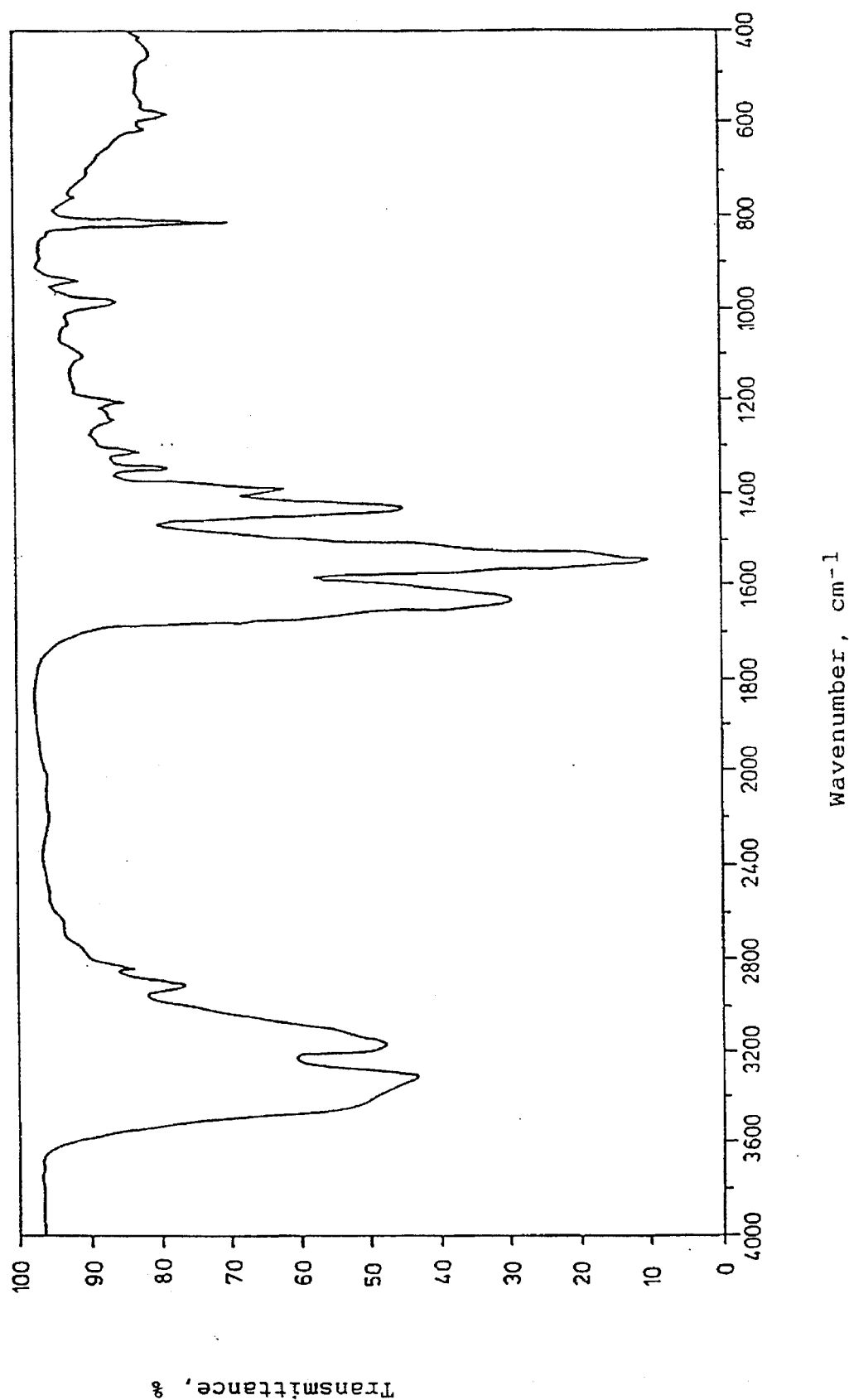
FIG. 3 is an infrared absorption spectrum of a compound obtained in Example 3.
Figures 4A, 4B:
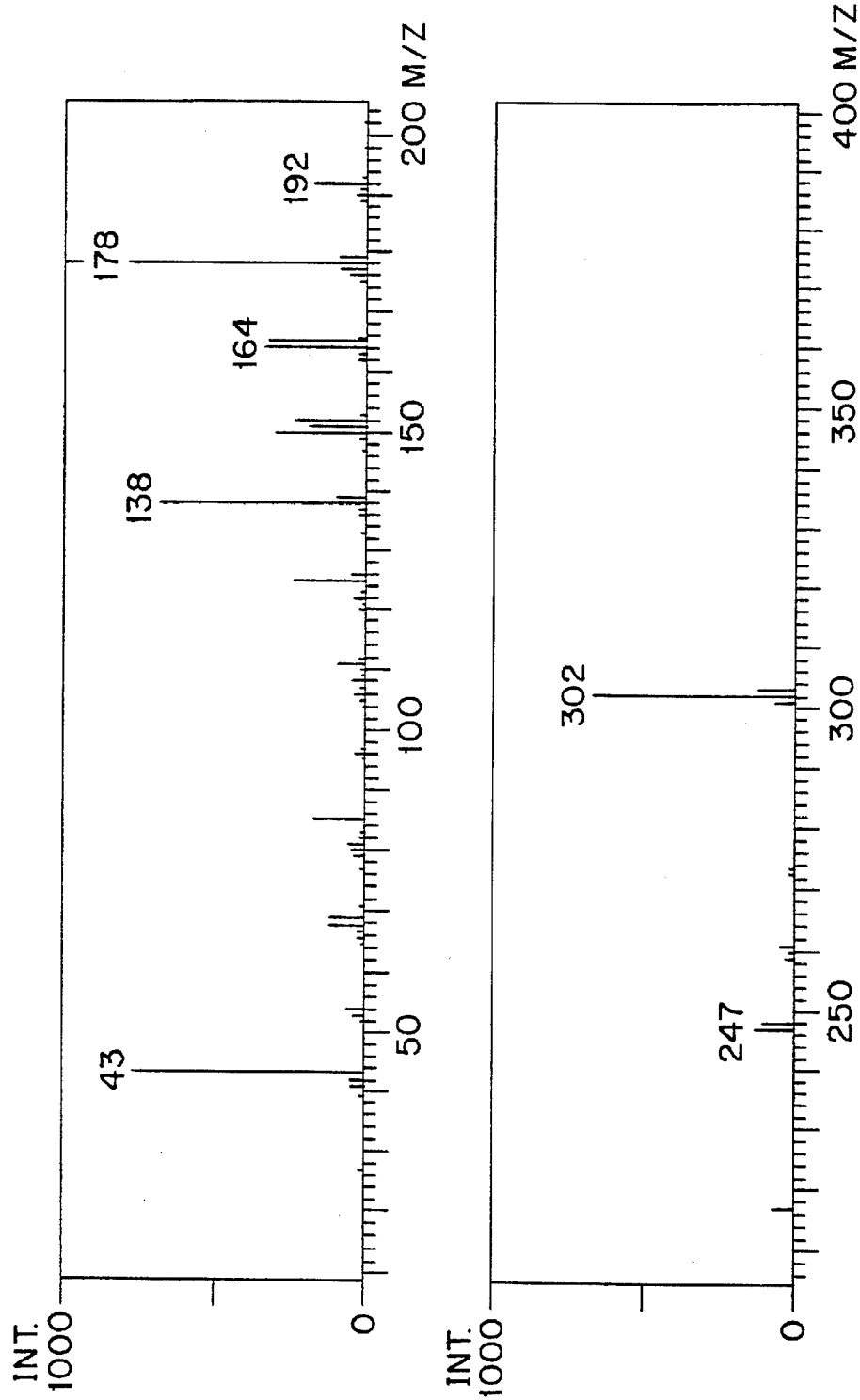
FIG. 4 is a mass spectrum of the compound obtained in Example 3.

Subsequent to the removal of the solvent from the reaction mixture, 3 l of deionized water were poured. The resulting white precipitate was collected by filtration. The solid so obtained was washed with deionized water and then with methanol, followed by vacuum drying. The resulting solid was dissolved in ethyl cellosolve, to which deionized water was added to induce reprecipitation. The precipitate so formed was collected by filtration. The solid so obtained was washed with water and then dried in a vacuum, whereby 1,3-bis(4,6-diamino-1,3,5-triazin-2-yl)-cyclohexane and 1,4-bis(4,6-diamino-1,3,5-triazin-2-yl)cyclohexane were obtained as a mixture in the form of white powdery crystals having a melting point of 317°–321° C. (as measured by DSC). Incidentally, as a result of an analysis of the reaction mixture (before treatment) by liquid chromatography, it was found that, based on the amount of the dicarbonitrile (4) charged, the yield of the diguanamine (2) was 97.3 mole % and that of the compound(s) except the raw materials and the target compound was 0.12 wt. %. The results of an elemental analysis and $^1$H nuclear magnetic resonance spectrum analysis of the target compound are presented below. In addition, the results of an infrared ray absorption spectrum analysis and a mass spectrum analysis of the target compound are shown in FIG. 3 and FIG. 4, respectively.

Elemental analysis:

|  | C | H | N |
|---|---|---|---|
| Found: | 47.6% | 6.1% | 46.3% |
| Calculated: | 47.67% | 6.00% | 46.33% |

$^1$H Nuclear magnetic resonance spectrum analysis (internal standard substance: TMS, solvent: $d_6$-DMSO)

Absorption based on $NH_2$ groups, δ: 6.49 ppm (singlet)

EXAMPLE 4

Preparation of 1,4-bis(4,6-diamino-1,3,5-triazin-2-yl)-cyclohexane

In a similar manner to Example 3 except that 134.2 g (1.0 mole) of the dicarbonitrile (4) prepared in the same manner as in Referential Example 3 were replaced by 147.6 g (1.1 moles) of 1,4-cyclohexane dicarbonitrile, a reaction was conducted and the resulting reaction mixture was treated. The solid so obtained was subjected to vacuum drying, whereby 1,4-bis(4,6-diamino-1,3,5-triazin-2-yl)-cyclohexane was obtained as white powdery crystals having a melting point of 319°–322° C. (as measured by DSC). Incidentally, as a result of an analysis of the reaction mixture (before treatment) by liquid chromatography, it was found that, based on the amount of the dicarbonitrile (4) charged, the yield of the diguanamine (2) was 95.8 mole %. In an infrared absorption spectrum of the target compound, it was found that the nitrile-based absorption (at 2237 cm$^{-1}$) of the raw material compound disappeared and instead, a triazine-ring-based absorption was newly observed at 821 cm$^{-1}$. Its elemental analysis data were found to conform well with the calculated values as shown below.

Elemental analysis:

|  | C | H | N |
|---|---|---|---|
| Found: | 47.7% | 6.1% | 46.2% |
| Calculated: | 47.67% | 6.00% | 46.33% |

$^1$H Nuclear magnetic resonance spectrum (internal standard substance: TMS, solvent: $d_6$-DMSO)

Absorption based on $NH_2$ groups δ: 6.50 ppm (singlet)

EXAMPLE 5

Preparation of 1,2-bis(4,6-diamino-1,3,5-triazin-2-yl)-cyclohexane

In a similar manner to Example 3 except that 134.2 g (1.0 mole) of the dicarbonitrile (4) prepared in the same manner as in Referential Example 3 were replaced by 134.2 g (1.0 mole) of 1.2-cyclohexane dicarbonitrile, a reaction was conducted and the resulting reaction mixture was treated. The solid so obtained was subjected to vacuum drying, whereby 1,2-bis(4,6-diamino-1,3,5-triazin-2-yl)-cyclohexane was obtained as white powdery crystals. In an infrared absorption spectrum of the target compound, the nitrile-based absorption of the raw material compound disappeared and instead, a triazine-ring based absorption was newly observed. Its elemental analysis data were found to conform well with the calculated value as shown below.

Elemental analysis:

|  | C | H | N |
|---|---|---|---|
| Found: | 47.7% | 6.0% | 46.3% |
| Calculated: | 47.67% | 6.00% | 46.33% |

EXAMPLE 6

Preparation of Diguanamines (1)

In a similar manner to Example 1 except that the charged amount (in moles) of dicyandiamide and the reaction solvent were changed, reactions were conducted and the reaction mixtures so obtained were treated. The yields of the target compounds, diguanamines (1), are shown in Table 1.

TABLE 1

|  | Amount of dicyandiamide charged (moles) | Reaction solvent | Yield* of diguanamine (1) [based on dicarbonitrile (3) charged (mole %)] |
|---|---|---|---|
| Example 6-1 | 2.2 | Ethyl cellosolve | 95.8 |
| Example 6-2 | 2.5 | Ethylene glycol | 97.0 |
| Example 6-3 | 2.5 | A mixed solvent of dimethyl sulfoxide/ methyl cellosolve (weight ratio: 1/1) | 98.2 |

*Calculated based on the results of liquid chromatography of each reaction mixture (before treatment)

EXAMPLE 7

Preparation of a Diguanamine (1)

In a 3-l flask equipped with a stirrer, a thermometer and a reflux condenser, 146.2 g (1.0 mole) of the dicarbonitrile (3) obtained in the same manner as in Referential Example 1, 210.2 g (2.5 moles) of dicyandiamide, 54.0 g of sodium methylate and 1,000 ml of dimethyl sulfoxide were charged, followed by gradual heating. When the temperature approached about 105° C., the reaction proceeded rapidly with substantial exotherm. The temperature was thereafter raised gradually to 140° C., followed by reaction at 140°–145° C. for 2 hours under stirring.

The reaction mixture so obtained was treated in a similar manner to Example 1, whereby 2,5-bis(4,6-diamino-1,3,5-triazin-2-yl)-bicyclo[2.2.1]heptane and 2,6-bis(4,6-diamino-1,3,5-triazin-2-yl)-bicyclo[2.2.1]heptane was obtained as a mixture. Incidentally, as a result of an analysis of the reaction mixture (before treatment) by liquid chromatography, it was found that, based on the amount of the dicarbonitrile (3) charged, the yield of the diguanamine (1) was 95.7 mole %.

EXAMPLE 8

Preparation of Diguanamines (2)

In a similar manner to Example 3 except that the charged amount (in moles) of dicyandiamide and the reaction solvent were changed, reactions were conducted and the reaction mixtures so obtained were treated. The yields of the target compounds, diguanamines (2), are shown in Table 2.

TABLE 2

| | Amount of dicyandiamide charged (moles) | Reaction solvent | Yield** of diguanamine (2) [based on dicarbonitrile (4) charged (mole %)] |
|---|---|---|---|
| Example 8-1 | 2.5 | Isopropyl cellosolve | 96.1 |
| Example 8-2 | 1.7 | N,N-dimethylacetamide | 61.5 |
| Example 8-3 | 2.5 | Sulforan | 98.2 |
| Example 8-4 | 3.0 | A mixed solvent of dimethyl sulfoxide/methyl cellosolve (weight ratio: 1/1) | 98.6 |

**Calculated based on the results of liquid chromatography of each reaction mixture (before treatment)

EXAMPLE 9

Preparation of 1,4-bis(4,6-diamino-1,3,5-triazin-2-yl)cyclohexane

In a 3-1 flask equipped with a stirrer, a thermometer and a reflux condenser, 134.2 g (1.0 mole) of 1,4-cyclohexane dicarbonitrile, 210.2 g (2.5 moles) of dicyandiamide, 54.0 g of sodium methylate and 1,000 ml of dimethyl sulfoxide were charged, followed by gradual heating. The reaction mixture became transparent as its temperature arose. When the temperature approached about 105° C., the reaction proceeded rapidly with substantial exotherm. The temperature was thereafter raised to 140° C., followed by reaction at 140°–145° C. for 2 hours under stirring.

The reaction mixture so obtained was treated in a similar manner to Example 3, whereby 1,4-bis(4,6-diamino-1,3,5-triazin-2-yl)-cyclohexane was obtained as white powdery crystals. Incidentally, as a result of an analysis of the reaction mixture (before treatment) by liquid chromatography, it was found that the yield of the diguanamine (2) was 99.1 mole % based on the amount of the dicarbonitrile (4) charged.

According to the preparation process of the present invention which can provide a diguanamine by reacting a particular dicarbonitrile and dicyandiamide while suitably selecting a reaction catalyst, a solvent, a reaction temperature, the molar ratio of the raw materials and/or the like, the target compound can be obtained with extremely minimized byproducts and high purity and in a high yield as demonstrated above in Examples 1–9. The process, including the purification step, is easy to practice and is excellent.

EXAMPLE 10

Preparation of an N-methylol Derivative of a Diguanamine (1) and Water Dilution Test of the Derivative To 15.7 g (0.05 mole) of the diguanamine (1) obtained in the same manner as in Example 1, 42.2 g of 37% formalin (0.52 mole in terms of 100% formaldehyde) which had been adjusted to pH 10.5 with a 10% aqueous solution of sodium hydroxide were added. The resulting mixture was heated at 60°–65° C. for 30 minutes under stirring. The reaction mixture was homogeneous and clear. As a result of its analysis, it was found that 7.2 moles of formaldehyde were methylol-bonded to one mole of the diguanamine (1).

To the resulting solution of the N-methylol derivative, 50 g of deionized water were gradually added at room temperature. The solution so obtained was also homogeneous and clear.

EXAMPLE 11

Preparation of an N-methylol Derivative of a Diguanamine (2) and a Water Dilution Test of the Derivative To 15.1 g (0.05 mole) of the diguanamine (2) obtained in the same manner as in Example 3, 42.2 g of 37% formalin (0.52 mole in terms of 100% formaldehyde) which had been adjusted to pH 10.5 with a 10% aqueous solution of sodium hydroxide were added. The resulting mixture was heated at 60°–65° C. for 30 minutes under stirring.

The reaction mixture was homogeneous and clear. As a result of its analysis, it was found that 7.3 moles of formaldehyde were methylol-bonded to one mole of the diguanamine (2).

To the resulting solution of the N-methylol derivative, 50 g of deionized water were gradually added at room temperature. The solution so obtained was also homogeneous and clear.

As demonstrated in Examples 10 and 11, the N-methylol derivative of each diguanamine according to the present invention has been found to have excellent water reducibility so that it is excellent as a raw material for a resin to be used in an aqueous system such as a water-base paint resin and is extremely useful for a wide variety of applications.

COMPARATIVE EXAMPLE 1

Preparation of an N-methylol Derivative of Phthaloguanamine and a Water Dilution Test of the Derivative In a similar manner to Example 10 except 14.8 g (0.05 mole) of o-phthaloguanamine were used instead of 15.7 g (0.05 mole) of the diguanamine (1) obtained in the same manner as in Example 1, a reaction was conducted.

The reaction mixture contained a large amount of an insoluble solid so that it was subjected to solid-liquid separation by hot filtration. The solid was dried under reduced pressure, whereby 13.7 g of crystals, which were found to contain 13.6 g (0.046 mole) of o-phthaloguanamine as a result of an elemental analysis, were obtained. Deionized water (1.0 g) was then added to the filtrate at room temperature, whereby substantial turbidity occurred.

COMPARATIVE EXAMPLE 2

Preparation of an N-methylol Derivative of Spiroguanamine and a Water Dilution Test of the Derivative In a similar manner to Example 10 except 15.7 g (0.05 mole) of the diguanamine (1) obtained in the same manner as in Example 1 were replaced by 21.7 g (0.05 mole) of 3,9-bis[2-(3,5-diamino-2,4,6-triazaphenyl)ethyl]-2,4,8,10-tetraoxaspiro[5.5]undecane] ("CTU guanamine"; product of Ajinomoto Co., Inc.), a reaction was conducted.

The reaction mixture so obtained contained a large amount of an insoluble solid so that it was subjected to solid-liquid separation by hot filtration. The solid was dried under reduced pressure, whereby 18.3 g of crystals, which were found to contain 18.2 g (0.042 mole) of CTU guanamine as a result of an elemental analysis, were obtained. Deionized water (1.0 g) was then added to the filtrate at room temperature, whereby substantial turbidity occurred.

As have been demonstrated above in Comparative Examples 1 and 2, methylol-forming reaction of phthaloguanamine and spiroguanamine with aldehydes are extremely slow. The amino groups in such compounds have poor reactivity, so that it is difficult to produce resin intermediates, such as co-condensates with melamine, guanamines or ureas, or various derivatives. Further, the N-methylol derivatives of such compounds have extremely poor water reducibility. It is hence difficult to employ them as raw materials for resins to be used in aqueous systems, such as water-base paint resins. Moreover, substantial limitations are imposed on their applications.

EXAMPLE 12

Preparation of an N-methylol Derivative of a Diguanamine (1)

To 15.7 g (0.05 mole) of the diguanamine (1) obtained in the same manner as in Example 1, 17.9 g of 37% formaldehyde (0.22 mole in terms of 100% formaldehyde) which had been adjusted to pH 9.0 with a 5% aqueous solution of sodium carbonate were added. The resulting mixture was heated at 70°–75° C. for 30 minutes under stirring. The reaction mixture was clear. As a result of an analysis of the mixture, it was found that 4.0 moles of formaldehyde were methylol-bonded with one mole of the diguanamine (1).

EXAMPLE 13

Preparation of an N-methylol Derivative of a Diguanamine (1)

To 15.7 g (0.05 mole) of the diguanamine (1) obtained in the same manner as in Example 1, 19.9 g (0.32 mole) of methylhemiformal and 40.0 g of methanol were added, followed by the adjustment to pH 9.5 with a 20% aqueous solution of potassium hydroxide. The resulting mixture was heated at 60° C. for one hour under stirring. The reaction mixture was clear. As a result of an analysis of the mixture, it was found that 6.1 moles of formaldehyde were methylol-bonded with one mole of the diguanamine (1).

EXAMPLE 14

Preparation of an N-methylol derivative of a diguanamine (1)

To 15.7 g (0.05 mole) of 2,5-bis(4,6-diamino-1,3,5-triazin-2-yl)-bicyclo[2.2.1]heptane obtained in the same manner as in Example 2, 81.2 g of 37% formalin (1.0 mole in terms of 100% formaldehyde) which had been adjusted to pH 10.5 with a 5% aqueous solution of sodium hydroxide were added. The resulting mixture was heated at 60° C. for one hour under stirring. The reaction mixture was clear. As a result of an analysis of the mixture, it was found that 7.8 moles of formaldehyde were methylol-bonded to one mole of 2,5-bis-(4,6-diamino-1,3,5-triazin-2-yl)-bicyclo[2.2.1] heptane.

EXAMPLE 15

Preparation of an N-methoxymethyl derivative of a diguanamine (1)

Under reduced pressure, the N-methylol derivative of 5.0 g of the diguanamine (1), said derivative being a reaction mixture prepared in the same manner as in Example 10 and being formed of formaldehyde and the diguanamine bonded together at a molar ratio of 7.2:1, was dehydrated, followed by the addition of 50 ml of methanol. After being adjusted to pH 2.0 with a 20% nitric acid, the resulting mixture was heated at 40°–45° C. for 2 hours. The reaction mixture was adjusted to pH 8.0 with a 10% aqueous solution of sodium hydroxide. From the solution, methanol and water were removed under reduced pressure and then a solid was then filtered off, whereby a viscous liquid was obtained. As a result of an analysis of the liquid, it was found that 5.3 equivalents of N-methoxymethyl groups were bonded to one mole of the diguanamine (1).

EXAMPLE 16

Preparation of an N-methoxymethyl derivative of a diguanamine (2)

Under reduced pressure, the N-methylol derivative of 5.0 g of the diguanamine (2), said derivative being a reaction mixture prepared in the same manner as in Example 11 and being formed of formaldehyde and the diguanamine bonded together at a molar ratio of 7.3:1, was dehydrated, followed by the addition of 50 ml of methanol. After being adjusted to pH 2.0 with a 20% nitric acid, the resulting mixture was heated at 40°–45° C. for 2 hours. The reaction mixture was adjusted to pH 8.0 with a 10% aqueous solution of sodium hydroxide. From the solution, methanol and water were removed under reduced pressure and a solid was then filtered off, whereby a viscous liquid was obtained. As a result of an analysis of the liquid, it was found that 4.9 equivalents of N-methoxymethyl groups were bonded to one mole of the diguanamine (2).

As is understood from Examples 15 and 16, the N-methylol derivative of each diguanamine, said derivative pertaining to the present invention, readily undergoes an alkyl-etherification reaction with an alcohol under mild conditions, thus having excellent reactivity and can provide N-alkoxymethylated derivatives of the N-methylol derivative, said alkoxymethylated derivatives being extremely useful as resin intermediates.

EXAMPLE 17

Preparation of a primary condensate of N-methylol diguanamine (2)

To 15.1 g (0.05 mole) of the diguanamine (2) obtained in the same manner as in Example 4, 13.1 g of paraformaldehyde (80% grade) (0.35 mole in terms of 100% formaldehyde) and 50 ml of methanol were added. The resulting solution was adjusted to pH 13.2 with a 20% aqueous solution of potassium hydroxide under stirring, followed by heating at 80° C. for one hour under stirring. After the completion of the heating, the reaction mixture was adjusted to pH 8.0 with a 10% aqueous solution of hydrochloric acid. The resulting precipitate was filtered off, whereby a clear solution was obtained. As a result of an analysis of the resinous product obtained by the solvent removal of the clear solution, it was found to be a primary condensate of N-methylol diguanamine, said condensate being formed of the diguanamine (2) and formaldehyde methylol-bonded at a ratio of 6.0 moles of the latter to one structural unit of the former and having an average addition condensation degree of 1.3.

EXAMPLE 18

Preparation of a primary condensate of a diguanamine (1)

To 15.7 g (0.05 mole) of the diguanamine (1) obtained in the same manner as in Example 1, 18.8 g of paraformaldehyde (80% grade) (0.5 mole in terms of 100% formaldehyde) and 50 ml of n-butanol were added. Under stirring, the solution was adjusted to pH 11.0 with a 10% aqueous solution of sodium hydroxide. The reaction mixture was heated at 60° C. for 30 minutes under stirring, followed by the adjustment to pH 3.0 with a 20% aqueous solution of nitric acid. The reaction mixture was heated for 2 hours under reflux temperature conditions and stirring while being dehydrated. After the completion of the heating, the reaction mixture was adjusted to pH 8.0 with a 10% aqueous solution of sodium hydroxide. The resulting precipitate was filtered off, whereby a homogeneous and clear solution was obtained. As a result of an analysis of the resinous product obtained by the solvent removal of the solution, it was found to be a primary condensate of an etherified diguanamine formed of the diguanamine (1) and formaldehyde methylol-bonded at a ratio of 1.9 moles of the latter to one structural unit of the former, containing butyl ether groups and having an average addition condensation degree of 1.6.

EXAMPLE 19

Polymerization of an N-methylol derivative of a diguanamine and ultraviolet light resistance test of the resin so obtained In 10 ml of n-butyl alcohol, 5.0 g of an N-methylol derivative of the diguanamine (1), which had been obtained in the same manner as in Example 10 and was formed of the diguanamine (1) and formaldehyde bonded together at a ratio of 7.2 moles of the latter to one mole of the former, were dissolved, followed by the addition of 0.025 g of p-toluenesulfonic acid as a curing catalyst. The resulting solution was coated on a galvanized sheet steel and then, heated and cured at 140° C. for 20 minutes.

Using a germicidal lamp (manufactured by Toshiba Corporation; 19W) as an ultraviolet light source, the sheet steel so coated, that is, a test sheet steel, was exposed for 200 hours to ultraviolet light at a vertical distance of 25 cm. The surface gloss of the test sheet steel was measured in accordance with JIS K 5400 (specular reflection at 60°). As a result, the gloss retention was found to be 97%.

EXAMPLE 20

Polymerization of an N-methylol derivative of a diguanamine and ultraviolet light resistance test of the resin so obtained In 10 ml of n-butyl alcohol, 5.0 g of an N-methylol derivative of the diguanamine (2), which had been obtained in the same manner as in Example 11 and was formed of the diguanamine (2) and formaldehyde bonded together at a molar ratio of 7.3:1, were dissolved, followed by the addition of 0.025 g of p-toluenesulfonic acid as a curing catalyst. The resulting solution was coated on a galvanized sheet steel and then, heated and cured at 140° C. for 20 minutes.

Using a germicidal lamp (manufactured by Toshiba Corporation; 19W) as an ultraviolet light source, the sheet steel so coated, that is, a test sheet steel, was exposed for 200 hours to ultraviolet light at a vertical distance of 25 cm. The surface gloss of the test sheet steel was measured in accordance with JIS K 5400 (specular reflection at 60°). As a result, the gloss retention was found to be 98%.

As has been shown in Examples 19 and 20, the N-methylol derivatives of diguanamines, said derivatives relating to the present invention, had excellent properties including superb polymerizability and an extremely small deterioration in gloss under ultraviolet rays.

EXAMPLE 21

Crease resistance test of a fiber treatment containing an N-methylol derivative of a diguanamine Deionized water was added to an N-methylol derivative of the diguanamine (1), which had been prepared in the same manner as in Example 10 and was formed of the diguanamine (1) and formaldehyde bonded together at a molar ratio of 7.2:1, to prepare its 10 wt. % aqueous solution. To the solution, 3 wt. % (relative to the solid content of the derivative) of ammonium secondary phosphate were added as a catalyst. A cotton cloth (cotton broadcloth No. 60) was dipped in the resulting solution, followed by padding. The cloth was subjected to preliminary drying at 80° C. for 5 minutes and then, heated at 140° C. for 5 minutes.

A crease resistance test was conducted in accordance with JIS L 1059 (Monsanto method), using the cloth so treated. As a result, it was found that the cloth had a crease resistance of 86%, thus exhibiting excellent crease resistance.

Each N-methylol derivative of a diguanamine, said derivative pertaining to the present invention, can impart, as demonstrated above, excellent crease resistance and the like to fibers when they are treated with the derivative. A thermosetting composition containing the diguanamine derivative therein is therefore extremely useful as a fiber treatment.

EXAMPLE 22

Curing test of a water-base paint resin containing an N-methylol derivative of a diguanamine To a solution obtained by gradually adding 1.84 g of dimethylethanolamine to 40.0 g of "Almatex WA 911" (product of Mitsui Toatsu Chemicals, Inc., NV: 60%) under stirring and then adjusting its nonvolatile content to 20% with deionized water, a 50 wt. % aqueous solution of 6.0 g of an N-methylol derivative of the diguanamine (1), which had been prepared in the same manner as in Example 10 and was formed of formaldehyde and the diguanamine (1) bonded together at a molar ratio of 7.2:1, was added and mixed. The resulting resin solution so obtained was coated on a galvanized sheet steel and then, heated at 160° C. for 20 minutes.

On the coating film of the steel sheet so coated, cissing, blisters, discoloration or the like was not observed at all. The surface gloss of the coating film was measured in accordance with JIS K 5400 (specular reflection at 60°). As a result, the film was found to have a surface gloss of 98%, thus exhibiting outstanding smoothness and gloss. Furthermore, no peeling was observed on the film even after rubbing the film surface 50 times with an acetone-soaked cloth. It was, therefore, a fully cured and excellent coating film.

EXAMPLE 23

Curing test of a water-base paint resin containing an N-methylol derivative of a diguanamine To a solution obtained by gradually adding 1.84 g of dimethylethanolamine to 40.0 g of "Almatex WA 911" (product of Mitsui Toatsu Chemicals, Inc., NV: 60%) under stirring and then adjusting its nonvolatile content to 20% with deionized water, a 50 wt. % aqueous solution of 5.9 g of an N-methylol derivative of the diguanamine (2), which had been prepared in the same manner as in Example 11 and was formed of formaldehyde and the diguanamine (2) bonded together at a molar ratio of 7.3:1, was added and mixed. The resulting resin solution so obtained was coated on a galvanized sheet steel and then, heated at 160° C. for 20 minutes.

On the coating film of the steel sheet, cissing, blisters, discoloration or the like was not observed at all. The surface gloss of the coating film was measured in accordance with JIS K 5400 (specular reflection at 60°). As a result, the film was found to have a surface gloss of 94%, thus exhibiting outstanding smoothness and gloss. Furthermore, no peeling was observed on the film even after rubbing the film surface 50 times with an acetone-soaked cloth. It was, therefore, a fully cured and excellent coating film.

As has been demonstrated in Examples 21–23, each diguanamine derivative according to the present invention has excellent water reducibility and a thermosetting composition containing the derivative therein is not only excellent as a resin to be used in an aqueous system, such as a water-base paint resin, adhesive resin or fiber treatment but also exhibits excellent curing .and crosslinking properties when used as a paint resin. It is therefore extremely useful for a wide variety of applications.

EXAMPLE 24

Curing test of a water-base paint resin containing an N-methoxymethyl derivative of a diguanamine To a solution obtained by gradually adding 1.84 g of dimethylethanolamine to 40.0 g of "Almatex WA 911" (product of Mitsui Toatsu Chemicals, Inc., NV: 60%) under stirring and then adjusting its nonvolatile content to 20% with deionized water, a 50 wt. % solution of 6.8 g of an N-methoxymethyl derivative of the diguanamine (1), which had been prepared in the same manner as in Example 15 and was formed of formaldehyde and the diguanamine (1) bonded together at a molar ratio of 5.3:1, in a 50:50 (by weight) mixed solvent of butyl cellosolve and water as well as 0.15 g of p-toluenesulfonic acid were added and mixed. The resulting resin solution so obtained was coated on a galvanized sheet steel and then, heated at 160° C. for 20 minutes.

On the coating film of the steel sheet, cissing, blisters, discoloration or the like was not observed at all. The surface gloss of the film was measured in accordance with JIS K 5400 (specular reflection at 60°). As a result, the film was found to have a surface gloss of 96%, thus exhibiting outstanding smoothness and gloss. Furthermore, no peeling was observed on the film even after rubbing the film surface 50 times with an acetone-soaked cloth. It was, therefore, a fully cured and excellent coating film.

As has been demonstrated above, each etherified diguanamine according to the present invention has excellent polymerizability and in addition, a thermosetting resin composition which contains the etherified diguanamine and a resin reactive therewith and therefore curable is extremely useful as a water-base paint resin.

EXAMPLE 25

Polymerization of an N-methoxymethylated diguanamine and a weathering test of the resin so obtained.

In 10 g of methyl isobutyl ketone, 4.9 g of an N-methoxymethyl derivative of the diguanamine (2), which had been obtained in the same manner as in Example 16 and was formed of formaldehyde and the diguanamine (2) bonded together at a molar ratio of 4.9:1, were dissolved. To the resulting solution, 47.2 g of "Almatex 646" (product of Mitsui Toatsu Chemicals, Inc., NV: 60%) were added and mixed. The resulting resin solution was coated on a galvanized sheet steel and then, cured by heating it at 180° C. for 50 minutes.

An exposure test of the sheet steel thus coated was conducted for 500 hours using a weather-o-meter. Neither blisters nor discoloration was observed on the surface of the coating film of the sheet steel. The surface gloss of the coating film was measured in accordance with JIS K 5400 (specular reflection at 60°).

As a result, the gloss retention was found to be 95%.

EXAMPLE 26

Polymerization of a primary condensate of etherified diguanamine and a weathering test of the condensate so obtained.

In 10 g of methyl isobutyl ketone, 5.0 g of a primary condensate of the etherified diguanamine (1), which had been obtained in the same manner as in Example 18 and had an average addition condensation degree of 1.6 per structural unit of the diguanamine (1) were dissolved. To the resulting solution, 47.2 g of "Almatex P 646" (product of Mitsui Toatsu Chemicals, Inc., NV: 60%) were added and mixed. The resulting resin solution was coated on a galvanized sheet steel and then, cured by heating it at 160° C. for 30 minutes.

An exposure test of the sheet steel thus coated was conducted for 500 hours using a weather-o-meter. Neither blisters nor discoloration was observed on the surface of the coating film of the sheet steel. The surface gloss of the coating film was measured in accordance with JIS K 5400 (specular reflection at 60°). As a result, the gloss retention was found to be 97%.

As has been demonstrated in Examples 25 and 26, each of etherified diguanamines and these primary condensates according to the present invention have excellent polymerizability. In addition, a cured product obtained from a thermosetting resin composition containing therein the etherified derivative or the primary condensate and a resin curable through a reaction therewith has excellent weather resistance. It is, therefore, extremely useful as a paint resin.

EXAMPLE 27

Curing test of an epoxy-containing resin with a diguanamine (1)

Dissolved in 100.0 g of butyl cellosolve were 100 g of an epoxy-containing resin ("Epicoat #828"; product of Shell Kagaku K. K.). To the resulting solution, 19.6 g of the diguanamine (1) prepared in the same manner as in Example 1 were added and dissolved, whereby a resin solution was prepared. The resin solution was coated on a galvanized sheet steel, followed by heating at 110° C. for 30 minutes and then, 200° C. for 40 minutes. No peeling was observed on the coating film of-the sheet steel so heated even after rubbing the film surface 50 times with a toluene-soaked cloth. It was a-fully cured, transparent, excellent coating film.

EXAMPLE 28

Curing test of an epoxy-containing resin with a diguanamine (2)

In a similar manner to Example 27 except that 18.9 g of the diguanamine (2) prepared in the same manner as in Example 3 were used instead of 19.6 g of the diguanamine (1) prepared in the same manner as in Example 1, a resin solution was prepared and a coating film curing test of the film was conducted.

No peeling was observed on the coating film of the sheet steel so heated even after rubbing the film surface 50 times with a toluene-soaked cloth. It was a fully cured, transparent, excellent coating film.

similar manner to the above except the dicyandiamide was used instead of the diguanamine in its optimum blending amount, and its Charpy impact resistance was measured.

TABLE 4

|  | Amount of EP#828, an epoxy-containing resin, blended | Amount of a diguanamine or dicyandiamide blended | Curing Conditions | Charpy impact strength (kg · cm/cm$^2$) |
| --- | --- | --- | --- | --- |
| Example 30 | 100.0 g | 19.6g | 190° C./3 hr | 8.0 |
| Comparative Example 3 | 100.0 g | 5.5g | 170° C./1 hr | 3.0 |

EXAMPLE 29
Storage stability test of a thermosetting resin composition

In each example, an epoxy-containing resin and the diguanamine shown in Table 3 were blended in the amounts indicated in the same table. The resulting blend was kneaded in a twin roll, which had been heated to 90°–110° C. in advance, for 15–30 minutes until the blend became fully uniform. The blend was taken out in the form of a sheet and then ground. The resulting sample was left over in a drier maintained at 40° C., whereby its storage stability was judged. The results are shown in Table 3.

As can be seen from Table 3, each thermosetting resin composition according to the present invention has been found to have excellent storage stability.

As is shown in Table 4, a cured resin product available from each thermosetting resin composition according to the present invention has been found to have excellent flexibility.

EXAMPLE 31
Weathering test of a cured coating film obtained from a thermosetting resin composition Dissolved in 200 g of butyl cellosolve were 100.0 g of an epoxy-containing resin ("Almatex PD #7610"; product of Mitsui Toatsu Chemicals, Inc.; epoxy equivalent of solid: 530). The diguanamine (11.1 g) prepared in the same manner as in Example 1, was add to and dissolved in the

TABLE 3

| | Epoxy-containing resin | | Diguanamine | | Storage |
| --- | --- | --- | --- | --- | --- |
| | Kind | Amount blended (parts by weight) | kind | Amount blended (parts by weight) | stability at 40° C. |
| Example 29-1 | Epicoat #828 (Shell Kagaku K.K.) | 100.0 | Diguanamine (1) in Example 1 | 19.6 | At least 3 months |
| Example 29-2 | Epicoat #828 (Shell Kagaku K.K.) | 100.0 | Diguanamine (2) in Example 4 | 18.9 | At least 3 months |

EXAMPLE 30
Flexibility test of a cured resin product obtained from a thermosetting resin composition Blended were 100 g of an epoxy-containing resin ("Epicoat #828; product of Shell Kagaku K. K.) and 19.6 g of the diguanamine prepared in the same manner as in Example 1. They were kneaded in a twin roll, which had been heated at 90°–110° C. in advance, for 30 minutes until the blend became fully uniform. The blend was then taken out in the form of a sheet and then ground. The resulting sample was cured at 190° C. for 3 hours to obtain a cured resin product. The Charpy impact resistance of the cured resin product was measured as an index for flexibility. The results are shown in Table 4.

Incidentally, another cured resin product was produced as a comparative example under optimal curing conditions in a resulting solution, whereby a resin solution was prepared. The resin solution was coated on a galvanized sheet steel and then heated and cured at 200° C. for 40 minutes.

A weathering test was conducted by exposing the sheet steel so coated to light for 300 hours under a weather-o-meter. The surface gloss of the coating film on the sheet steel was measured in accordance with JIS K 5400 (specular reflection at 60°). As a result, the gloss retention was found to be 94%.

As has been demonstrated above, a cured resin product obtained from each thermosetting resin composition according to the present invention has been found to have excellent weatherability and is extremely useful as a paint resin.

EXAMPLE 32
Test on a coating film of a powder coating resin obtained from a thermosetting resin composition A resin solution of the thermosetting resin composition prepared in the same manner as in Example 31 was heated under reduced pressure to remove a solvent therefrom, whereby a resin was obtained in a solid form. The solid resin was coarsely ground in a coarse grinder, followed by fine grinding in an atomizer. The finely-ground particles so obtained were sifted through a 150-mesh sieve. Those passed through the sieve were employed for a test as a powder coating resin. The powder coating resin was coated on a bonderized sheet steel by electrostatic coating to give a film thickness of about 50 μm, and then heated at 200° C. for 40 minutes.

The coating film of the sheet steel so coated and heated was found to have good smoothness according to visual judgment. Furthermore, no peeling was observed on the film even after rubbing the film surface 50 times with a toluene-soaked cloth. It was a fully cured, excellent coating film.

Using a germicidal lamp (manufactured by Toshiba Corporation; 19W) as an ultraviolet light source, the sheet steel so coated, that is, a test sheet steel was exposed for 200 hours to ultraviolet light at a vertical distance of 25 cm. Neither blisters nor discoloration was observed on the surface of the coating film of the sheet steel. The surface gloss of the test sheet steel was measured in accordance with JIS K 5400 (specular reflection at 60°). As a result, the gloss retention was found to be 96%. The coating film thus had excellent ultraviolet light resistance.

EXAMPLE 33

Adhesion test of a thermosetting resin composition

Blended were 100 g of an epoxy-containing resin ("Epicoat #828"; product of Shell Kagaku K. K.) and 15.7 g of the diguanamine (1) prepared in the same manner as in Example 1. They were kneaded in a twin roll, which had been heated to 90°–110° C. in advance, until they were fully and homogeneously mixed. Using the resin so kneaded, steel sheets were adhered. The resin was then cured at 200° C. for one hour. The resin so cured was found to have a tensile shear adhesive strength of 176 kg/cm$^2$ at 25° C.

As has been demonstrated above, each thermosetting resin composition according to the present invention has been found to have excellent adhesion and is extremely useful as an adhesive resin or the like.

EXAMPLE 34

A polypropylene resin composition, which consisted of 84 parts by weight of "itsui NOBLEN BJH" (trade name for polypropylene resin manufactured by Mitsui-Toatsu Chemicals Inc.), 15 parts by weight of the diguanamine [formula (1)] obtained in Example 1 and 1 part by weight of dilauryl thiodipropionate, was kneaded at 190° C. for 6 minutes through a mixing roll and then kneaded and pelletized by an extruder. The resulting pellets were molded by an injection molding machine so that test pieces of 1/16 inch in thickness were prepared for the determination of flammability.

Using those test pieces, a test was conducted following the vertical flammability testing method specified under Subject 94 of Underwriters Laboratories Inc., U.S.A. Their flammability was found to be Level V-1. No melt dripped during combustion and each test piece so tested retained its original shape well. The polypropylene resin composition therefore had excellent flame retardance.

EXAMPLE 35

A polypropylene resin composition, which consisted of 75 parts by weight of "Mitsui NOBLEN BJH" (trade name for polypropylene resin manufactured by Mitsui-Toatsu Chemicals Inc.), 6 parts by weight of the diguanamine [formula (1)] obtained in Example 1, 18 parts by weight of "Exolit 422" (trade name for ammonium polyphosphate manufactured by Hoechst A. G.) and 1 part by weight of dilauryl thiodipropionate, was treated in a similar manner to Example 34 to prepare its test pieces. Using those test pieces, a flammability test was conducted in the same manner as in Example 34. Their flammability was found to be Level V-0 and each test piece so tested retained its original shape well. In addition, the combined use of the diguanamine of this invention with the phosphoruses was found to achieve a greater improvement in flame retardancy owing to their synergistic effects.

EXAMPLES 36–39

A polyethylene resin composition, which consisted of 75 parts by weight of "HIZEX 5100E" (trade name for polyethylene resin manufactured by Mitsui Petrochemical Industries Ltd.), 15 parts by weight of the diguanamine [formula. (2)] obtained in Example 4 and 10 parts by weight of phosphoruses shown in Table 5, was kneaded at 160° C. for 6 minutes through a mixing roll and then kneaded and pelletized by an extruder. In a similar manner to Example 34, the resulting pellets were treated to prepare test pieces for the determination of flammability and a test was conducted. The results of the test are shown in Table 5.

As shown in Table 5, the combined use of the diguanamine of this invention with the phosphoruses was found to achieve a greater improvement in flame retardancy of the polyethylene resin composition according to the present invention. It therefore had excellent flame retardance.

TABLE 5

| | | Flame retardancy | |
|---|---|---|---|
| Ex. No. | Phosphoruses | Level according to UL Standard 94 | Melt dripping |
| 36 | 2-Ethylhexyldiphenyl phosphate | V-0 | Not observed |
| 37 | Tris(tridecyl)-phosphite | V-1 | Not observed |
| 38 | Diethyl N,N-bis(2-hydroxyethyl)amino-methylphophonate | V-1 | Not observed |
| 39 | Ethylenebistris(2-cyanoethyl)phosphin oxide | V-1 | Not observed |

EXAMPLE 40

Eight parts by weight of the diguanamine [formula (1)] obtained in Example 1 and 12 parts by weight of diphenyl acid phosphate were added and dissolved in 50 parts by weight of butyl cellosolve under heating. The solvent was then removed from the resulting solution to prepare a solid. After 15 parts by weight of the solid so obtained were added to 85 parts by weight of "DAPOLE D-600" (trade name for diallyl phthalate resin manufactured by Fudow Co., Ltd.), they were mixed under heating at 60°–80° C. The resulting mixture was allowed to cool down. Three parts by weight of dicumyl peroxide was then added to the reaction mixture and mixed, whereby a diallyl phthalate resin composition was obtained. The resin composition so obtained was poured into a glass-made casting mold and cured so that test pieces of 1/16 inch in thickness were prepared for the determination of flammability.

Using those test pieces, a test was conducted in a similar manner to Example 34. As a result, it was found that their flammability was Level V-0 and each test piece so tested retained its original shape well. The diallyl phthalate resin composition therefore had excellent flame retardancy.

EXAMPLE 41

A nylon resin composition, which had been obtained by adding 10 parts by weight of the diguanamine [formula (1)] obtained in Example 1 to 90 parts by weight of pellets of nylon 66, was mixed in a Henschel mixer. The resulting mixture was then kneaded and pelletized by an extruder whose cylinder temperature was set at 280° C. The resulting pellets were molded by an injection molding machine so that test pieces of 1/16 inch in thickness were prepared for the determination of flammability.

Using those test pieces, a test was conducted in a similar manner to Example 34. As a result, it was found that their flammability was Level V-1, they were excellent in char formability and each test piece so tested retained its original shape well. The nylon resin composition therefore had excellent flame retardancy.

EXAMPLE 42

To 90 parts by weight of "DAPOLE D-600" (trade name for, diallyl phthalate resin manufactured by Fudow Co., Ltd.), 7 parts by weight of the diguanamine [formula (2)] obtained in Example 3 and 3 parts by weight of isocyanuric acid were added, followed by mixing under heating to 60°–80° C. The resulting mixture was allowed to cool down. Three parts by weight of dicumyl peroxide was then added to the reaction mixture and mixed, whereby a diallyl phthalate resin composition was obtained. The resin so obtained was poured into a glass-made plate and cured so that test pieces of 1/16 inch in thickness were prepared for the determination of flammability.

Using those test pieces, a test was conducted in a similar manner to Example 34. As a result, it was found that their flammability was Level V-0 and each test piece as tested retained its original shape well. The diallyl phthalate resin composition therefore had excellent flame retardancy.

EXAMPLES 43–46

In a similar manner to Example 41 except that the resin composition employed in Example 41 was substituted by those shown in Table 6, respectively, test pieces were prepared for the determination of flammability and tests were conducted. The results are shown in Table 6.

EXAMPLE 47

To 44 parts by weight of "Epicoat #828" (trade name for epoxy resin manufactured by Shell Japan Ltd.), 11 parts by weight of the diguanamine [formula (2)] obtained in Example 4, 9 parts by weight of isocyanuric acid and 36 parts by weight of methyl hexahydrophthalic anhydride were added. They were then mixed through a heating roll, whereby an epoxy resin composition was obtained. The resulting resin composition was poured into a casting mold and cured so that test pieces of 1/16 inch in thickness were prepared for the determination of flammability.

Using those test pieces, a test was conducted in a similar manner to Example 34. The results are shown in Table 6.

EXAMPLE 48

To 80 parts by weight of "ESTAR CR211" (trade name for unsaturated polyester resin manufactured by Mitsui Toatsu Chemicals, Inc.), 9 parts by weight of the diguanamine [formula (1)] obtained in Example 1, 11 parts by weight of cyanuric acid, 0.7 part by weight of methyl ethyl ketone peroxide and 0.3 part by weight of cobalt naphthenate were added. They were then mixed by a mixer, whereby an unsaturated polyester resin composition was obtained. The resulting resin composition was poured into a glass-made casting mold and cured so that test pieces of 1/16 inch in thickness were prepared for the determination of flammability.

Using those test pieces, a test was conducted in a similar manner to Example 34. The results are shown in Table 6.

TABLE 6

| | | Resin Composition | | | | Flame retardancy | |
| --- | --- | --- | --- | --- | --- | --- | --- |
| | | Diguanamine | | Isocyanuric acids or cyanuric acids | | Level according to UL | |
| Ex. No. | Resin | Kind | Amount added[1] | Kind | Amount added[1] | standards 94 | Melt dripping |
| 43 | Nylon 66 | Diguanamine [formula (1)] Ex. 1 | 7 | Isocyanuric acid | 3 | V-0 | Not observed |
| 44 | Polycarbonate | Diguanamine [formula (1)] Ex. 1 | 12 | Isocyanuric acid | 3 | V-0 | Not observed |
| 45 | Polyethylene terephthalate | Diguanamine [formula (2)] of Ex. 3 | 8 | Tris(2-hydroxyethyl) isocyanurate | 7 | V-0 | Not observed |
| 46 | Polystyrene | Diguanamine [formula (2)] of Ex. 3 | 11 | Isocyanuric acid | 9 | V-1 | Not observed |
| 47 | Epoxy | Diguanamine [formula (2)] of Ex. 4 | 11 | Isocyanuric acid | 9 | V-0 | Not observed |
| 48 | Unsaturated polyester | Diguanamine [formula (1)] of Ex. 1 | 9 | Isocyanuric acid | 11 | V-1 | Not observed |

[1]Amount added: parts by weight based on 100 parts by weight of the resin composition As shown in Examples 43-48, it has been found that the method for the flame retardation according to the present invention had an excellent flame retarding ability for the wide range of resin compositions including thermoplastic resin and thermosetting resin. It has also been found that the combined use of isocyanuric acids or cyanuric acids with the diguanamine of the present invention achieved a greater improvement in flame retardancy owing to their synergistic effects.

EXAMPLE 49

A polyphenylene ether resin composition, which consisted of 48 parts by weight of poly(2,6-dimethyl-1,4-phenylene ether), that is, a polyphenylene ether resin, 32 parts by weight of polystyrene, 11 parts by weight of the diguanamine [formula (1)] obtained in Example 1, 4 parts by weight of isocyanuric acid and 5 parts by, weight of "Exolit 422" (trade name for ammonium polyphosphate manufactured by Hoechst A. G.), was mixed in a Henschel mixer. The resulting mixture was then kneaded and pelletized by an extruder. The pellets so obtained were molded by an injection molding machine so that test pieces of 1/16 inch in thickness were prepared for the determination of flammability.

Using those test pieces, a test was conducted in a similar manner to Example 34. As a result, it was found that their flammability was Level V-0 and each test piece so tested retained its original shape well. The polyphenylene ether resin composition therefore had excellent flame retardancy.

EXAMPLE 50

To 100 parts by weight of polypropylene glycol (average molecular weight: 2,000), 0.4 part by weight of water (total water content in the reaction system) was added, followed by mixing for 60 minutes under heat at 40° C. To the reaction mixture, 2,4-tolylene diisocyanate was added in an amount to give 1.25 as an NCO/OH equivalent ratio and 1.0 as an NCO/H$_2$O equivalent ratio, which caused evolution of heat. After this heat evolution was over, the resulting mixture was heated to 120° C. at a heating rate of 3° C./min. The reaction mixture was maintained at 120° C. for 75 minutes and was stirred, whereby a reaction was conducted. The reaction mixture was cooled down to 80° C. and then thoroughly mixed with 30 parts by weight of 2,4-tolylene diisocyanate. The resulting mixture was cooled down to room temperature to prepare a prepolymer.

In the next place, 85 parts of the prepolymer so obtained, 15 parts by weight of the diguanamine [formula (1)] obtained in Example 1, 0.5 part by weight of "Silicone DC-199" (trade name; product of Dow Chemical Company), 1.0 part by weight of N-ethylmorpholine, 0.2 part by weight of triethylamine and 2.3 parts by weight of water were mixed. Immediately after that, the resulting mixture was injected into a mold and caused to expand in situ, whereby a polyurethane foam was produced.

Using that polyurethane foam, a flammability test was conducted. As a result, it was found that the foam had self-extinguishing properties and the foam so tested retained its original shape well. The urethane resin composition therefore had excellent flame retardancy.

EXAMPLE 51

A polypropylene resin composition, which consisted of 78 parts by weight of "Mitsui NOBLEN BJH" (trade name for polypropylene resin manufactured by Mitsui Toatsu Chemicals, Inc.), 5 parts by weight of the diguanamine [formula (1)] obtained in Example 1, 15 parts by weight of "Exolit 422" (trade name for ammonium polyphosphate manufactured by Hoechst A. G.), 1 part by weight of pentaethylenehexamine and 1 part by weight of dilauryl thiopropionate, was treated in a similar manner to Example 34 so that test pieces were prepared. Using those test pieces, a flammability test was conducted in a similar manner to Example 34. As a result, it was found that the resin composition was Level V-0, it had excellent self extinguishing properties and each test piece so tested retained its original shape well. It was also found that the combined use of the diguanamine of this invention with the phosphoruses and the amino-containing compounds achieved a greater improvement in flame retardancy owing to their synergistic effects.

EXAMPLE 52

Following the procedures of Example 51 except that an ethylene-propylene copolymer (containing 45 wt. % of propylene) was used instead of the polypropylene resin, the resulting resin composition was treated and a test was conducted. As a result, it was found that the resin composition so obtained was Level V-0, it had excellent self-extinguishing properties and each test piece so tested retained its original shape well.

In a method for the flame retardation of a resin according to the present invention, the combined use of the phosphoruses and the amino-containing compounds was found to achieve a greater improvement in flame retardancy. The resin composition therefore had excellent flame retardancy.

EXAMPLES 53-60

Polypropylene resin compositions, each of which consisted of 76 parts by weight of "Mitsui NOBLEN BJH" (trade name for polypropylene resin manufactured by Mitsui Toatsu Chemicals, Inc.), 5.5 parts by weight of the diguanamine [formula (2)] obtained in Example 3, 17 parts by weight of "Exolit 422" (trade name for ammonium polyphosphate manufactured by Hoechst A. G.), 0.5 wt. % of an amino-containing compound shown in Table 7 and 1 part by weight of dilauryl thiopropionate, were treated and tested in a similar manner to Example 34. The results are shown in Table 7.

As shown in Table 7, in a method for the flame retardation of a resin according to the present invention, the combined use of the phosphoruses and the amino-containing compounds with the diguanamine of the present invention achieved a greater improvement in flame retardancy. The resin composition therefore had excellent flame retardancy.

TABLE 7

| | | Flame retardancy | |
|---|---|---|---|
| Ex. No. | Amino-containing compounds | Level according to UL Standard 94 | Melt dripping |
| 53 | N,N'-Bis(2-aminoethyl)piperazine | V-0 | Not observed |
| 54 | N-(2-Aminoethyl)-morpholine | V-0 | Not observed |
| 55 | N-(2-Aminoethyl)-piperidine | V-0 | Not observed |
| 56 | Dicyandiamide | V-0 | Not observed |
| 57 | Guanidine. phosphate salt | V-0 | Not observed |
| 58 | Ethylenediamine-formaldehyde (½ molar ratio) reaction product | V-0 | Not observed |
| 59 | Piperazine- | V-0 | Not |

TABLE 7-continued

| Ex. No. | Amino-containing compounds | Flame retardancy | |
|---|---|---|---|
| | | Level according to UL Standard 94 | Melt dripping |
| | formaldehyde (½ molar ratio) reaction product | | observed |
| 60 | Pentamethylene-hexamine | V-0 | Not observed |

EXAMPLE 61

Thermal stability test of polyphenylene ether resin

Mixed in a Henschel mixer was a polyphenylene ether resin composition obtained by adding 0.1 wt. % of the diguanamine [formula (1)] obtained in Example 1 to a polyphenylene ether resin, which consisted of 45 parts by weight of a poly(2,6-dimethyl-1,4-phenylene ether) component having an intrinsic viscosity [η] of 0.52, 50 parts by weight of a polystyrene component and 5 parts by weight of a hydrogenated SBS rubber. The resin composition was kneaded in a molten state and pelletized in a twin-screw extruder whose cylinder temperature had been set at 300° C. The resulting pellets were molded by an injection molding machine whose cylinder temperature had been set at 290° C. so that test pieces of ⅛ inch in thickness were prepared for the determination of Izod impact strength. Half of the test pieces were left over for 200 hours in a circulating hot-air constant-temperature chamber at 130° C. for an aging test. Izod impact strength of the test pieces after the aging test was measured in accordance with ASTM D256. Similar to the above, the Izod impact strength of another half test pieces was measured without aging. The results of Izod impact strength before and after the aging test are shown in Table 8.

EXAMPLES 62 & 63

Thermal Stability Test of Polyphenylene Ether Resin

In a similar manner to the procedures described in Example 61 except that the diguanamine [formula (1)] was replaced by another diguanamine, the resulting resin composition was treated and a test was conducted. The results are shown in Table 8.

COMPARATIVE EXAMPLE 4

In a similar manner to the procedures described in Example 61 except for the omission of the diguanamine (1) obtained in Example 1, the resulting resin composition was treated and a test was conducted. The results are shown in Table 8.

TABLE 8

| | Diguanamine | Izod impact strength[1] (⅛" notched) (kg–cm/cm) | |
|---|---|---|---|
| | | Before aging | After aging |
| Ex. 61 | Diguanamine [formula (1)] of Ex. 1 | 12.6 | 7.2 (57) |
| Ex. 62 | Diguanamine [formula (2)] of Ex. 3 | 12.4 | 6.8 (55) |
| Ex. 63 | Diguanamine [formula (2)] of Ex. 4 | 12.5 | 7.0 (56) |
| Comp. Ex. 4 | None | 12.3 | 5.3 (43) |

[1]Each value in parentheses indicates the Izod impact strength after the aging in terms of percent retention based on that before the aging.

EXAMPLES 64–66

Thermal stability test of polyphenylene ether resin

In a similar manner to the procedures described in Example 61 except that additives, which will be described below, were added respectively to the polyphenylene ether resin composition, the resulting resin composition was treated and a test was conducted. The results are shown in Table 9.

TABLE 9

| | Additive | | Izod impact strength[1] (⅛" notched) (kg–cm/cm) | |
|---|---|---|---|---|
| | Kind | Amount added[2] | Before aging | After aging |
| Ex. 64 | [3] | 0.1 | 12.5 | 8.6 (69) |
| Ex. 65 | Triethylene-tetramine | 0.3 | 12.7 | 9.5 (75) |
| Ex. 66 | Tris(nonyl-phenyl) phosphite | 0.3 | 12.7 | 7.9 (62) |

[1]Similar to that in Table 8
[2]Wt. % based on the amount of the polyphenylene ether resin
[3]Pentaerythrityl tetrakis[3-(3,5-di-t-butyl-4-hydroxyphenyl)propionate]

EXAMPLE 67

Thermal Stability Test of Polyacetal Resin

A polyacetal resin composition, which had been obtained by adding 1.0 wt. % of the diguanamine [formula (2)] obtained in Example 3 to 100 parts by weight of a trioxane-dioxolan copolymer which contained 4 wt. % of a dioxolan structural unit having an intrinsic viscosity of 1.6, was pulverized for 40 minutes under heating at 200° C.

The resin composition so pulverized was charged in an open container. The air container was maintained in a circulating air drier set at 220° C. to measure the weight reduction of the resin composition. As a result, it was found that the thermal depolymerization rate of the resin composition was 0.68 wt. %/min. Incidentally, the thermal depolymerization rate of a diguanamine-free resin composition was 2.9 wt. %/min.

EXAMPLE 68

Thermal stability test of polyacetal resin

In a similar manner to the procedures described in Example 67 except that 1.0 parts by weight of the diguanamine [formula (1)] obtained in Example 1 and 1.0 wt. % of 2,2'-methylenebis(4-methyl-6-butylphenol) were added instead of 1.0 wt. % of the diguanamine [formula (2)] obtained following the procedures in Example 3, the resulting resin composition was treated and a test was conducted. As a result, the depolymerization rate of the resulting resin composition was found to be 0.08 wt. %/min.

As shown in Examples 67 and 68, the polyacetal resin compositions according to the present invention had significantly improved thermal stability.

EXAMPLE 69

Thermal stability test of polyethylene resin

A polyethylene resin composition, which consisted of 100 parts by weight of "Hizex 5100E" (trade name for polyethylene resin manufactured by Mitsui Petrochemical Industries Ltd), 1.0 part by weight of fine copper particles and 0.5 part by weight of the diguanamine [formula (1)] obtained in Example 1, was kneaded at 160° C. for 6 minutes through a mixing roll and was then compression-molded for 5 minutes at 150° C. and 200 Kg/cm$^2$, whereby a film sheet was obtained.

Using the film sheet so obtained, an accelerated heat deterioration test was conducted in an air atmosphere in a circulating hot-air oven set at 150° C. The time at which the test piece started discoloration was recorded as a deterioration start time. The thermal stability of the resin composition was judged according to the period until the deterioration start time. The results are shown in Table 10.

In a similar manner to the procedures described above except for the omission of 0.5 part by weight of the diguanamine [formula (1)] obtained in Example 1, the resulting resin composition was treated and a test was conducted. The results are shown in Table 10 as "Comparative Example 5".

TABLE 10

| | Diguanamine | Period until initiation of deterioration (day) |
| --- | --- | --- |
| Ex. 69 | Diguanamine [Formula (1)] of Example 1 | 20 or more |
| Comp. Ex. 5 | None | 1 |

EXAMPLE 70

Thermal stability test of polypropylene resin

A polypropylene resin composition, which consisted of 100 parts by weight of "Mitsui NOBLEN BJH" (trade name for polypropylene resin manufactured by Mitsui Toatsu Chemicals, Inc.), 1.0 part by weight of fine copper particles and 0.3 part by weight of the diguanamine [formula (2)] obtained in Example 3, was kneaded at 190° C. for 6 minutes through a mixing roll and was then compression-molded for 5 minutes at 180° C. and 200 Kg/cm$^2$, whereby a film sheet was obtained.

Using the film sheet so obtained, a test was conducted in a similar manner to the procedures described in Example 69. The results are shown in Table 11.

In a similar manner to the procedures described above except for the omission of 0.3 part by weight of the diguanamine (2) obtained in Example 3, the resulting polypropylene resin composition was treated and a test was conducted. The results are shown in Table 11 as "Comparative Example 6".

TABLE 11

| | Diguanamine | Period until initiation of deterioration (day) |
| --- | --- | --- |
| Ex. 70 | Diguanamine [Formula (2)] of Example 3 | 20 or more |
| Comp. Ex. 6 | None | 1 |

EXAMPLE 71

Compatibilization test of tertiary resin composed of polyamide resin, polyphenylene ether resin and polystyrene resin To a resin composition, which consisted of 45 parts by weight of a polyphenylene ether resin component composed of poly(2,6-dimethyl-1,4-phenylene ether) having an intrinsic viscosity [η] of 0.52, 50 parts by weight of a polystyrene resin component and 5 parts by weight of a hydrogenated SBS rubber component, 8 parts by weight of the diguanamine [formula (1)] obtained in Example 1 were added, followed by mixing in a Henschel mixer. The resulting mixture was kneaded in a molten state and pelletized in a twin-screw extruder whose cylinder temperature was set at 300° C. The pellets so obtained (54 parts by weight) were pulverized, to which 50 parts by weight of "Toyobo Nylon T-802" (trade name for polyamide resin manufactured by Toyoho Co., Ltd.) were added. The resulting resin composition was mixed in a Henschel mixer and was then kneaded in a molten state and pelletized by a twin-screw extruder whose cylinder temperature was set at 280° C.

As a result of observation of the tertiary resin composition by an electron microscope, it was found that the resin had a sea-isle structure and spheres having a controlled diameter of about 2.4 μm had been uniformly dispersed in the resin. This method was therefore excellent in the compatibilization of a resin.

EXAMPLE 72

Compatibilization test of binary resin composed of polyphenylene ether resin and polyamide-imide resin In a Henschel mixer, 70 parts by weight of a polyphenylene ether resin composed of poly(2,6-dimethyl-1,4-phenylene ether) having an intrinsic viscosity [η] of 0.52, 30 parts by weight of "TORLON 4203" (trade name for polyamide-imide resin manufactured by Amco Corporation) and 5 parts by weight of the diguanamine [formula (2)] obtained in Example 3 were mixed and then kneaded in a molten state and pelletized in a twin-screw extruder whose cylinder temperature was set at 330° C.

As a result of observation of the binary resin composition so obtained by an electron microscope, it was found that the molten resin had a sea-isle structure and spheres having a controlled diameter of about 3.6 μm had been uniformly dispersed in the resin. This process was therefore excellent for the compatibilization of a resin.

COMPARATIVE EXAMPLE 7

In a similar manner to the procedures described in Example 72 except for the omission of the diguanamine (2)

obtained in Example 3, a treatment was conducted so that a pelletized resin composition was obtained.

As a result of observation of the resin composition by an electron microscope, the molten resin had a sea-isle structure in which, however, true spheres and oval spheres of a totally-uncontrolled wide range of from 0.5 to even 40 μm had been dispersed. Thus, the compatibilization of those resins was very poor.

EXAMPLE 73

Preparation of N,N', N", N'''-tetrakis(5-hydroxy-3-oxapentyl)diguanamine

In a 3 l flask equipped with a stirrer, a thermometer, a $N_2$ inlet tube, a liquid inlet tube and a condenser, 314.4 g (1.0 mole) of the diguanamine [formula (1)] obtained in Example 1 and 1471.9 g (14.0 moles) of 5-amino-3-oxapentan-1-ol were charged. After the flask was fully purged with nitrogen gas, 30.0 g (0.3 mole) of concentrated sulfuric acid were gradually added under stirring. The reaction mixture was heated gradually under stirring and a reaction was conducted at 210° C. for 20 hours. The resulting reaction mixture was cooled down, followed by neutralization with a 50% aqueous solution of caustic soda. From the reaction mixture, a precipitate was removed by hot filtration and then, the excess 5-amino-3-oxapentan-1-ol was distilled off under reduced pressure, whereby 674.1 g of a pale-yellow oil were obtained.

As a result of an analysis by liquid chromatography, the crude product so obtained was found to contain 93% of a hydroxyl-containing diguanamine derivative composed, as a mixture, of 2,5-bis[4,6-bis(5-hydroxy-3-oxapentylamino)-1,3,5-triazin-2-yl]-bicyclo[2.2.1]heptane and 2,6-bis[4,6-bis(5-hydroxy-3-oxapentylamino)-1,3,5-triazin-2-yl]-bicyclo[2.2.1]heptane. The derivative was thereafter separated and analyzed for identification. In an infrared absorption spectrum, the derivative showed absorptions corresponding to hydroxyl (wide absorption at 3500 m$^{-1}$) and triazine ring (at 820 cm$^{-1}$). In a $^1$H nuclear magnetic resonance spectrum, the absorption (6.5, 6.7 ppm) based on $NH_2$ group of the starting compound disappeared and instead, an absorption based on $CH_2$ group was observed at 3.6 ppm. Its elemental analysis data were found to conform well with the calculated values as shown below.

Elemental analysis:

| | C | H | N |
|---|---|---|---|
| Found: | 52.1% | 7.5% | 20.8% |
| Calculated: | 52.24% | 7.56% | 21.01% |

EXAMPLE 74

Preparation of N,N',N",N'''-tetrakis(2-hydroxypropyl)diguanamine

In a 3 l flask equipped with a stirrer, a thermometer, an $N_2$ inlet tube and a condenser, 302.3 g (1.0 mole) of the diguanamine [formula (2)] obtained in Example 3, 751.1 g (10.0 moles) of 1-amino-2-propanol, 42.8 g (0.8 mole) of ammonium chloride and 274 g of ethylene glycol were charged. The flask was then fully purged with nitrogen gas. The reaction mixture was heated gradually under stirring and a reaction was conducted for 20 hours under reflux. The resulting reaction mixture was cooled down, followed by neutralization with a 50% aqueous solution of caustic soda. From the reaction mixture, a precipitate was removed by hot filtration and then, the excess 1-amino-2-propanol and ethylene glycol were distilled off under reduced pressure, whereby 541.4 g of a pale-yellow crude product were obtained. As a result of an analysis by liquid chromatography, the crude product so obtained was found to contain 83% of a hydroxyl-containing diguanamine derivative composed, as a mixture, of 1,3-bis[4,6-bis(2-hydroxypropylamino)-1,3,5-triazin-2-yl]-cyclohexane and 1,4-bis[4,6-bis(2-hydroxypropylamino)-1,3,5-triazin-2-yl]-cyclohexane. The derivative was thereafter separated and analyzed for identification. In an infrared absorption spectrum, the derivative showed absorptions corresponding to hydroxyl and triazine ring.

In a $^1$H nuclear magnetic resonance spectrum, the absorption based on $NH_2$ group of the starting compound disappeared and instead, an absorption based on a $CH_2$ group was observed newly. Its elemental analysis data were found to conform well with the calculated values as shown below.

Elemental analysis:

| | C | H | N |
|---|---|---|---|
| Found: | 53.7% | 7.8% | 26.1% |
| Calculated: | 53.91% | 7.92% | 26.20% |

EXAMPLE 75

Preparation of N,N',N",N'''-tetrakis(2-hydroxyethyl)diguanamine

In a 3 l flask equipped with a stirrer, a thermometer, an $N_2$ inlet tube and a condenser, 314.4 g (1.0 mole) of the diguanamine [formula (1)] obtained in Example 1, 1221.7 g (20.0 moles) of 2-aminoethanol and 64.2 g (1.2 moles) of ammonium chloride were charged. The flank was then fully purged with nitrogen gas. The reaction mixture was heated gradually under stirring and a reaction was conducted for 30 hours under reflux. The resulting reaction mixture was cooled down, followed by neutralization with a 50% aqueous solution of caustic soda. From the reaction mixture, a precipitate was removed by hot filtration and then, the excess 1-aminoethanol was distilled off under reduced pressure, whereby 500.4 g of a pale-yellow crude product were obtained. As a result of an analysis by liquid chromatography, the crude product so obtained was found to contain 79% of a hydroxyl-containing diguanamine derivative composed of a mixture of 2,5-bis[4,6-bis(2-hydroxyethylamino)-1,3,5-triazin-2-yl]-bicyclo[2.2;1] heptane and 2,6-bis[4,6-bis(2-hydroxyethylamino)-1,3,5-triazin-2-yl]-bicyclo[2.2.1]heptane. The derivative was thereafter separated and analyzed for identification. In an infrared absorption spectrum, the derivative showed absorptions corresponding to hydroxyl and triazine ring. In a $^1$H nuclear magnetic resonance spectrum, the absorption based on $NH_2$ group of the starting compound disappeared and instead, an absorption based on a $CH_2$ group was observed newly. Its elemental analysis data were found to conform well with the calculated values as shown below.

Elemental analysis:

| | C | H | N |
|---|---|---|---|
| Found: | 51.3% | 7.0% | 28.4% |
| Calculated: | 51.42% | 6.99% | 28.55% |

EXAMPLE 76

Preparation of N,N', N", N'''-tetrakis(4-hydroxyphenyl)diguanamine

In a 3 l flask equipped with a stirrer, a thermometer, an $N_2$ inlet tube and a condenser, 302.3 g (1.0 mole) of the diguanamine [formula (2)] obtained in Example 4, 873.0 g (8.0 moles) of p-aminophenol, 32.1 g (0.6 mole) of ammonium chloride and 1,400 g of diethylene glycol were charged. The flask was then fully purged with nitrogen gas. The reaction mixture was heated gradually under stirring and a reaction was conducted for 30 hours at 200° C. The resulting reaction mixture was cooled down, followed by neutralization with a 50% aqueous solution of caustic soda. A precipitate was removed from the reaction mixture by hot filtration, washed with deionized water and then dried under reduced pressure, whereby 643.9 g of a pale-yellow crude product were obtained. As a result of an analysis by liquid chromatography, the crude product so obtained was found to contain 1,4-bis[4,6-bis(4-hydroxyphenylamino)-1,3,5-triazin-2-yl]cyclohexane in an amount of 94%. The target product was thereafter separated and analyzed for identification. As a result, in an infrared absorption spectrum, the crude product had showed absorptions corresponding to hydroxyl, benzene ring and triazine ring. In a $^1$H nuclear magnetic resonance spectrum, the absorption based on $NH_2$ group of the starting compound disappeared and instead, an absorption based on a phenyl group was observed newly. Its elemental analysis data were found to conform well with the calculated values as shown below.

Elemental analysis:

|  | C | H | N |
| --- | --- | --- | --- |
| Found: | 64.2% | 5.0% | 20.8% |
| Calculated: | 64.47% | 5.11% | 20.88% |

EXAMPLE 77

Preparation of N,N',N'',N'''-tetrakis(3-hydroxypropyl)diguanamine

In a similar manner to the procedures described in Example 75 except that 1502.2 g (20.0 moles) of 3-aminopropanol were used instead of 1221.7 g (20.0 moles) of 2-aminoethanol, a reaction was conducted and the resulting reaction mixture was treated, whereby 554.9 g of a crude product were obtained. As a result of an analysis by liquid chromatography, the crude product so obtained was found to contain 84% of a hydroxyl-containing diguanamine derivative composed of mixture of 2,5-bis[4,6-bis(3-hydroxypropylamino)-1,3,5-triazin-2-yl]-bicyclo[2.2.1]heptane and 2,6-bis[4,6-bis(3-hydroxypropylamino)-1,3,5-triazin-2-yl]-bicyclo[2.2.1]heptane. The derivative was thereafter separated and in a similar manner to Example 75, analyzed for identification. Its elemental analysis data were found to conform well with the calculated values as shown below.

Elemental analysis:

|  | C | H | N |
| --- | --- | --- | --- |
| Found: | 54.8% | 7.6% | 25.4% |
| Calculated: | 54.93% | 7.74% | 25.62% |

EXAMPLE 78

Preparation of N,N',N'',N'''-tetraphenyldiguanamine

In a similar manner to Example 75 except that 931.3 g (10.0 moles) of aniline were used instead of 1221.7 g (20.0 moles) of 2-aminoethanol, a reaction was conducted and the resulting reaction mixture was treated, whereby 629.9 g of a crude product were obtained. As a result of an analysis by liquid chromatography, the crude product so obtained was found to contain 89% of a diguanamine derivative composed of a mixture of 2,5-bis[4,6-dianilino-1,3,5-triazin-2-yl]bicyclo[2.2.1]heptane and 2,6-bis[4,6-dianilino-1,3,5-triazin-2-yl]-bicyclo[2.2.1]heptane. The derivative was thereafter separated and in a similar manner to Example 75, analyzed for identification. Its elemental analysis data were found to conform well with the calculated values as shown below.

Elemental analysis:

|  | C | H | N |
| --- | --- | --- | --- |
| Found: | 71.6% | 5.5% | 22.6% |
| Calculated: | 71.82% | 5.54% | 22.64% |

EXAMPLE 79

Preparation of N-mono(4-methoxycarbonylphenyl)diguanamine

In a similar manner to the procedures described in Example 76 except that 151.2 g (1.0 mole) of methyl p-aminobenzoate were used instead of 873.0 g (8.0 moles of p-aminophenol, a reaction was conducted. The reaction mixture was cooled down, followed by neutralization with a 50% aqueous solution of caustic soda. The precipitate was thereafter removed from the reaction mixture by hot filtration, washed with deionized water and then dried under reduced pressure, whereby a pale yellow crude product was obtained. Subsequent to the extraction from the crude product with ethanol, the solvent was removed from the extract. The residue was thereafter dried under reduced pressure, whereby 374.5 g of an extracted product were obtained. As a result of an analysis by liquid chromatography, the extracted product was found to contain 79% of 1-(4,6-diamino-1,3,5-triazin-2-yl)-4-[4-amino-6-(4-methoxycarbonylphenylamino)-1,3,5-triazin-2-yl]-cyclohexane. The target product was separated and analyzed for identification. In an infrared absorption spectrum, the target product showed absorptions corresponding to ester and triazine ring. Its elemental analysis data were found to conform well with the calculated values as shown below.

Elemental analysis:

|  | C | H | N |
| --- | --- | --- | --- |
| Found: | 54.9% | 5.5% | 32.0% |
| Calculated: | 55.04% | 5.54% | 32.09% |

EXAMPLE 80

Preparation of an oxaalkyl-containing diguanamine derivative

In a 3 l flask equipped with a stirrer, a thermometer, an $N_2$ inlet tube, a liquid feed tube and a condenser, 157.2 g (0.5 mole) of a diguanamine obtained in Example 1, 15.0 g of potassium hydroxide and 500 g of N,N-dimethylformamide were charged. The flask was then fully purged with nitrogen gas. The reaction mixture was gradually heated to 130° C., at which temperature 1277.8 g (22.0 moles) of propylene oxide were gradually added dropwise to the reaction mixture under stirring. The dropwise addition was conducted over about 5 hours for the reaction. Even after the completion of the addition of Propylene oxide, the reaction was continued further for about 2 hours at the same temperature. The reaction mixture was then cooled down, followed by neutralization with a 30% aqueous solution of sulfuric acid. From the reaction mixture, N,N-dimethylformamide was distilled off under reduced pressure and the precipitate was collected by filtration, whereby a pale yellow, highly-viscous product was obtained. As a result of measuring a weight increase of the product, the amount of propylene oxide added in the reaction was found to be 1062.9 g. As a result of an analysis, the oxaalkyl-containing diguanamine derivative so obtained had an OH value of 162. Followings are its elemental analysis data found.

Elemental analysis:

|  | C | H | N |
|---|---|---|---|
| Found: | 60.2% | 9.8% | 5.6% |

EXAMPLE 81

Preparation of an oxaalkyl-containing diguanamine derivative

In a 3 l flask equipped with a stirrer, a thermometer, an $N_2$ inlet tube, a liquid feed tube and a condenser, 331.5 g of N,N',N",N'''-tetrakis(2-hydroxypropyl)diguanamine obtained in Example 74 and 6.6 g of potassium hydroxide were Charged. The flask was then fully purged with nitrogen gas. The reaction mixture was gradually heated to 130° C., at which temperature 2079.3 g of propylene oxide were gradually added dropwise to the reaction mixture under stirring. The dropwise addition was conducted over about 5 hours for the reaction. Even after the completion of the addition of propylene oxide, the reaction was continued further for about 2 hours at the same temperature. The reaction product so obtained was pale yellow and highly-viscous. As a result of measuring a weight increase of the product, it was found that the amount of propylene oxide added after the reaction was 1847.0 g.

As a result of an analysis, the oxaalkyl-containing diguanamine derivative so obtained was found to have an OH value of 93. Followings are its elemental analysis data found.

Elemental analysis:

|  | C | H | N |
|---|---|---|---|
| Found: | 60.8% | 10.0% | 3.9% |

EXAMPLE 82

Preparation of an oxaalkyl-containing diguanamine derivative

In a 1 l autoclave equipped with a stirrer, a thermometer, an $N_2$ inlet tube and a liquid feed tube, 134.1 g of N,N',N",N'''-tetrakis(4-hydroxyphenyl)-diguanamine obtained in Example 76, 100 g of diethylene glycol dimethyl ether and 2.0 g of potassium hydroxide were charged. The autoclave was then fully purged with nitrogen gas. The reaction mixture was gradually heated to 120° C., at which temperature 440.5 g of ethylene oxide were added to the reaction mixture in portions under stirring. The addition was conducted over about 5 hours for the reaction. Even after the completion of the addition of ethylene oxide, the reaction was continued further for about 2 hours at the same temperature. After the reaction mixture was cooled down, the autoclave was fully purged with nitrogen gas. The reaction mixture was then taken out of the autoclave. The reaction mixture so obtained was neutralized with a 30% aqueous solution of sulfuric acid. The diethylene glycol dimethyl ether was distilled off under reduced pressure. The precipitate was then collected by filtration, whereby a pale yellow, highly viscous product was obtained. As a result of measuring the weight increase of the product, it was found that the amount of ethylene oxide added in the reaction was 381.5 g.

As a result of an analysis, the oxaalkyl-containing diguanamine derivative so obtained was found to have an OH value of 139. Followings are its elemental analysis data found.

Elemental analysis:

|  | C | H | N |
|---|---|---|---|
| Found: | 57.0% | 8.1% | 5.3% |

EXAMPLE 83

Preparation of an oxaalkyl-containing diguanamine derivative

In a 3 l flask equipped with a stirrer, a thermometer, an $N_2$ inlet tube, a liquid charging tube and a condenser, 208.6 g of an N-methylol derivative of the diguanamine [formula (2)] obtained in Example 3 [with 1 mole of the diguanamine of formula (2), 7.3 equivalents of methylol group are combined], 200.0 g of diethylene glycol dimethyl ether and 5.0 g of potassium hydroxide were charged. The flask was then fully purged with nitrogen gas. The reaction mixture was gradually heated to 130° C., at which temperature 2032.8 g of propylene oxide were gradually added dropwise to the reaction mixture under stirring. The addition was conducted over about 8 hours for the reaction. Even after the completion of the addition of propylene oxide, the reaction was continued further for about 2 hours at the same temperature. The reaction mixture was then cooled down, followed by neutralization with a 30% aqueous solution of sulfuric acid. From the reaction mixture, the diethylene glycol dimethyl ether was distilled off under reduced pressure. The precipitate was then collected by filtration, whereby a pale yellow, highly viscous product was obtained. As a result of measuring the weight increase of the product, the amount of propylene oxide added after the reaction was found to be 1783.1 g.

As a result of an analysis, the oxaalkyl-containing diguanamine derivative so obtained was found to have an OH value of 86. Followings are its elemental analysis data found.

Elemental analysis:

|  | C | H | N |
|---|---|---|---|
| Found: | 60.1% | 10.0% | 2.7% |

EXAMPLE 84

Preparation of N,N',N",N"'-tetrakis(2-moprholinoethyl)diguanamine

In a similar manner to the procedures described in Example 76 except that 1041.5 g (8.0 moles) of N-aminoethylmorpholine were used instead of 873.0 g (8.0 moles) of p-aminophenol, a reaction was conducted and the resulting reaction mixture was treated. As a result of an analysis by liquid chromatography, the crude product so obtained was found to contain 92% of 1,4-bis[4,6-bis(2-morpholinoethylamino)-1,3,5-triazin-2-yl]-cyclohexane. The target product was thereafter separated and analyzed for identification. In an infrared absorption spectrum, the product showed an absorption corresponding to a triazine ring. Its elemental analysis data were found to conform well with the calculated values as shown below.

Elemental analysis:

|  | C | H | N |
|---|---|---|---|
| Found: | 57.4% | 8.2% | 26.1% |
| Calculated: | 57.27% | 8.28% | 25.97% |

EXAMPLE 85

A polypropylene resin composition, which consisted of 84 parts by weight of "Mitsui NOBLEN BJH" (trade name for polypropylene resin manufactured by Mitsui-Toatsu Chemicals Inc.), 15 parts by weight of N-mono(4-methoxycarbonylphenyl)diguanamine obtained in Example 79 and 1 part by weight of dilauryl thiodipropionate, was kneaded at 190° C. for 6 minutes through a mixing roll and then kneaded and pelletized by an extruder. The resulting pellets were molded by an injection molding machine so that test pieces of 1/16 inch in thickness were prepared for the determination of flammability.

Using those test pieces, a flammability test was conducted in a similar manner to Example 34. As a result, their flammability was found to be Level V-1. No melt dripped during combustion and each test piece so tested retained its original shape well. The polypropylene resin composition therefore had excellent flame retardancy.

EXAMPLE 86

A polypropylene resin composition, which consisted of 75 parts by weight of "Mitsui NOBLEN BJH" (trade name for polypropylene resin manufactured by Mitsui-Toatsu Chemicals Inc.), 6 parts by weight of N-mono(4-methoxycarbonylphenyl)diguanamine obtained in Example 79, 18 parts by weight of "EXOLIT 422" (trade name for ammonium polyphosphate manufactured by Hoechst A. G.) and 1 part by weight of dilauryl thiodipropionate, was treated in a similar manner to Example 34, whereby test pieces were prepared.

Using those test pieces, a flammability test was conducted in a similar manner to Example 34. Their flammability was found to be Level V-0 and each test piece so tested retained its original shape well. It was also found that, in a method for the retardation of a resin according to the present invention, the combined use of the diguanamine of the present invention with the phosphoruses achieved a greater improvement in flame retardancy. The polypropylene resin composition therefore had excellent flame retardance.

EXAMPLES 87 & 88

In a similar manner to Example 86 except that diguanamine derivatives as shown in Table 12 were used, respectively, instead of N-mono(4-methoxycarbonylphenyl)diguanamine obtained in Example 79, test pieces were prepared and a test was conducted. The results are shown in Table 12.

As shown in Table 12, it was found that in a flame-retardation method of a resin according to the present invention, the diguanamine derivatives of the present invention showed excellent effects on the improvement of flame retardancy and the combined use with the phosphoruses accelerated the improvement furthermore.

TABLE 12

| | | Flame retardancy | |
|---|---|---|---|
| Ex.No. | Diguanamine derivative | Level according to UL Standard 94 | Melt dripping |
| 87 | N,N,N",N" '-tetrakis(2-hydroxyethyl) diguanamine of Ex. 75 | V-0 | Not observed |
| 88 | N,N',N",N" '-tetrakis-(2-morpholinoethyl)-diguanamine of Ex. 84 | V-0 | Not observed |

EXAMPLE 89

A polyethylene resin composition, which consisted of 75 parts by weight of "HIZEX 5100E" (trade name for polyethylene resin manufactured by Mitsui Petrochemical Industries Ltd.), 15 parts by weight of N,N',N",N"'-tetrakis(2-hydroxypropyl)diguanamine obtained in Example 74 and 10 parts by weight of 2-ethylhexyldiphenylphosate, was kneaded at 160° C. for 6 minutes through a mixing roll and then kneaded and pelletized by an extruder. In a similar manner to Example 34, test pieces were prepared from these pellets for the determination of flammability.

Using those test pieces, a flammability test was conducted in a similar manner to Example 34. As a result, their flammability was found to be Level V-0. No melt dripped during combustion and each test piece so tested retained its original shape well. The method for the flame retardation of a resin according to the present invention had excellent effects on the improvement of flame retardancy.

EXAMPLE 90

A resin composition, which consisted of 75 parts by weight of an ethylene-propylene copolymer (containing 45 wt. % of propylene), 14 parts by weight of N,N',N",N"'-tetrakis(5-hydroxy-3-oxapentyl)diguanamine obtained in Example 73, 10 parts by weight of "EXOLIT 422" (trade name for ammonium polyphosphate manufactured by Hoechst A. G.) and 1 part by weight of dilauryl thiodipropionate, was treated in a similar manner to Example 34 to prepare its test pieces.

Using those test pieces, a flammability test was conducted in a similar manner to Example 34. Their flammability was found to be Level V-0 and each test piece so tested retained its original shape well.

EXAMPLE 91

A nylon resin composition, which had been obtained by adding 10 parts by weight of N,N',N",N"'-tetrakis(2-hydroxypropyl)diguanamine obtained in Example 74 to 90 parts by weight of pellets of nylon 66, was mixed in a Henschel mixer. The resulting mixture was then kneaded and pelletized by an extruder whose cylinder temperature was set at 280° C. The resulting pellets were molded by an injection molding machine so that test pieces of 1/16 inch in thickness were prepared for the determination of flammability.

Using those test pieces, a test was conducted in a similar manner to Example 34. It was found that their flammability was Level V-1 and they were excellent in char formability and each test piece so tested retained its original shape well.

EXAMPLE 92

A nylon resin composition, which consisted of 90 parts by weight of pellets of nylon 66, 7 parts by weight of N,N',N",N"'-tetrakis(2-hydroxypropyl)diguanamine obtained in Example 74 and 3 parts by weight of isocyanuric acid, was treated in a similar manner to Example 91, whereby test pieces were prepared.

Using those test pieces, a flammability test was conducted in a similar manner to Example 34. It was found that their flammability was Level V-0 and each test piece so tested retained its original shape well. The resin so obtained therefore showed excellent flame retardancy. It was also found that, in a method for the retardation of a resin according to the present invention, the combined use of isocyanuric acid with the diguanamine derivative of the present invention achieved a greater improvement in flame retardancy owing to their synergistic effects.

EXAMPLE 93

In a similar manner to Example 42 except that N,N',N",N"'-tetrakis(3-hydroxypropyl)diguanamine obtained in Example 77 was used instead of the diguanamine [formula (2)] obtained in Example 3, test pieces were prepared for the determination of flammability.

Using those test pieces, a flammability test was conducted in a similar manner to Example 34. It was found that their flammability was Level V-0 and each test piece so tested retained its original shape well. The resin so obtained therefore showed excellent flame retardancy.

EXAMPLE 94

To 44 parts by weight of "EPIKOTE #828" (trade name for epoxy resin manufactured by Shell Kagaku K. K.) 11 parts by weight of N,N',N",N"'-tetrakis(2-hydroxyethyl)diguanamine obtained in Example 75, 9 parts by weight of tris(2-hydroxyethyl)isocyanurate and 36 parts by weight of methylhexahydrophthalic anhydride were added and mixed in a heated roll, whereby an epoxy resin composition was obtained. The resin composition so obtained was poured into a casting mold and cured so that test pieces of 1/16 inch in thickness were prepared for the determination of flammability.

Using those test pieces, a flammability test was conducted in a similar manner to Example 34. It was found that their flammability was Level V-0 and each test piece so tested retained its original shape well. The epoxy resin composition therefore showed excellent flame retardancy.

EXAMPLE 95

In a similar manner to Example 48 except that N,N',N",N"'-tetrakis(2-hydroxypropyl)diguanamine obtained in Example 74 was used instead of the diguanamine [formula (1)] obtained in Example 1, test pieces were prepared for the determination of flammability.

Using those test pieces, a flammability test was conducted in a similar manner to Example 34. It was found that their flammability was Level V-1 and each test piece so tested its original shape well.

EXAMPLES 96–99

In a similar manner to Example 53 except that N,N',N",N"'-tetrakis(2-hydroxyethyl)diguanamine obtained in Example 75 and amino-containing compounds shown in Table 13 were used instead of the diguanamine [formula (2)] obtained in Example 3 and amino-containing compounds as shown in Table 7, respectively, test pieces were prepared. A flammability test was then conducted and results are shown in Table 13.

As shown in Table 13, it was found that, in a method for the retardation of a resin according to the present invention, a combined use of the phosphoruses and the amino-containing compound with the diguanamine derivative of the present invention improved the flame retardancy of the resin furthermore. The resin therefore showed excellent flame retardancy.

TABLE 13

| | | Flame retardancy | |
|---|---|---|---|
| Ex.No. | Amino-containing compound | Level according to UL Standard 94 | Melt dripping |
| 96 | N,N'-Bis(3-aminopropyl)piperazine | V-0 | Not observed |
| 97 | N-(2-Aminoethyl)-morpholine | V-0 | Not observed |
| 98 | Guanidine. phosphate salt | V-0 | Not observed |
| 99 | Propylenediamine-formaldehyde (½ molar ratio) reaction product | V-0 | Not observed |

EXAMPLE 100

Thermal stability test of polyphenylene ether resin

In a similar manner to the procedures described in Example 61 except that 0.1 wt. % of N,N',N",N"'-tetrakis(2-hydroxypropyl)diguanamine obtained in Example 74 and 0.3 wt. % of tris(nonylphenyl)phosphite were used instead of the diguanamine [formula (1)] obtained in Example 1, the resulting resin composition was treated and a test was conducted.

As a result, it was found that Izod impact strength of the resin before aging was 12.6, while that after aging was 8.1 and the Izod impact strength after aging in terms of a percent retention strength was 64%. The resin therefore had excellent thermal stability.

EXAMPLE 101

Thermal stability test of polyacetal resin

In a similar manner to the procedures described in Example 67 except that N,N',N",N"'-tetrakis(2-hydroxyethyl)diguanamine obtained in Example 75 was used instead of the diguanamine [formula (2)] obtained in Example 3, a treatment and a test were conducted. As a result, the resin composition so obtained was found to have a thermal depolymerization rate of 0.83 wt. %/min.

As described above, a method for the thermal stabilization of a resin according to the present invention made it possible to significantly improve the thermal stability of the polyacetal resin.

EXAMPLE 102

Thermal stability test of polypropylene resin

In a similar manner to the procedures described in Example 70 except that N,N',N",N"'-tetrakis(3-hydroxypropyl)diguanamine obtained in Example 77 was used instead of the diguanamine [formula (2)] obtained in Example 3, a film sheet was prepared.

Using the film sheet so obtained, a test was conducted in a similar manner to Example 69. As a result, it was found that the deterioration start time of the film was 20 days and more and the film had remarkably good thermal stability. The method for the thermal stabilization of a resin according to the present invention was therefore excellent.

EXAMPLE 103

Compatibilization test of binary resin composed of polyphenylene ether resin and polyether imide resin In a Henschel mixer, 60 parts by weight of a polyphenylene ether resin composed of poly(2,6-dimethyl-1,4-phenylene ether) having an intrinsic viscosity [η] of 0.52, 40 parts by weight of "ULTEM 1000" (trade name for polyether imide resin manufactured by Engineering Plastics, Ltd.) and 5 parts by weight of N,N',N",N"'-tetraphenyldiguanamine obtained in Example 78 were mixed and then kneaded in a molten state and pelletized in a twin-screw extruder whose cylinder temperature was set at 300° C.

As a result of observation of the binary resin composition so obtained by an electron microscope, it was found that the molten resin had a sea-isle structure and spheres having a controlled diameter of about 2.8 µm had been uniformly dispersed in the resin. This method was therefore excellent in the compatibilization of a resin.

EXAMPLE 104

Compatibilization test of tertiary resin composed of polyamide resin, polyphenylene ether resin and polystyrene resin In a similar manner to the procedures described in Example 71 except that N,N',N",N"'-tetrakis(2-hydroxyethyl)diguanamine obtained in Example 75 was used instead of the diguanamine [formula (1)] obtained in Example 1, a treatment and a test were conducted.

As a result of observation of the tertiary resin composition so obtained by an electron microscope, it was found that the resin in a molten state had a sea-isle structure and spheres having a controlled diameter of about 2.8 µm had been uniformly dispersed in the resin. This method was therefore excellent in the compatibilization of a resin.

EXAMPLE 105

In a 3 l flask equipped with a stirrer, a thermometer and a condenser, 300.3 g of paraformaldeyde (80% grade, 8.0 moles in terms of 100% formaldehyde) and 300.3 g of deionized water were charged, followed by adjustment of pH to 8.5 with a 10% aqueous solution of caustic soda. To the resultant mixture, 628.7 g (2.0 moles) of the diguanamine [formula (1)] obtained in Example 1 were added and mixed. The resulting mixture was reacted at 80° C. for 2 hours while its pH was maintained at 8.5–9.0. The reaction mixture was adjusted to pH 7.0 with a 20% aqueous solution of sulfuric acid, whereby an amino resin was obtained.

At the temperature kept at 90° C., 2,300 g of a 1.5 wt. % aqueous solution of polyvinyl alcohol ("Kuraray POVAL 205", trade name; product of Kuraray Co., Ltd.) were whipped through a dispersion mill and to it, the amino resin obtained above was added under stirring, whereby an emulsion was obtained. The emulsion was cooled down to 40° C., followed by the addition of 8.0 g of dodecylbenzenesulfonic acid. Under low-speed stirring by an anchor agitator, the resultant emulsion was heated gradually at a heating rate of about 10° C./hour. After the temperature reached 90° C., the reaction was conducted for two hours at this temperature, whereby a suspension of polymeric microspheres was obtained.

After being separated from the suspension by a centrifugal separator, the solid was dried under heat at 150° C. for 4 hours, whereby polymeric microspheres were obtained in the form of white powder.

It was found that the polymeric microspheres so obtained had excellent solvent resistance because even when being dipped in a solvent such as isopropanol, methyl ethyl ketone or xylene, they neither swelled nor were dissolved in such a solvent and in addition, they had excellent heat resistance because no fusion was observed even by heating in a drier set at 250° C.

EXAMPLE 106

In a 3 l flask equipped with a stirrer, a thermometer and a condenser, 450.4 g of paraformaldehyde (80% grade, 12.0 moles in terms of 100% formaldehyde) and 523.4 g of deionized water were charged, followed by adjustment of pH to 9.0 with a 10% aqueous solution of caustic soda. To the resultant mixture, 604.7 g (2.0 moles) of the diguanamine [formula (2)] obtained in Example 4 were added and mixed. The resulting mixture was reacted at 80° C. for 1 hour while its pH was maintained at 9.0–9.5. The reaction mixture was adjusted to pH 6.0 with a 20% aqueous solution of sulfuric acid, followed by one-hour reaction at 60° C. The reaction mixture was then adjusted to pH 7.0 with a 10% aqueous solution of caustic soda, whereby an amino resin was obtained.

At the temperature kept at 90° C., 3,300 g of a 1.0 wt. % aqueous solution of polyvinyl alcohol ("Kuraray POVAL 205" trade name; product of Kuraray Co., Ltd.) were whipped through a dispersion mill and to it, the amino resin obtained above was added under stirring, whereby an emulsion was obtained.

In a similar manner to Example 105, a reaction was conducted and the resulting reaction mixture was treated using the emulsion so obtained, whereby polymeric microspheres were obtained in the form of white powder.

No melt cohesion was observed even when the polymeric microspheres were heated in a drier set at 250° C. The polymeric microspheres therefore had excellent heat resistance.

EXAMPLE 107

In a 3 l flask equipped with a stirrer, a thermometer and a condenser, 811.5 g of 37% formalin (10.0 moles in terms of 100% formaldehyde) were charged, followed by the adjustment of pH to 8.0 with a 10% aqueous solution of sodium carbonate. To the resultant mixture, 604.7 g (2.0 moles) of the diguanamine [formula (2)] obtained in Example 3 were added and mixed. The resulting mixture was reacted at 90° C. for 2 hours while its pH was maintained at 8.0–8.5. To the reaction mixture, 40.0 g of oil orange S were added, followed by stirring for one hour, whereby a colored amino resin was obtained.

While the temperature was kept at 90° C., 600 g of a 5.0 wt. % aqueous solution of polyvinyl alcohol ("Kuraray POVAL 205" trade name; product of Kurdray Co., Ltd.) were whipped through a dispersion mill and to it, the colored amino resin obtained above was added under stirring, whereby an emulsion was obtained.

In a similar manner to Example 105, a reaction was conducted and the reaction mixture was treated using the emulsion so obtained, whereby polymeric microspheres were obtained in the form of powder colored in vivid orange.

EXAMPLE 108

The polymeric microspheres obtained in accordance with the method of each of Example 105–107 were added to "ALMATEX L-1042" (trade name for cold dry type acrylic resin manufactured by Mitsui Toatsu Chemicals, Inc.; NV: 40.0%) to give 30% as PWC and were then kneaded in a paint shaker, whereby a resin solution containing these polymeric microspheres was obtained. The resulting resin solution was coated on a galvanized sheet steel, followed by heat treatment at 140° C. for 20 minutes.

Using a fadeometer, the sheet steel so coated was exposed to irradiation for 50 hours to test the weather resistance of a coated film. As a result, blisters, discoloration or the like were not observed on the coated film at all. It therefore showed excellent weather resistance.

As shown in Examples 105–108, it was found that polymeric microspheres excellent in heat-, solvent- and weather-resistance could be obtained using novel specified diguanamines according to the present invention. It was also found that polymeric microspheres which are useful as a resinous colorant excellent in weather resistance, color and the like could be obtained by coloring the polymeric microspheres with a colorant.

EXAMPLE 109

In a manner similar to Example 34 except that polymeric microspheres obtained following the procedures of Example 106 were used instead of the diguanamine [formula (1)] obtained in Example 1, test pieces were prepared for the determination of flammability.

Using those test pieces, a flammability test was conducted in a similar manner to Example 34. Their flammability was found to be Level V-1 and each test piece so tested retained its original shape well. The polypropylene resin composition therefore had excellent flame retardancy.

EXAMPLE 110

In a similar manner to Example 35 except that the polymeric microspheres obtained following the procedures of Example 105 were used instead of the diguanamine [formula (1)] obtained in Example 1, test pieces for the determination of flammability were prepared.

Using those test pieces, a flammability test was conducted in a similar manner to Example 34. Their flammability was found to be Level V-0 and each test piece so tested retained its original shape well. In a process for the flame retardation of a resin according to the present invention, the combined use of the polymeric microspheres of the present invention with phosphoruses achieved a greater improvement in flame retardancy. This method was therefore excellent.

EXAMPLE 111

A nylon resin composition, which consisted of 90 parts by weight of pellets of nylon 66, 7 parts by weight of polymeric microspheres obtained following the procedures of Example 105 and 3 parts by weight of isocyanuric acid, was treated in a similar manner to Example 91, whereby test pieces for the determination of flammability were prepared.

Using those test pieces, a flammability test was conducted in a similar manner to Example 34. It was found that their flammability was Level V-0 and each test piece so tested retained its original shape well. The nylon resin composition therefore showed excellent flame retardancy. In was also found that in a method for the flame retardation of a resin according to the present invention, the combined use of isocyanuric-acid with polymeric microspheres of the present invention achieved a greater improvement in flame retardancy owing to their synergistic effects.

EXAMPLE 112

In a similar manner to Example 94 except that the polymeric microspheres obtained following the procedures of Example 105 were employed instead of N,N',N",N"'-tetrakis(2-hydroxyethyl)diguanamine obtained in Example 75, test pieces for the determination of flammability were prepared.

Using those test pieces, a flammability test was conducted in a similar manner to Example 34. As a result, their flammability was found to be Level V-0 and each test piece so tested retained its original shape well. The polymeric microspheres therefore showed excellent flame retardancy.

EXAMPLE 113

A polypropylene resin composition, which consisted of 76 parts by weight of "Mitsui NOBLEN BJH" (trade name for polypropylene resin manufactured by Mitsui Toatsu Chemicals, Inc.), 5.5 parts by weight of the polymeric microspheres obtained following the procedures of Example 105, 17 parts by weight of "Exolit 422" (trade name for ammonium polyphosphate manufactured by Hoechst A. G.), 0.5 part by weight of pentaethylene hexamine and 1 part by weight of dilauryl thiopropionate, was treated in a similar manner to Example 34 so that test pieces for the determination of flammability were prepared.

Using those test pieces, a flammability test was conducted in a similar manner to Example 34. As a result, it was found that the resin composition was Level V-0, it had excellent self extinguishing properties and each test piece so tested retained its original shape well. It was also found that in a method for the flame retardation of a resin according to the present invention, a combined use of phosphoruses and amino-containing compounds with the polymeric microspheres achieved a greater improvement in flame retardance owing to their synergistic effects. The resin composition therefore had excellent flame retardancy.

EXAMPLE 114

Preparation of diguanamine-derivative containing polyurethane resin composition and foam thereof To 30.0 parts by weight of N,N',N",N"'-tetrakis(5-hydroxy-3-oxapentyl)diguanamine obtained in Example 73 and 70.0 parts by weight of an oxaalkyl-containing diguanamine derivative obtained in Example 80, 0.1 part by weight of water (total water content in the reaction system) was added, followed by mixing for 60 minutes under heating at 40° C. To the reaction mixture, 2,4-tolylene diisocyanate was added in an amount to give 1.1 as an NCO/OH equivalent ratio and 1.0 as an NCO/H$_2$O equivalent ratio, which caused evolution of heat. After this heat evolution was over, the resulting mixture was heated to 120° C. at a heating rate of 3° C./min. The reaction mixture was kept at 120° C. for 75 minutes, followed by stirring for reaction. The reaction mixture was cooled down to 80° C. and then thoroughly mixed with 30 parts by weight of 2,4-tolylene diisocyanate. The resulting mixture was cooled down to room temperature to prepare a prepolymer.

In the next place, 100 parts of the prepolymer so obtained, 0.5 part by weight of "Silicone DC-199" (product of Dow Chemical Company), 1.2 parts by weight of N-ethylmorpholine, 0.2 part by weight of triethylamine and 2.7 parts by weight of water were mixed. Immediately after that, the resulting mixture was injected into a mold and caused to expand in situ, whereby a polyurethane foam was produced.

Using that polyurethane foam, a flammability test was conducted. As a result, it was found that the foam had self-extinguishing properties and the foam so tested retained its original shape well. The diguanamine-derivative-containing polyurethane resin composition therefore had excellent flame retardancy.

EXAMPLE 115

In a flask equipped with a stirrer, a thermometer and a condenser, 62.8 g (0.2 mole) of the diguanamine [formula (1)] prepared in the same manner as in Example 1, and 64.9 g of 37% formalin (0.8 mole in terms of 100% formaldehyde) were charged. While maintaining the pH of the resulting mixture at 8.0–8.5 with a 10% aqueous solution of potassium hydroxide, a reaction was conducted at 90° C. for 60 minutes, whereby an amino resin was obtained. To the resulting amino resin, 2.5 g of pulp dust, 10 g of milled fiber, 0.4 g of diammonium imidesulfonate and 2.0 g of zinc sterate were added, followed by kneading. The mass so obtained was dried for 4 hours in a drier set at 80° C., followed by pulverization in a ball mill, whereby a thermosetting molding composition was obtained. Using the composition as a sample, its flow was measured by circular disc method and its gas releasability upon molding was also measured so that the flowability upon molding was judged. The results are shown in Table 14.

As shown in Table 14, it was found that a thermosetting molding composition according to the present invention had excellent flowability upon molding and it was therefore significantly useful for the forming of the moldings complicated in shape.

COMPARATIVE EXAMPLE 8

In a reaction vessel similar to that employed in Example 115, 46.6 g (0.37 mole) of melamine and 92.4 g of 37% formalin (1.14 moles in terms of 100% formaldehyde) were charged. While maintaining the pH of the resulting mixture to 8.0–8.5 with a 10% aqueous solution of potassium hydroxide, a reaction was conducted at 90° C. for 60 minutes, whereby a resin solution was obtained.

In a similar manner to Example 115, the resulting resin solution was treated, whereby a molding composition was obtained. The flowability of the composition upon molding was judged as in Example 115. The results are shown in Table 14.

TABLE 14

| Properties Tested | Example 115 | Comp. Ex. 8 |
| --- | --- | --- |
| Flow by circular disc method (mm)[1] | 105 | 87 |
| Gas releasability upon forming | Good | Usual |

[1]The test was conducted in accordance with JIS-K6911.

EXAMPLE 116

In a flask equipped with a stirrer, a thermometer and a condenser, 30.0 g of paraformaldehyde (0.8 mole in terms of 100% formaldehyde) and 50.0 g of methanol were charged. The resulting mixture was adjusted to pH 8.0–8.5 with triethanolamine, to which 60.4 g (0.2 mole) of the diguanamine [formula (2)] prepared in the same manner as Example 3 were added and mixed. While maintaining the pH of the-resulting mixture at 8.0–8.5, a reaction was conducted at 70° C. for 2 hours, whereby an amino resin was obtained.

Glass cloths were each impregnated with a liquid formulation of the amino resin to give a solid resin content of 40%. The glass cloths so impregnated were subjected to desolvation at 80° C. and further to aging at 100° C., whereby prepregs were obtained. Those prepregs were stacked one over the other. The stacked prepregs were held between two mirror-finish stainless plates and cured at 140° C. and 30 kg/cm$^2$ for 15 minutes on a laminating press, whereby a laminate was obtained.

Test results of properties of the laminate are presented in Table 15.

TABLE 15

| Properties Tested | Example 116 |
| --- | --- |
| Arc-resistance (sec)[2] | 210 |
| Insulation resistance (under normal condition)[2] | 10$^{11}$ |
| Impact strength (kg · cm/cm)[2] | 5.3 |
| Bending strength (kg/mm$^2$)[2] | 28 |
| Heat resistance (°C.)[2] | 190 |
| Light stability[3] | Good |

[2]The test was conducted in accordance with JIS-K6911.
[3]A test piece was prepared in accordance with the method employed for the measurement of water absorption in JIS-K6911. Using the test piece, a test was conducted for 500 hours in a fadeometer.

As shown in Table 15, the formed products obtained from the thermosetting molding composition of the present invention were excellent in electrical characteristics, mechanical properties, heat resistance, light stability and the like.

EXAMPLE 117

In a flask equipped with a stirrer, a thermometer and a condenser, 129.7 g of 37% formalin (1.6 moles in terms of 100% formaldehyde) were charged, followed by the adjustment to pH 9.5 with a 10% aqueous solution of caustic soda. To the resulting solution, 120.8 g (0.4 mole) of the diguanamine [formula (2)] prepared in the same manner as in Example 4 were added and mixed. While maintaining the pH of the resulting mixture at 9.0–10.0, a reaction was conducted at 60° C. for one hour, whereby an amino resin was obtained. To 148.4 g (solid content: 100.0 g) of a liquid formulation of the amino resin, 1.0 g of ammonium nitrate and 2.0 g of calcium stearate were added and mixed. The resulting mixture and 120.0 g of barium sulfate were gradually added to, a kneader and kneaded. To the kneader, 40.0 g of glass-chopped strand (½ inch) were added successively. While being uniformly dispersed, the resulting mass was kneaded and then extruded through an extruder into pellets. Those pellets were dried for 4 hours in a drier set at 80° C., followed by pulverization in a mixer, whereby a thermosetting molding composition was obtained.

Using the molding composition as a sample, molding was conducted by a compression molder so that test pieces of 1/16 inch in thickness were prepared for the determination of flammability.

Using those test pieces, a test was conducted following the vertical flammability testing method specified under Subject 94 of Underwriters Laboratories Inc., U.S.A. It was found that their flammability was found to be Level V-0. It was also found that they had excellent self-extinguishing properties and each test piece so tested retained its original shape well. The molded products, which had been obtained from the thermosetting molding composition described above, therefore had excellent flame retardancy.

EXAMPLE 118

In a similar manner to the procedures described in Example 117 except that 120.8 g (0.4 mole) of the diguanamine [formula (2)] prepared in the same manner as in Example 4 were replaced by 94.3 g (0.3 mole) of the diguanamine [formula (1)] prepared in the same manner as in Example 1 and 54.7 g (0.1 mole) of N,N',N'',N'''-tetrakis (2-hydroxypropyl)diguanamine obtained following the procedures described in Example 74, a thermosetting molding composition was obtained and test pieces were prepared for the determination of flammability.

Using those test pieces, a flammability test was conducted in a similar manner to Example 117. As a result, it was found that their flammability was Level V-0 and each test piece so tested retained its original shape well. The molded products, which had been obtained from the thermosetting molding composition described above, therefore had an excellent flame retardancy.

EXAMPLE 119

In a flask equipped with a stirrer, a thermometer and a condenser, 60.0 g of paraformaldehyde (1.6 moles in terms of 100% formaldehyde) and 130.0 g of methanol were charged, followed by the adjustment to pH 9.5 with a 10% aqueous solution of caustic soda. To the resulting mixture, 125.6 g (0.4 mole) of the diguanamine [formula (1)] prepared in the same manner as in Example 1 were added and mixed. While maintaining the pH of the resulting mixture at 9.0–10.0, a reaction was conducted at 60° C. for 1 hour, whereby an amino resin was obtained.

To 181.8 g (solid content: 100.0 g) of a liquid formulation of the amino resin, 1.0 g of zinc nitrate, 5.0 g of zinc stearate and 50.0 g of calcium carbonate were added and mixed. A glass mat was thereafter coated with the resulting mixture on a polyethylene film to give 55% as a solid resin content. After being dried at 80° C. in hot air, the resulting prepreg was covered with another polyethylene film and pressed. As a result, impregnation was accelerated while it was defoamed, whereby a sheet-like product was obtained.

The sheet-like product was molded by a compression molder to prepare test pieces for the determination of its properties. Test results of the properties of the test pieces are shown in Table 16.

TABLE 16

| Properties Tested | Example 119 |
| --- | --- |
| Bending strength (kg/mm$^2$) | 16 |
| Heat resistance (°C.) | 200 |
| Light stability | Good |

As shown in Table 16, the thermosetting molding composition according to the present invention was found to have excellent mechanical properties, heat resistance, light stability and the like as a sheet molding material.

EXAMPLE 120

In a 3 l flask equipped with a stirrer, a thermometer and a condenser, 375.3 g of paraformaldehyde (80% grade, 10.0 moles in terms of 100% formaldehyde) and 250.0 g of deionized water were charged, followed by the adjustment of pH to 9.0 with a 20% aqueous solution of caustic soda. To the resultant mixture, 628.7 g (2.0 moles) of the diguanamine [formula (1)] prepared in the same manner as in Example 1 were added and mixed. The resulting mixture was reacted at 80° C. for 2 hours while its pH was maintained at 9.0–9.5. The reaction mixture was then adjusted to pH 7.0 with a 20% aqueous solution of sulfuric acid, whereby an amino resin was obtained.

Deionized water was added to the amino resin to adjust the solid resin content of the resulting solution to 73.0 wt. %. To the resulting mixture, 3.0 wt. % and 1.5 wt. %, each based on the solid content of the amino resin, of formic acid and sodium dodecylbenzenesulfonate were added, respectively and mixed. To the resulting mixture, 30 wt. %, based on the solid content of the amino resin, of trichlorotrifluoroethane were added under vigorous stirring. Stirring was continued further for about four minutes to disperse the resulting mixture uniformly, whereby a thermosetting expansion-forming composition was obtained.

The composition was transferred into a polyethylene-made cylindrical vessel. The vessel with the composition held therein was left over in a drier set at 150° C., subjected to foaming at about 48° C., which was the temperature of the composition at the time of foaming, and then cured. The elastic foam so obtained was then heat-treated at 180° C. for 40 minutes.

As a result of tests, the elastic foam so obtained was found to have 24 g/l bulk density, at least 90% percent shape restoration, 14 mm deflection at break and 0.14N/mm$^2$ tensile strength. It was also found that its fire resistance was rated as flame retardant.

EXAMPLE 121

In a 3 l flask equipped with a stirrer, a thermometer and a condenser, 300.3 g of paraformaldehyde (80% grade, 8.0 moles in terms of 100% formaldehyde) and 195.4 g of deionized water were charged, followed by adjustment of pH to 10.0 with a 20% aqueous solution of caustic soda. To the resultant mixture, 604.7 g (2.0 moles) of the diguanamine [formula (2)] prepared in the same manner as in Example 3 were added and mixed. The resulting mixture was reacted at 70° C. for 1 hour while its pH was maintained at 10.0–10.5.

In the next place, 41.6 g (0.4 mole) of sodium bisulfite were added to the reaction mixture and while maintaining its pH at 10.0–10.5, a reaction was conducted at 80° C. for 2 hours. The reaction mixture was adjusted to p.H 7.0 with a 20% aqueous solution of sulfuric acid, whereby a modified amino resin was obtained.

Deionized water was added to the modified amino resin to adjust the solid resin content of the resulting solution to 74.0 wt. %. To the resulting mixture, 3.0 wt. % and 1.5 wt. %, each based on the solid content of the modified amino resin, of formic acid and sodium alkylsulfonate ("Ratemur PS", trade name; 40% grade, product of Kao Corporation) were added, respectively, and mixed. To the resulting mixture, 20 wt. %, based on the solid content of the modified amino resin, of pentane were added under vigorous stirring. Stirring was continued further for about four minutes to disperse the reaction mixture uniformly, whereby a thermosetting expansion-forming composition was obtained.

The composition was treated in a similar manner to Example 120, subjected to foaming at about 37° C., which was the temperature of the composition at the time of foaming, and then cured, Whereby an elastic foam was obtained. As a result of tests, the elastic foam so obtained was found to have 12 g/l bulk density and 21 mm deflection at break.

EXAMPLE 122

In a 2 l flask equipped with a stirrer, a thermometer and a condenser, 300.3 g of paraformaldehyde (80% grade, 8.0 moles in terms of 100% formaldehyde), 170.0 g of deionized water and 100 g of ethanol were charged, followed by adjustment of pH to 13.0 with a 30% aqueous solution of caustic soda. To the resultant mixture, 604.7 g (2.0 moles) of the diguanamine [formula (2)] prepared in the same manner as in Example 4 were added and mixed. The resulting mixture was reacted at 80° C. for 3 hours while its pH was maintained at 13.0–13.5. The reaction mixture was then adjusted to pH 7.0 with a 30% aqueous solution of sulfuric acid, followed by ethanol removal, whereby an amino resin was obtained.

Deionized water was added to the amino resin to adjust the solid resin content of the resulting solution to 76.0 wt. %. To the resulting mixture, 1.5 wt. %, 1.5 wt. % and 0.5 wt. %, each based on the solid content of the amino resin, of formic acid, sodium alkylsulfonate ("Ratemur PS", trade name; 40% grade, product of Kao Corporation) and polyoxyethylenestearyl ether ("Emulgen 310" trade name; product of Kao Corporation] were added, respectively, and mixed. To the resulting mixture, 20 wt. %, based on the solid content of the amino resin, of pentane were added under vigorous stirring. Stirring was continued further for about four minutes to disperse the reaction mixture uniformly, whereby a thermosetting expansion-forming composition was obtained.

The composition was treated in a similar manner to Example 120, subjected to foaming at about 37° C., which was the temperature of the composition at the time of foaming, and was cured, whereby an elastic foam was obtained. After being heat-treated at 200° C. for 20 minutes, the elastic foam was subjected to milling under about 70% compression. This process was repeated five times.

As a result of tests, the elastic foam so obtained was found to have 15 g/l bulk density and at least 90% percent shape restoration. It was also found that its fire resistance was rated as flame retardant.

EXAMPLE 123

In a 3 l flask equipped with a stirrer, a thermometer and a condenser, 300.3 g of paraformaldehyde (80% grade, 8.0 moles in terms of 100% formaldehyde) and 187.5 g of deionized water were charged, followed by adjustment of pH to 10.0 with a 20% aqueous solution of caustic soda. To the resultant mixture, 628.7 g (2.0 moles) of the diguanamine [formula (1)] prepared in the same manner as in Example 1 were added and mixed. The resulting mixture was reacted at 70° C. for 1 hour while its pH was maintained at 10.0–10.5. In the next place, 41.6 g (0.4 mole) of sodium bisulfite were added to the reaction mixture and while maintaining its pH at 10.0–10.5, a reaction was conducted at 80° C. for 2 hours. The reaction mixture was then adjusted to pH 6.0 with a 10% aqueous solution of sulfuric acid and a reaction was conducted at 60° C. for one hour, whereby a modified amino resin was obtained.

Deionized water was added to the modified amino resin to adjust the solid resin content of the resulting solution to 75.0 wt. %. To the resulting mixture, 1.0 wt. %, 1.0 wt. % and 0.5 wt. %, each based on the modified amino resin content, of formic acid, sodium alkylsulfonate ("Ratemur PS" trade name; 40% grade, product of Kao Corporation) and sodium polyoxyethylene-oleylethersulfate ("Levenol WX", trade name, 26% grade, product of Kao Corporation) were added, respectively, and mixed. To the resulting mixture, 30 wt. %, based on the solid content of the modified amino resin, of trichlorotrifluoroethane were added under vigorous stirring. Stirring was continued further for about four minutes to disperse the reaction mixture uniformly, whereby a thermosetting expansion-forming composition was obtained.

The composition was transferred into a polyethylene-made cylindrical vessel. The vessel with the composition held therein was set in a treatment chamber equipped with electroscopes. The composition was exposed to hypersonic wave having a frequency of 2.45 GHz (power consumption of the composition: 110 kw per kg of water) from both the top and bottom of the chamber to conduct foaming and curing, whereby an elastic foam was obtained. The elastic foam so obtained was then heated at 200° C. for 20 minutes.

As a result of tests, the resulting elastic foam was found to have 4.2 g/l bulk density and at least 90% percent shape restoration.

EXAMPLE 124

To 500.0 g (solid content) of the modified amino resin obtained in the same manner as described in Example 123, 40.0 g (0.06 mole) of N,N',N'',N'''-tetrakis(5-hydroxy-3-oxapentyl)diguanamine obtained in the same manner as described in Example 73 were added and they were mixed, whereby a modified amino resin containing a diguanamine derivative was obtained.

Deionized water was added to the resin solution to adjust the solid content of the resulting solution to be 75.0 wt. %. The resin solution so obtained showed good water solubility and storage stability.

The resin solution was adjusted and treated in a similar manner to Example 123, whereby a thermosetting expansion-forming composition was prepared. The thermosetting composition was then cured and treated to prepare an elastic foam.

As a result of tests, the elastic foam was found to have 6.1 g/l bulk density and at least 90% percent shape restoration. It was also found that its fire resistance was rated as flame retardant.

EXAMPLE 125

In a 3 l flask equipped with a stirrer, a therometer and a condenser, 300.3 g of paraformaldehyde (80% grade, 8.0 moles in terms of 100% formaldehyde) and 240.0 g of deionized water were charged, followed by adjustment of pH to 10.0 with a 20% aqueous solution of caustic soda. To the resultant mixture, 147.2 g (0.3 mole) of N,N',N'',N'''-tetrakis(2-hydroxyethyl)diguanamine prepared in the same manner as in Example 75 and 534.4 g (1.7 moles) of the diguanamine [formula (1)] prepared in the same manner as in Example 1 were added and mixed. The resulting mixture was reacted at 60° C. for 2 hours while its pH was maintained at 10.0–10.5. The reaction mixture-was then adjusted to pH 7.0 with a 20% aqueous solution of sulfuric acid, whereby an amino resin was obtained.

Deionized water was added to the amino resin to adjust the solid resin content of the resulting solution to be 73.0 wt. %. To the resulting mixture, 3.0 wt. % and 1.5 wt. %, each based on the solid content of the amino resin, of formic acid and sodium alkylsulfonate ("Ratemur PS", trade name; 40% grade, product of Kao Corporation) were added, respectively, and mixed. To the resulting mixture, 20 wt. %, based on the solid content of the amino resin, of pentane were added under vigorous stirring. Stirring was continued further for about four minutes to disperse the reaction mixture uniformly, whereby a thermosetting expansion-forming composition was obtained.

The resulting composition was transferred into a polyethylene-made cylindrical vessel. The vessel with the composition held therein was left over in a drier set at 150° C., the composition was subjected to foaming at about 37° C., which was the temperature of the composition at the time of foaming, and then was cured, whereby an elastic foam was obtained.

As a result of tests, it was found that the elastic foam had 14 g/l bulk density and 24 mm deflection at break and its fire resistance was rated as flame retardant.

As described in Examples 120–125, it was found that the use of novel specified diguanamines and derivatives thereof according to the present invention made it possible to obtain thermosetting expansion-forming compositions which could be prepared easily and had excellent dispersibility and solubility in a solvent such as water. It was also found that elastic foams having excellent mechanical properties, flame retardancy and the like could be obtained by foaming and curing the above thermosetting expansion-forming compositions.

We claim:

1. A process for the preparation of a diguanamine derivative, which comprises reacting at least one diguanamine selected from diguanamines represented by the following formula (1):

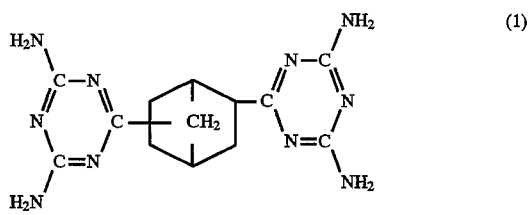
(1)

wherein the bonding sites of the 4,6-diamino-1,3,5-triazin-2-yl groups are the 2,5- or 2,6-positions, or by the following formula (2):

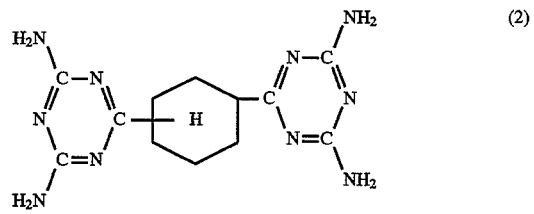
(2)

wherein the bonding sites of the 4,6-diamino-1,3,5-triazin-2-yl groups are the 1,2-, 1,3- or 1,4-positions, with at least one amine selected from amines containing at least one amino group and at least two carbon atoms.

2. A process according to claim 1, wherein said amine is a compound represented by the following formula:

HO—Y$_9$—NH$_2$ wherein Y$_9$ is a divalent group containing at least two carbon atoms.

3. A process according to claim 2, wherein the compound represented by the formula HO—Y$_9$—NH$_2$ is a compound selected from the group consisting of 2-amino-ethanol, 1-aminopropan-2-ol, 2-aminobutan-1-ol, 3-aminopropan-1-ol, 5-amino-3-oxapentan-1-ol and 4-aminophenol.

4. A process for the preparation of a diguanamine derivative which comprises subjecting at least one diguanamine, which is selected form diguanamines represented by the following formula (1):

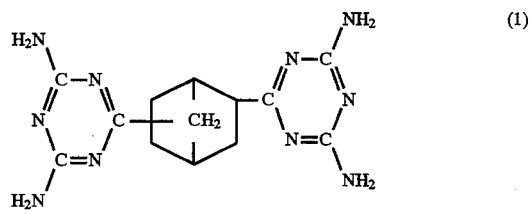
(1)

wherein the bonding sites of the 4,6-diamino-1,3,5-triazin-2-yl groups are the 2,5- or 2,6-positions, or by the following formula (2):

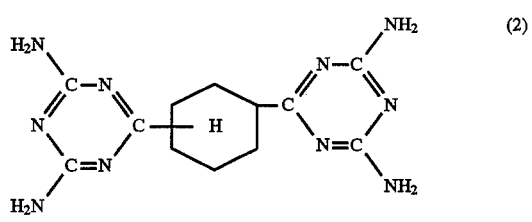
(2)

wherein the bonding sites of the 4,6-diamino-1,3,5-triazin-2-yl groups are the 1,2- 1,3- or 1,4-positions, and at least one epoxide to an addition reaction so as to obtain a diguanamine derivative represented by the following formula (11):

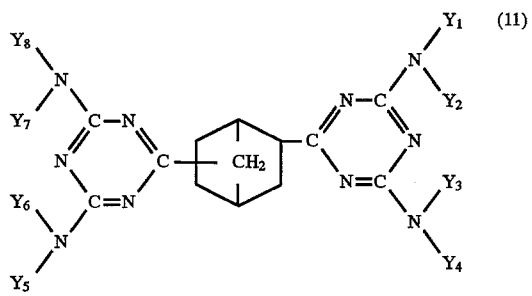
(11)

wherein the bonding sites of the 1,3,5-triazin-2-yl groups are the 2,5- or 2,6-positions, and Y$_1$, Y$_2$, Y$_3$, Y$_4$, Y$_5$, Y$_6$, Y$_7$ and $Y_8$ are the same or different and individually represent a substituent selected from the group consisting of a hydrogen atom and groups containing at least two carbon atoms, with the proviso that at least one of $Y_5$, $Y_6$, $Y_7$ and $Y_8$ is a group containing at least two carbon atoms, or by the following formula (12):

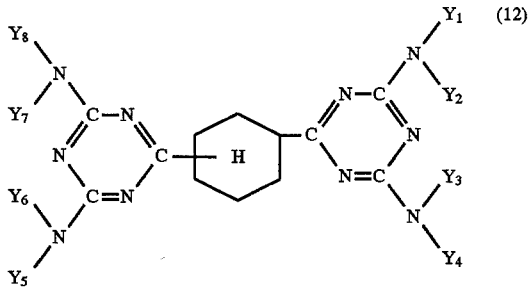
(12)

wherein the bonding sites of the 1,3,5-triazin-2-yl groups are the 1,2-, 1,3- or 1,4-positions and $Y_1$, $Y_2$, $Y_3$, $Y_4$, $Y_5$, $Y_6$, $Y_7$ and $Y_8$ have the same meanings as defined in formula (11) and wherein at least one of $Y_1$, $Y_2$, $Y_3$, $Y_4$, $Y_5$, $Y_6$, $Y_7$ and $Y_8$ represents a group selected from the group consisting of groups represented by the following formula (13):

$$HO-(-Y_{10}-O-)_m-Y_9- \quad (13)$$

wherein $Y_{10}$ is selected from the group consisting of ethylene, trimethylene and tetramethylene which may optionally contain one or more substituent groups containing 2–22 carbon atoms, m is an integer selected from 1 to 100, and $Y_9$ is a divalent group containing at least two carbon atoms, or by the following formula (14):

$$HO-(-Y_{10}-O-)_m-CH_2- \quad (14)$$

wherein $Y_{10}$ and m have the same meanings as defined in formula (13).

5. A process according to claim 4, wherein said epoxide is selected from ethylene oxide and propylene oxide.

* * * * *